United States Patent [19]
Kriesel et al.

[11] Patent Number: 6,126,642
[45] Date of Patent: Oct. 3, 2000

[54] PATIENT CONTROLLED FLUID DELIVERY DEVICE

[75] Inventors: Marshall S. Kriesel, Saint Paul; Farhad Kazemzadeh, Bloomington, both of Minn.; William W. Feng, Lafayette, Calif.; Thomas N. Thompson, Richfield, Minn.

[73] Assignee: Science Incorporated, Bloomington, Minn.

[21] Appl. No.: 09/165,429

[22] Filed: Oct. 2, 1998

[51] Int. Cl.[7] .................................................. A61M 5/00
[52] U.S. Cl. ........................ 604/207; 604/218; 604/131
[58] Field of Search ................................... 604/207, 208, 604/209, 210, 211, 218, 224, 131, 132, 134, 139

[56] References Cited

U.S. PATENT DOCUMENTS

| | | |
|---|---|---|
| 3,550,458 | 12/1970 | Dunlop et al. . |
| 3,563,023 | 2/1971 | Breed . |
| 3,563,024 | 2/1971 | Breed . |
| 3,606,072 | 9/1971 | Breed . |
| 3,731,021 | 5/1973 | Barnard . |
| 4,828,551 | 5/1989 | Gertler et al. . |
| 5,009,641 | 4/1991 | Gorton . |
| 5,011,477 | 4/1991 | Winchell et al. . |
| 5,061,243 | 10/1991 | Winchell et al. ....................... 604/132 |
| 5,069,668 | 12/1991 | Boydman . |
| 5,084,021 | 1/1992 | Baldwin . |
| 5,135,491 | 8/1992 | Baldwin . |
| 5,224,934 | 7/1993 | Payne et al. . |
| 5,232,448 | 8/1993 | Zdeb . |
| 5,456,679 | 10/1995 | Balaban et al. . |
| 5,466,227 | 11/1995 | Kessenich . |
| 5,514,097 | 5/1996 | Knauer ................................... 604/136 |
| 5,700,244 | 12/1997 | Kriesel . |
| 5,810,779 | 9/1998 | Baker et al. ............................ 604/151 |
| 5,876,377 | 3/1999 | Kriesel ................................... 604/133 |

FOREIGN PATENT DOCUMENTS

WO95/08359  3/1995  WIPO .

*Primary Examiner*—Glenn K. Dawson
*Assistant Examiner*—Catherine Serke
*Attorney, Agent, or Firm*—James E. Brunton

[57] ABSTRACT

A compact, patient controlled fluid dispenser for use in controllably dispensing fluid medicament at a selected uniform rate. The device is of an all mechanical construction and is ideally suited for the reliable patient administration of pain killing drugs in the home care environment. To positively regulate the patient administration of the medicament, the intervals at which a selected medicament can be administered, as well as the volume of the dose of the medicament to be administered, is preset by the treating physician and, once set, cannot be altered by the patient. More particularly, the device setting can only be operated by a small physician's key that remains in the possession and control of the treating physician or health care worker.

34 Claims, 36 Drawing Sheets

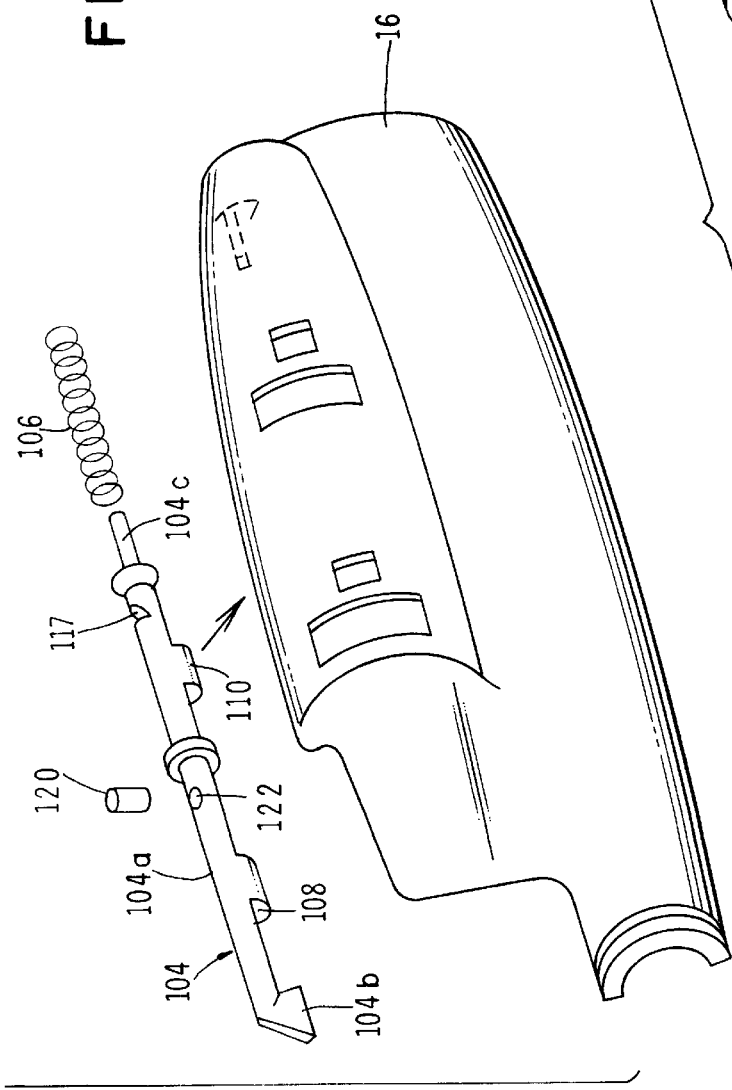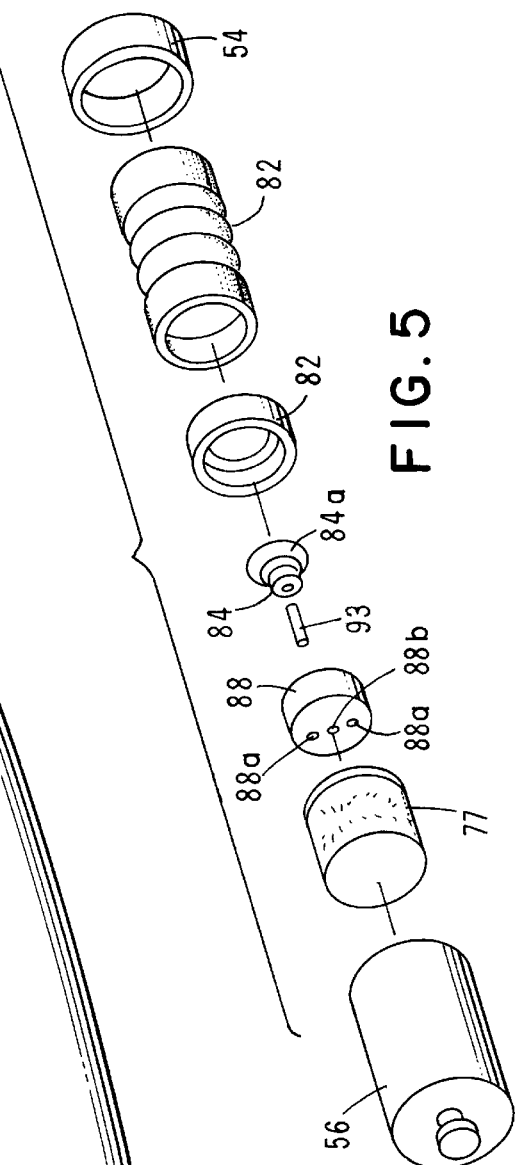

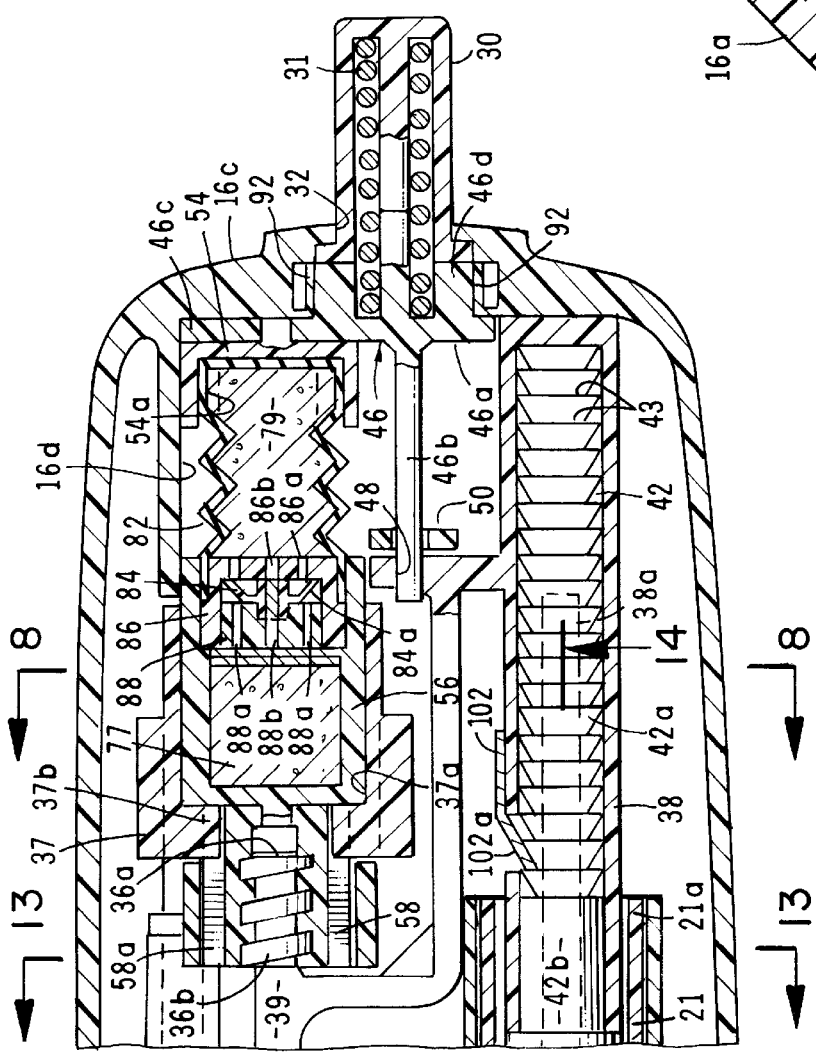
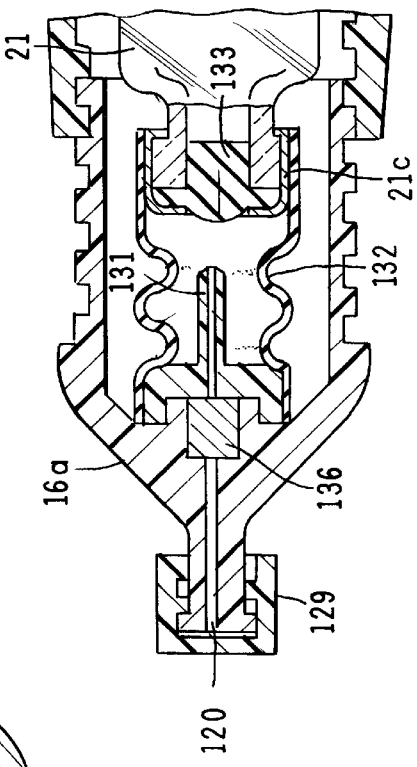
FIG.6B
FIG.16

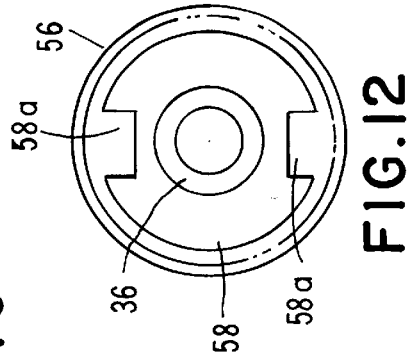
FIG. 9
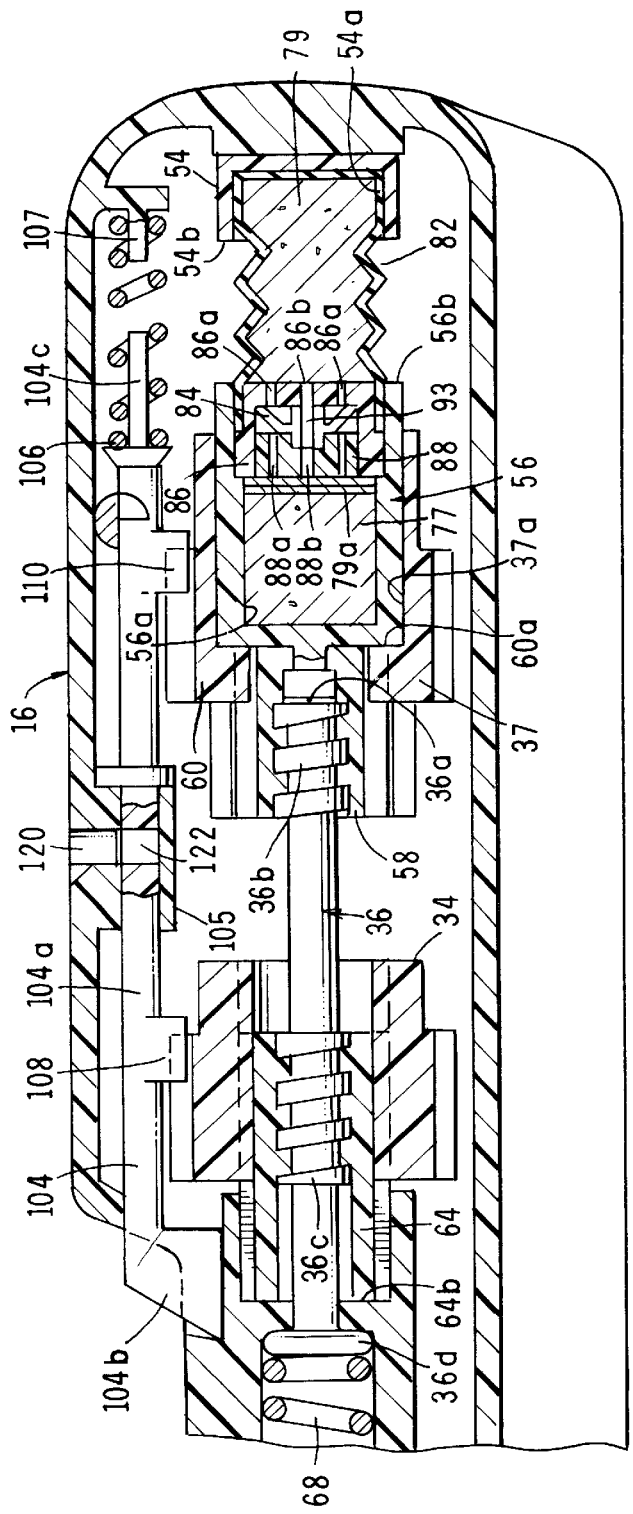
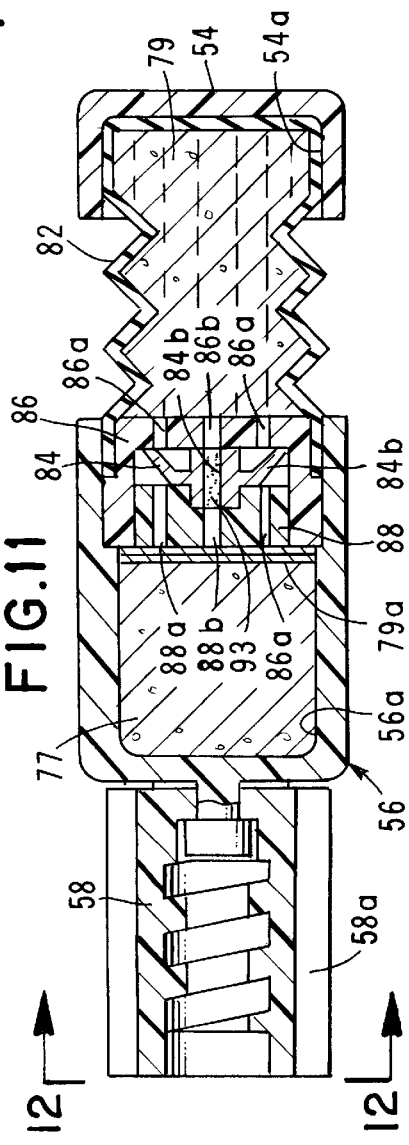
FIG. 11
FIG. 12

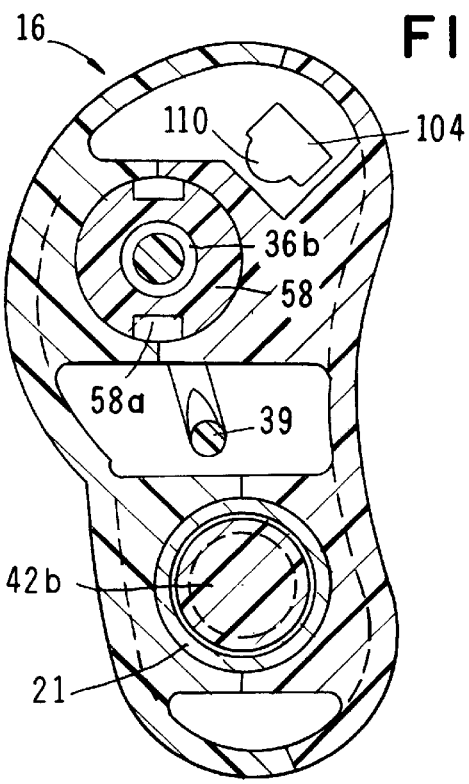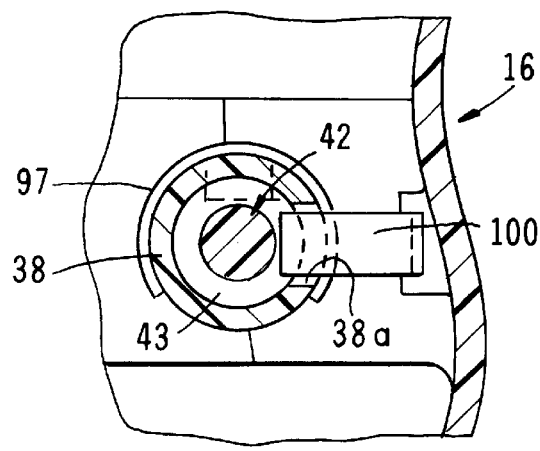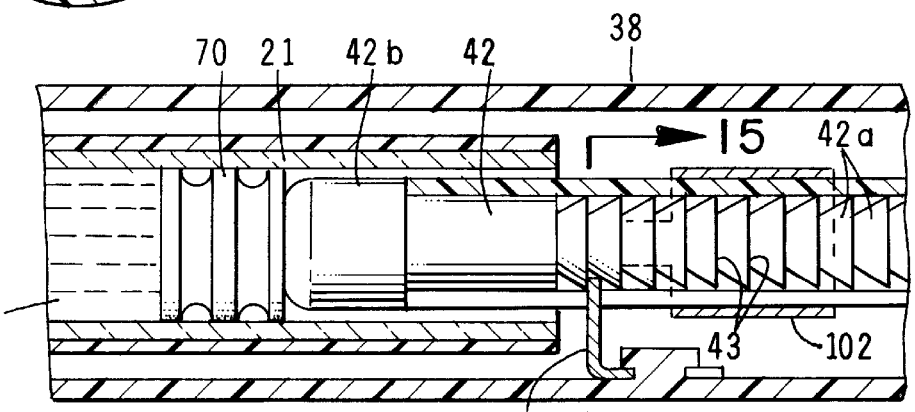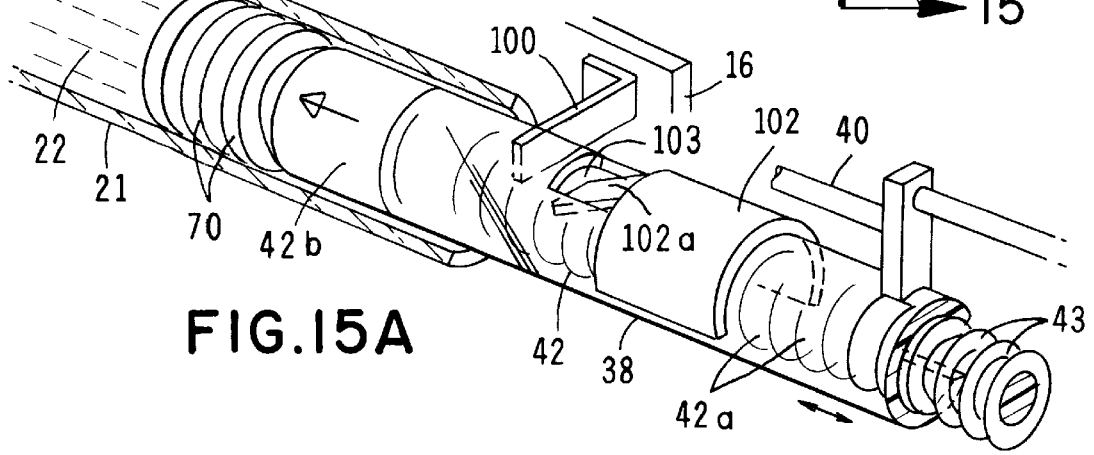

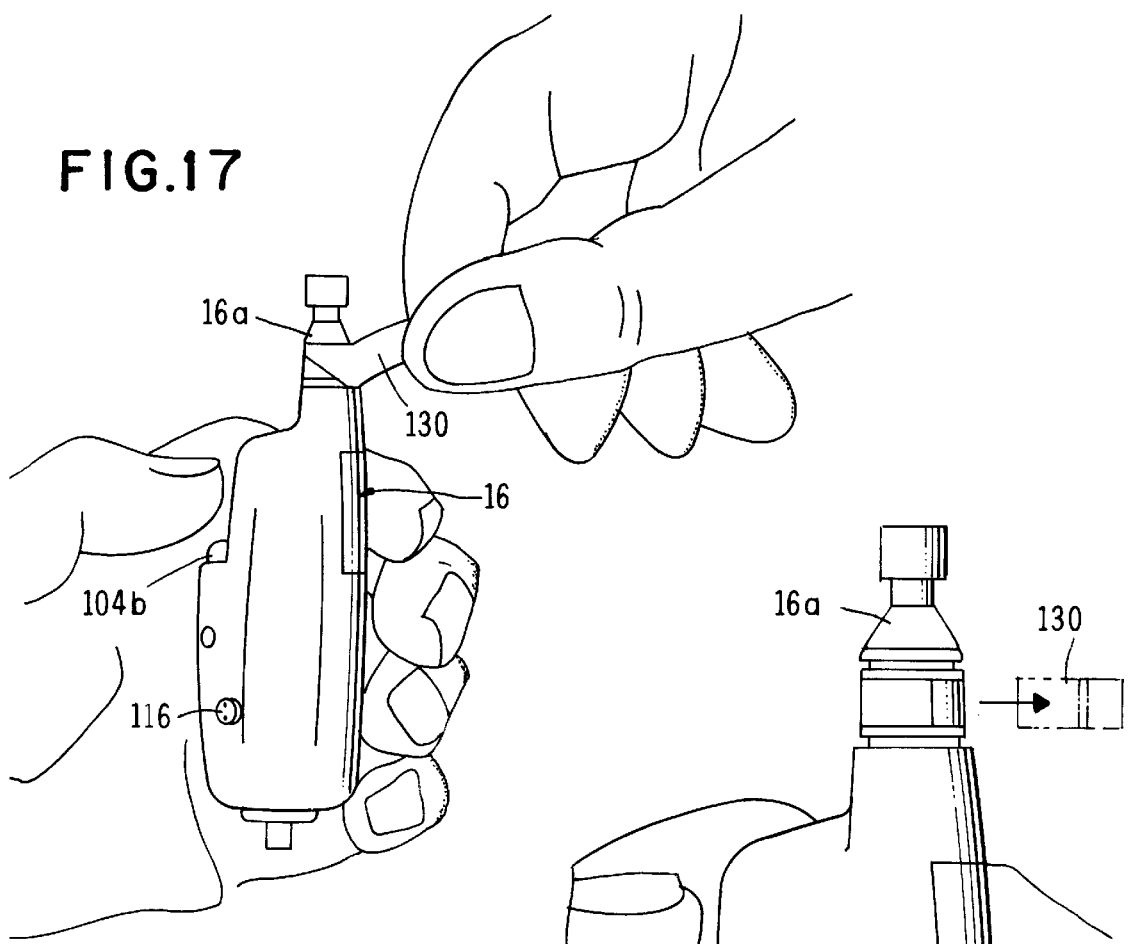
FIG.17
FIG.17A
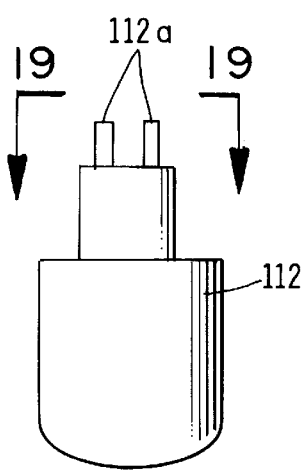
FIG.18
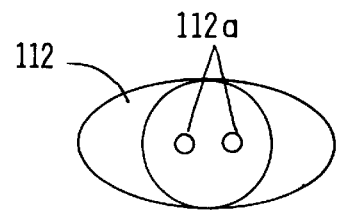
FIG.19

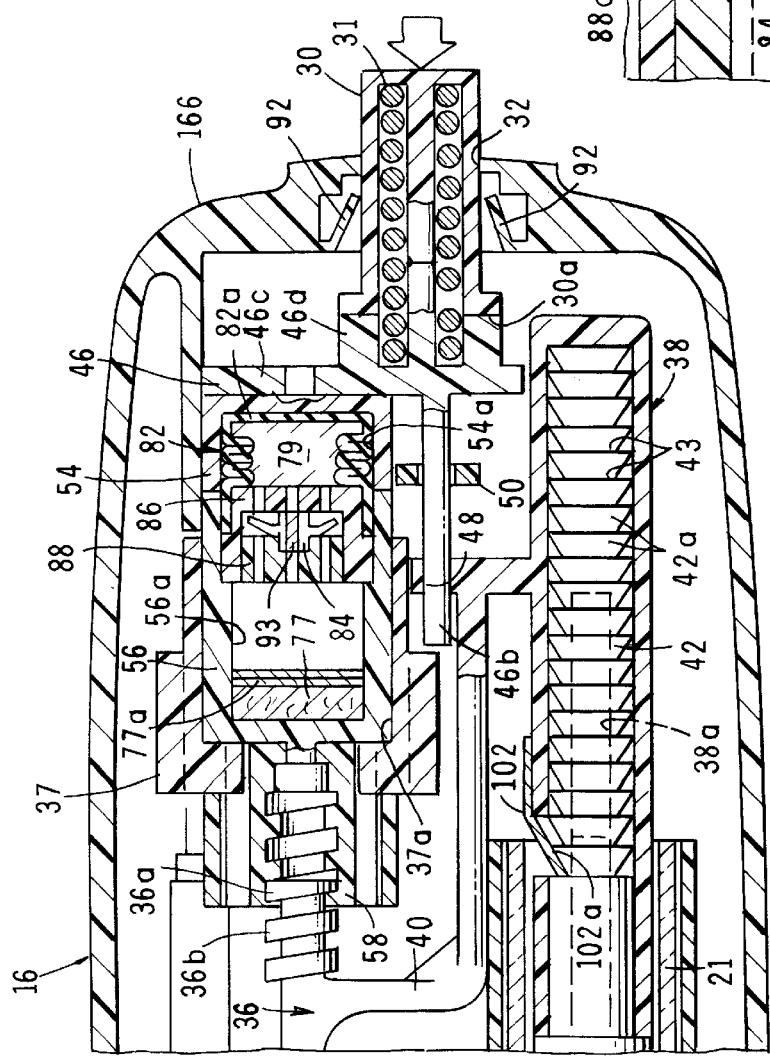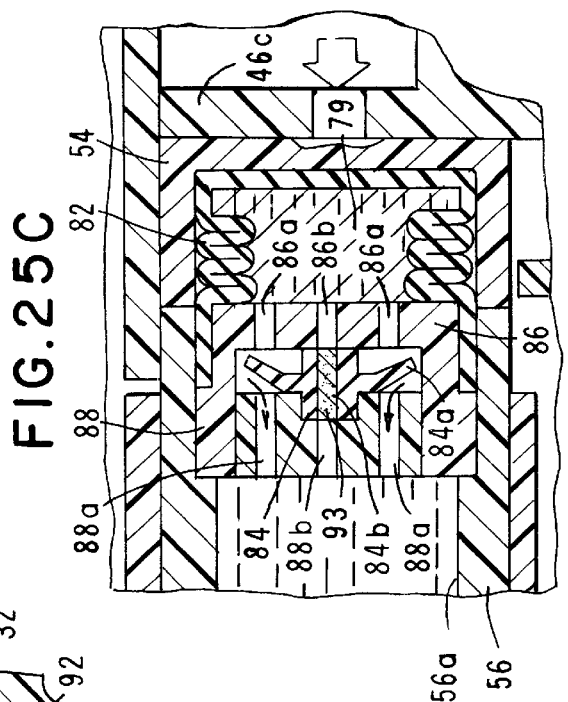
FIG.25B
FIG.25C

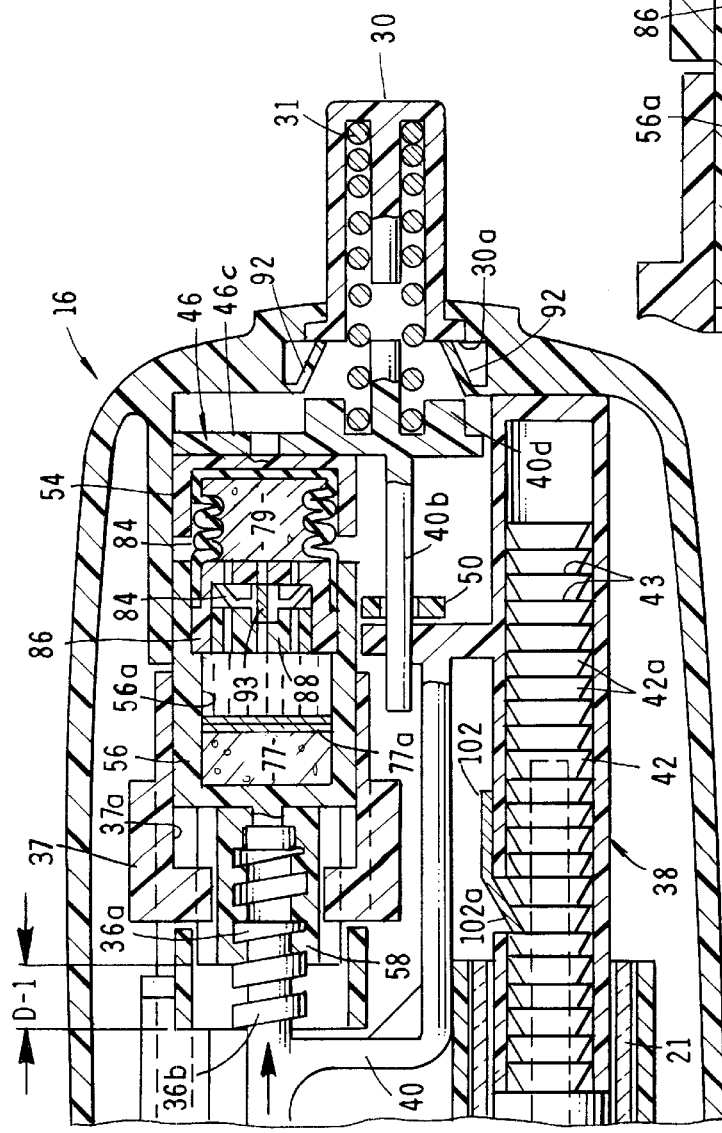
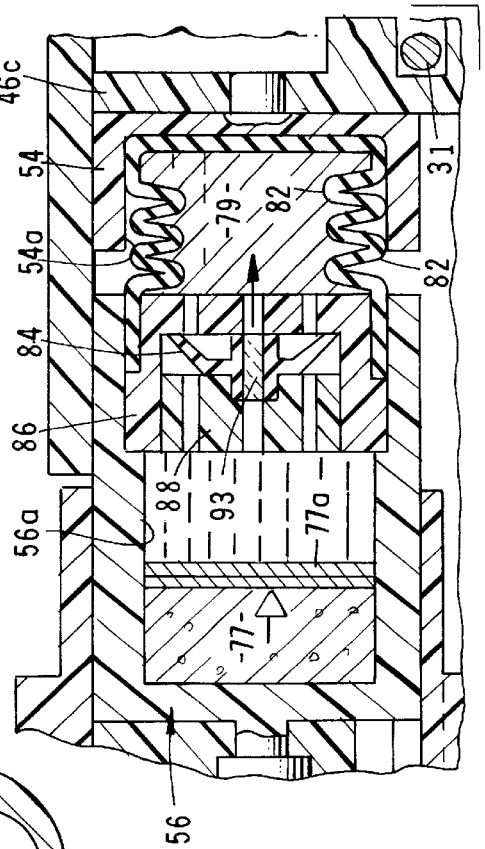
FIG.26B
FIG.26C

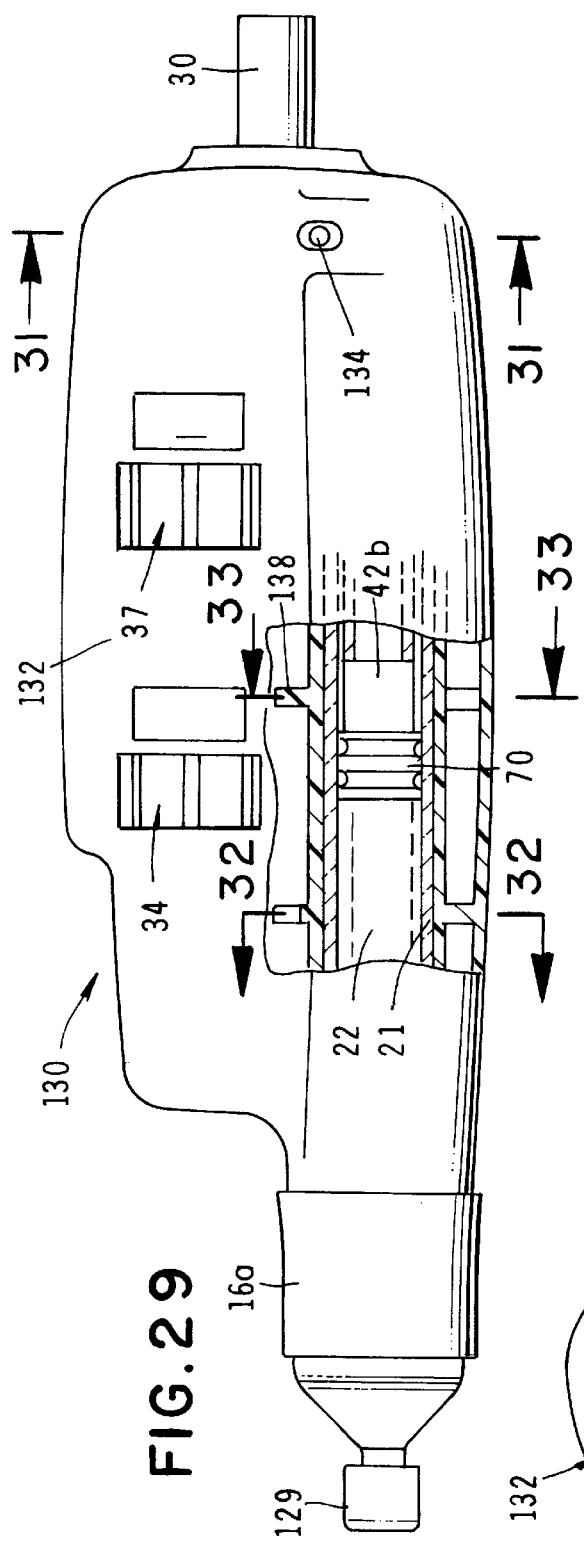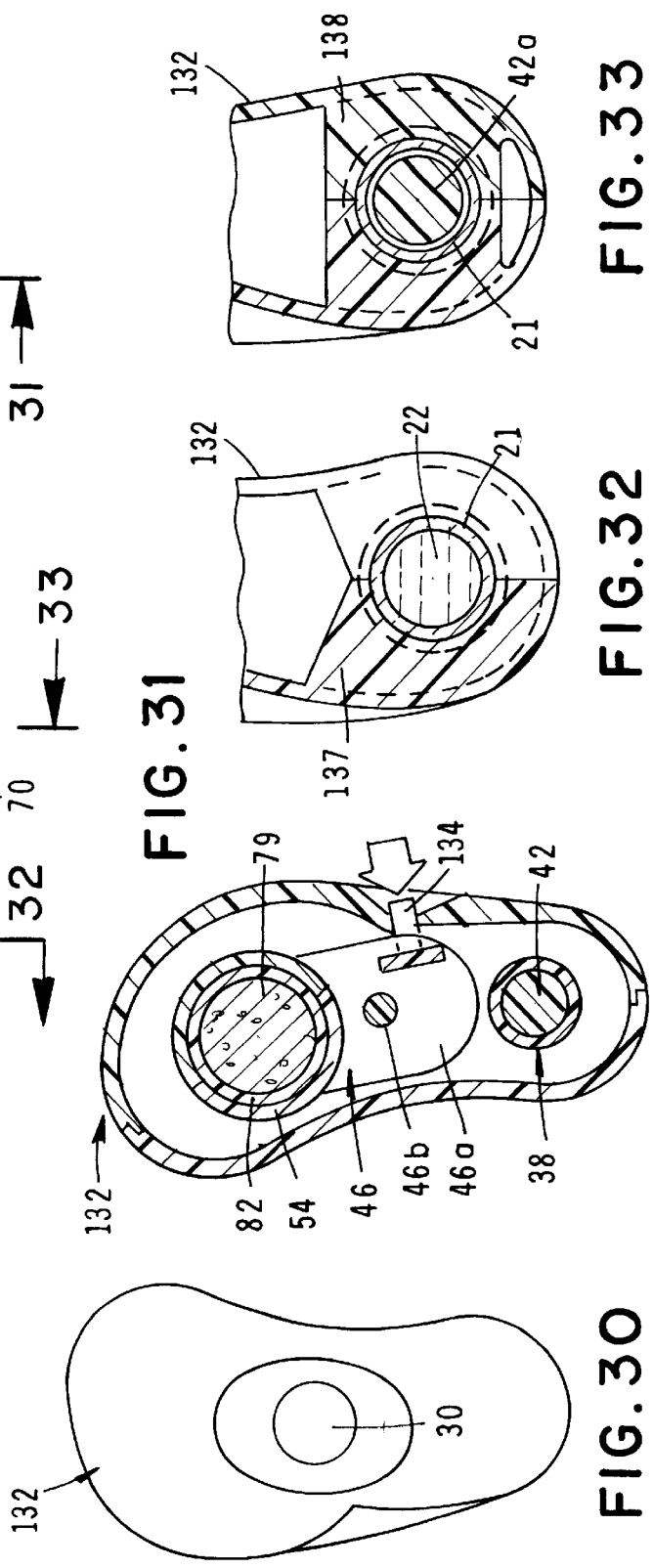

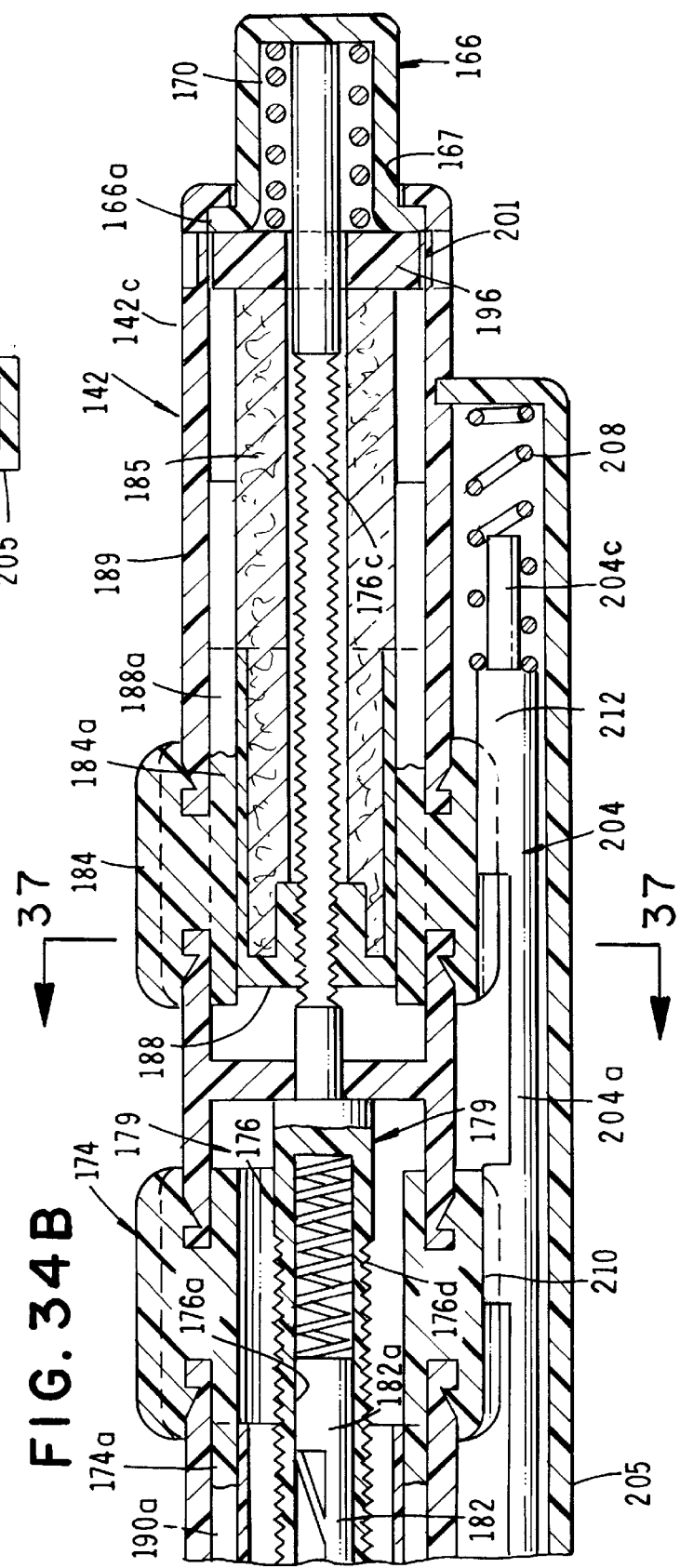

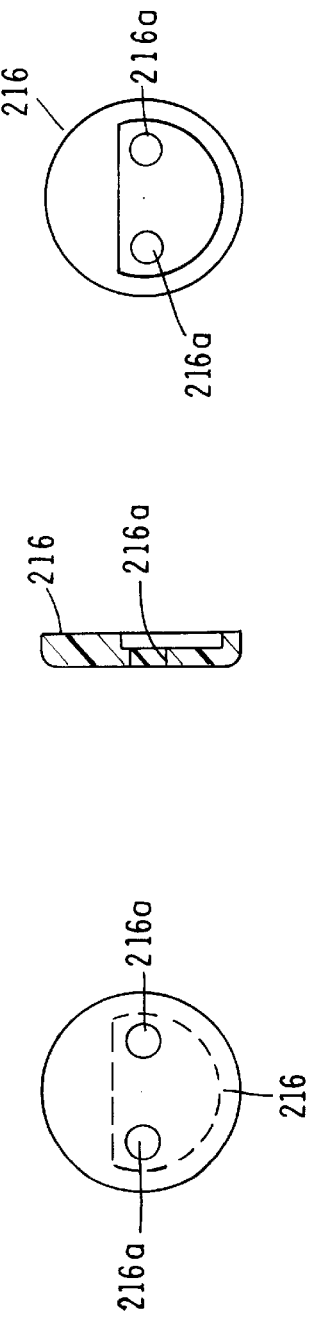
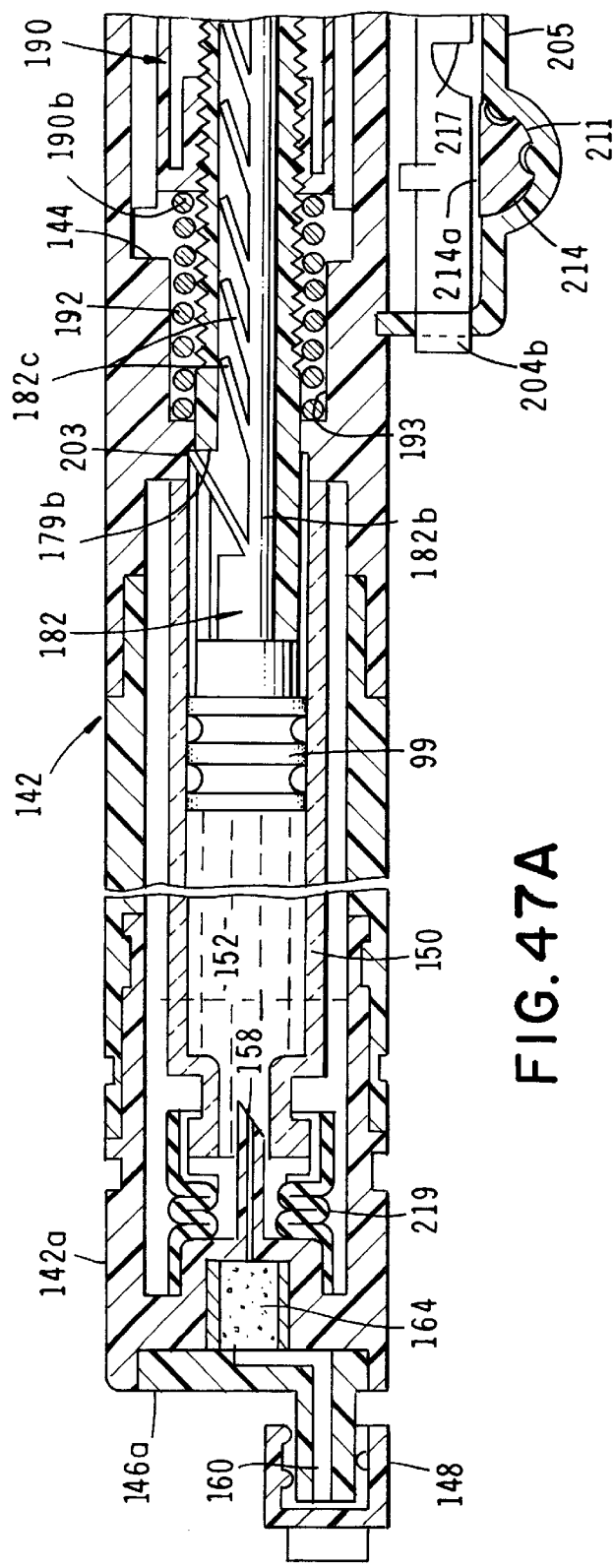
FIG. 41
FIG. 42
FIG. 43
FIG. 47A

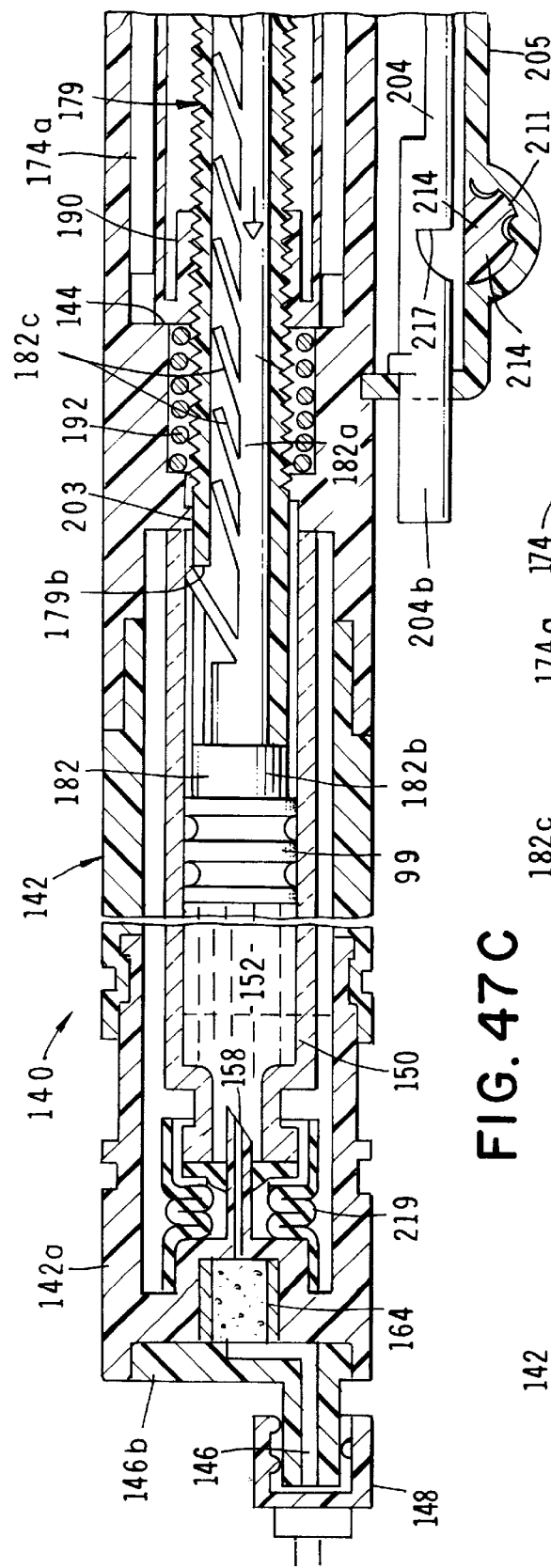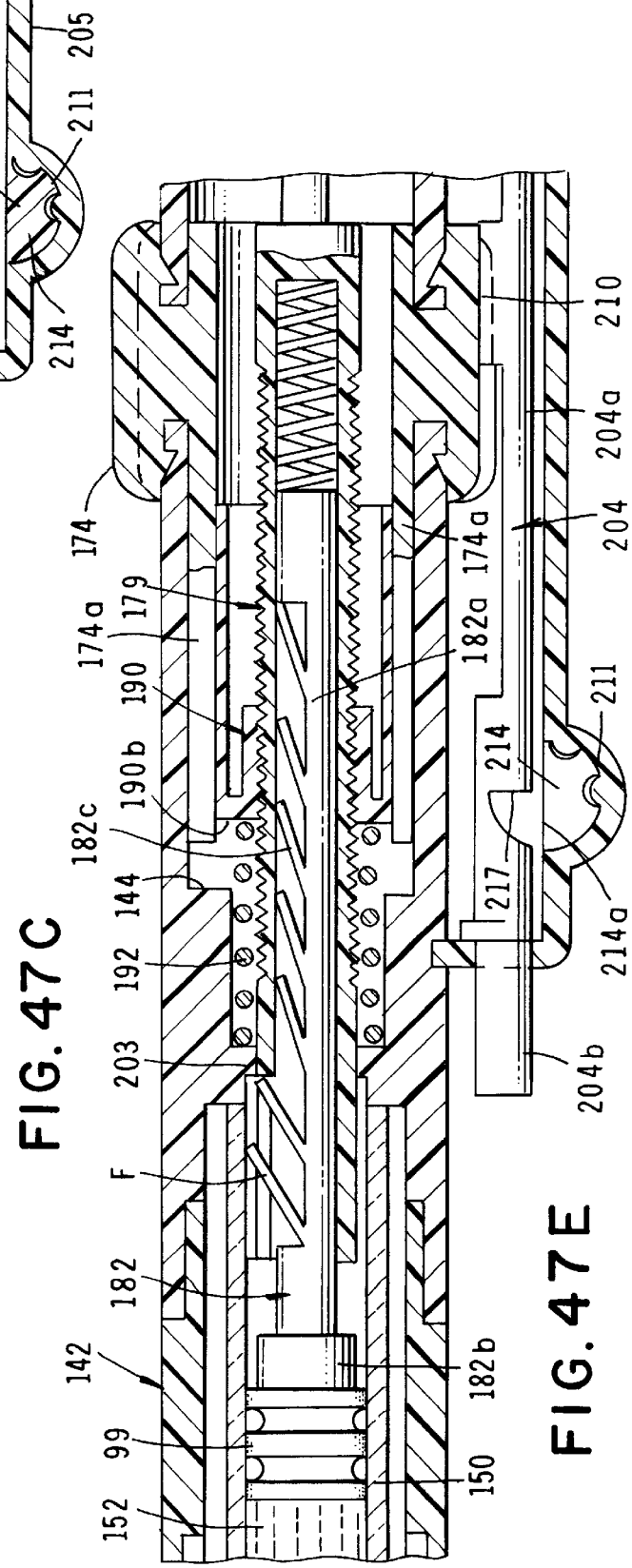
FIG. 47C
FIG. 47E

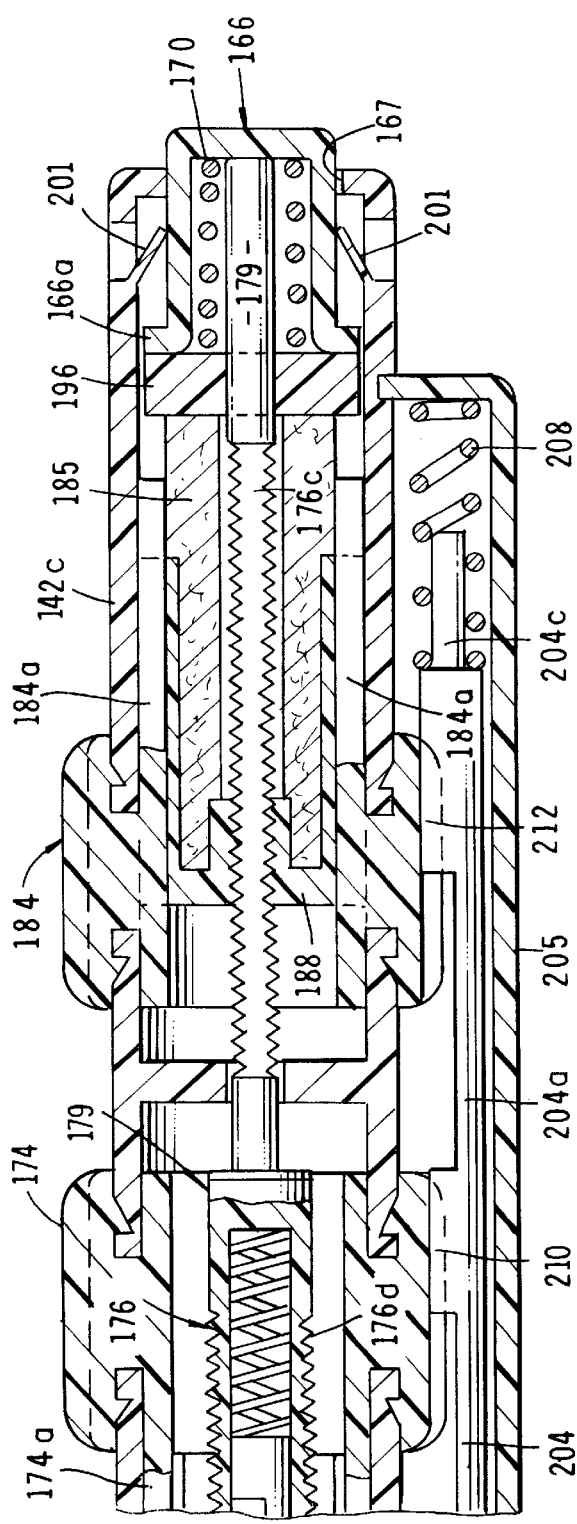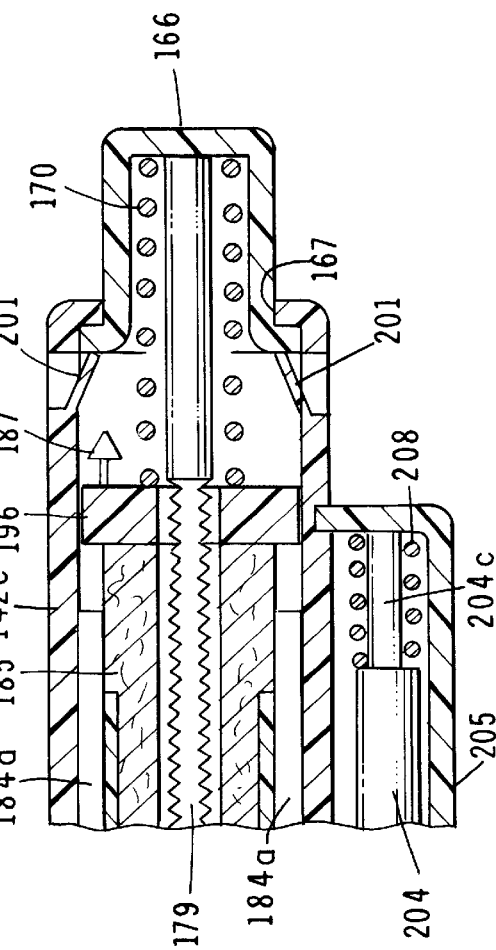
FIG. 47D
FIG. 48

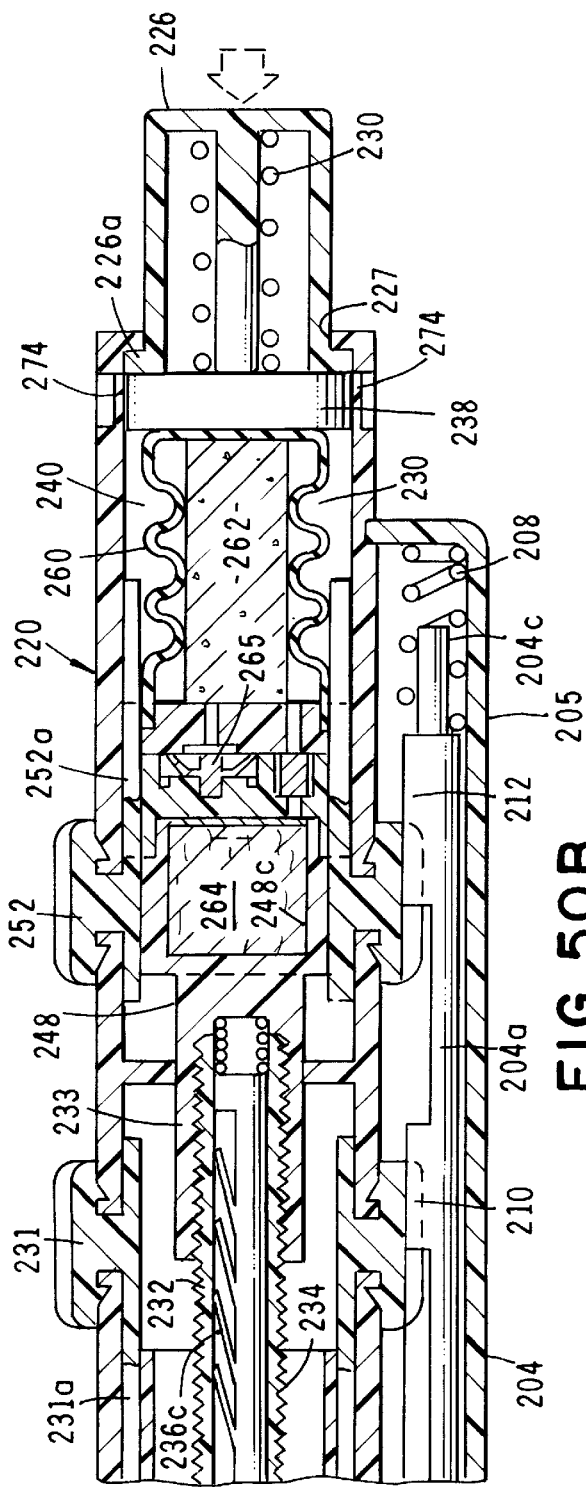
FIG. 50B
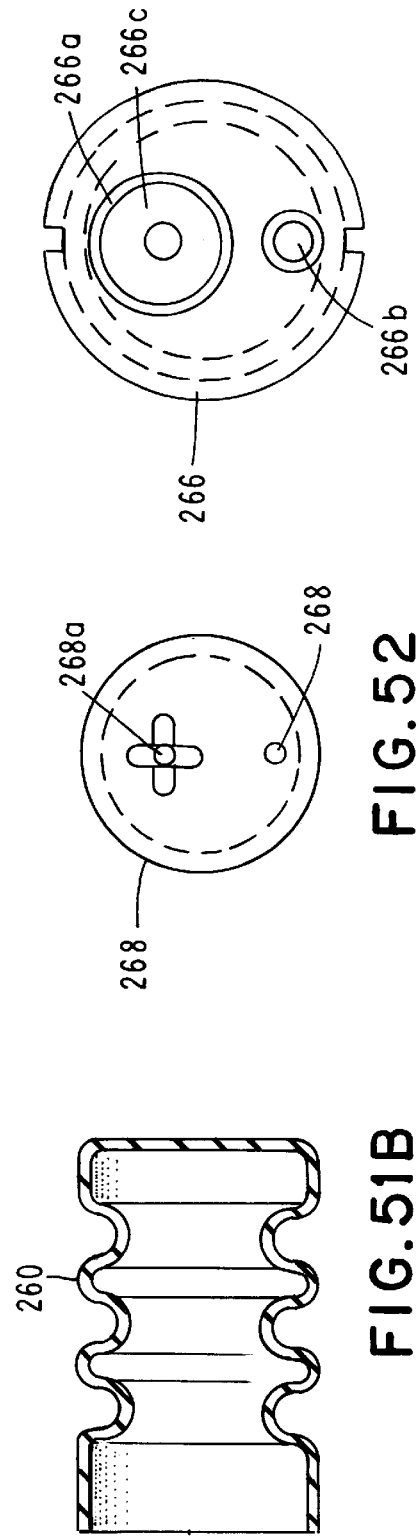
FIG. 53
FIG. 52
FIG. 51B

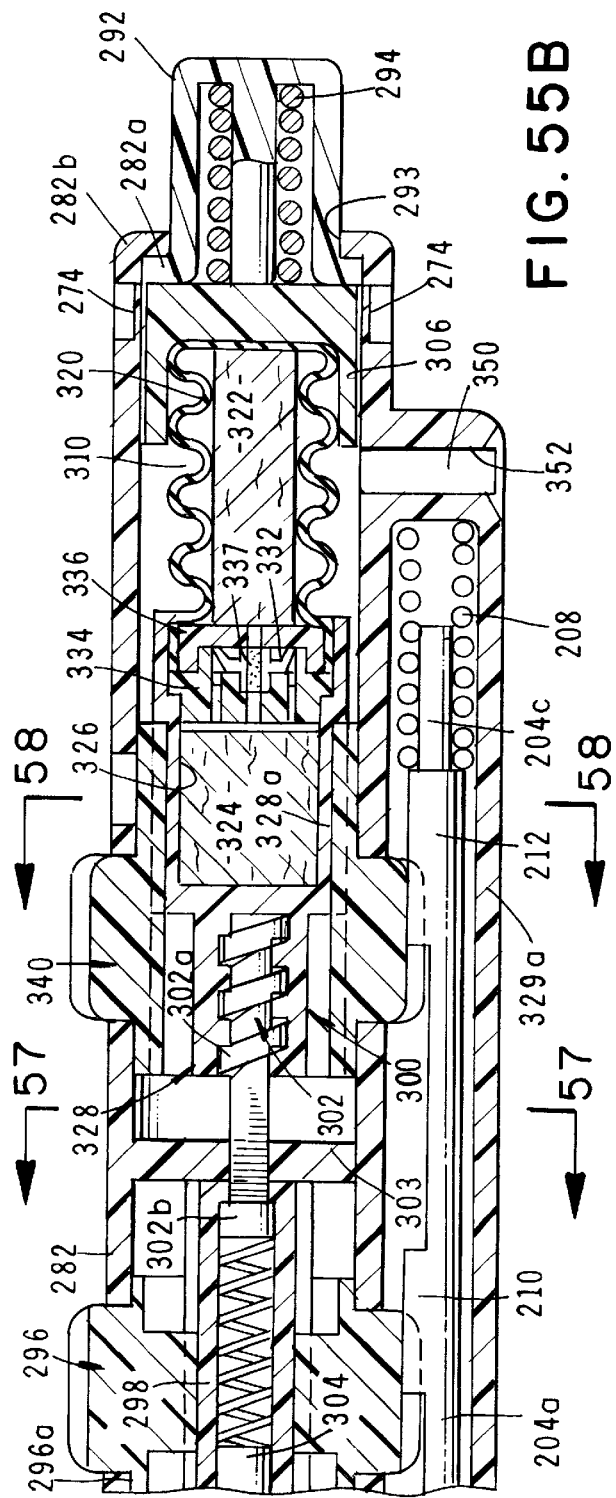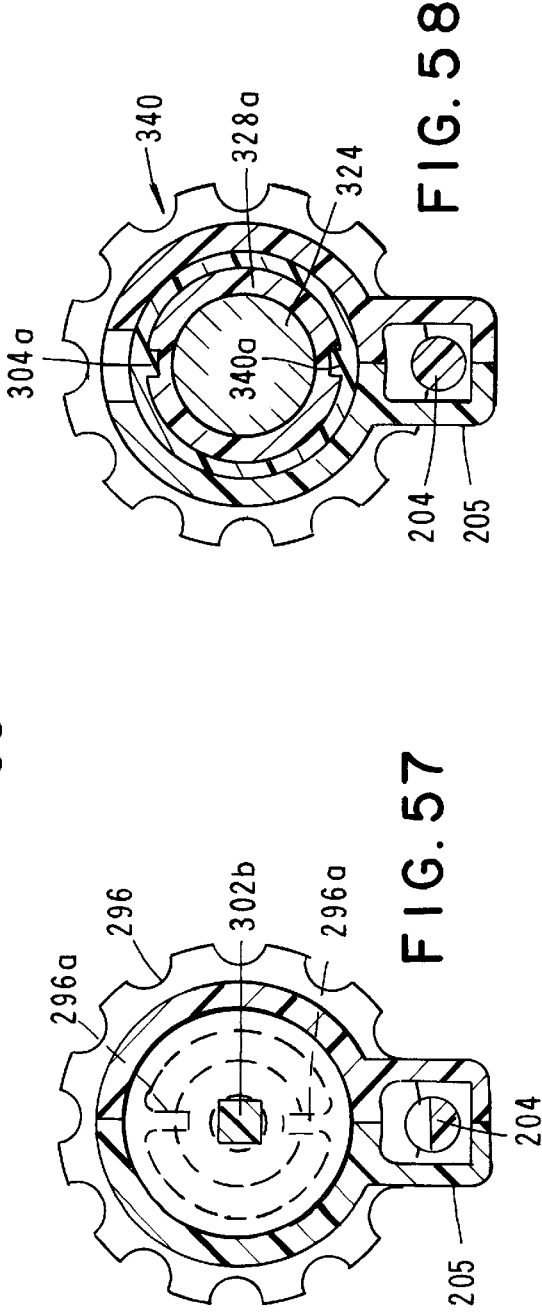

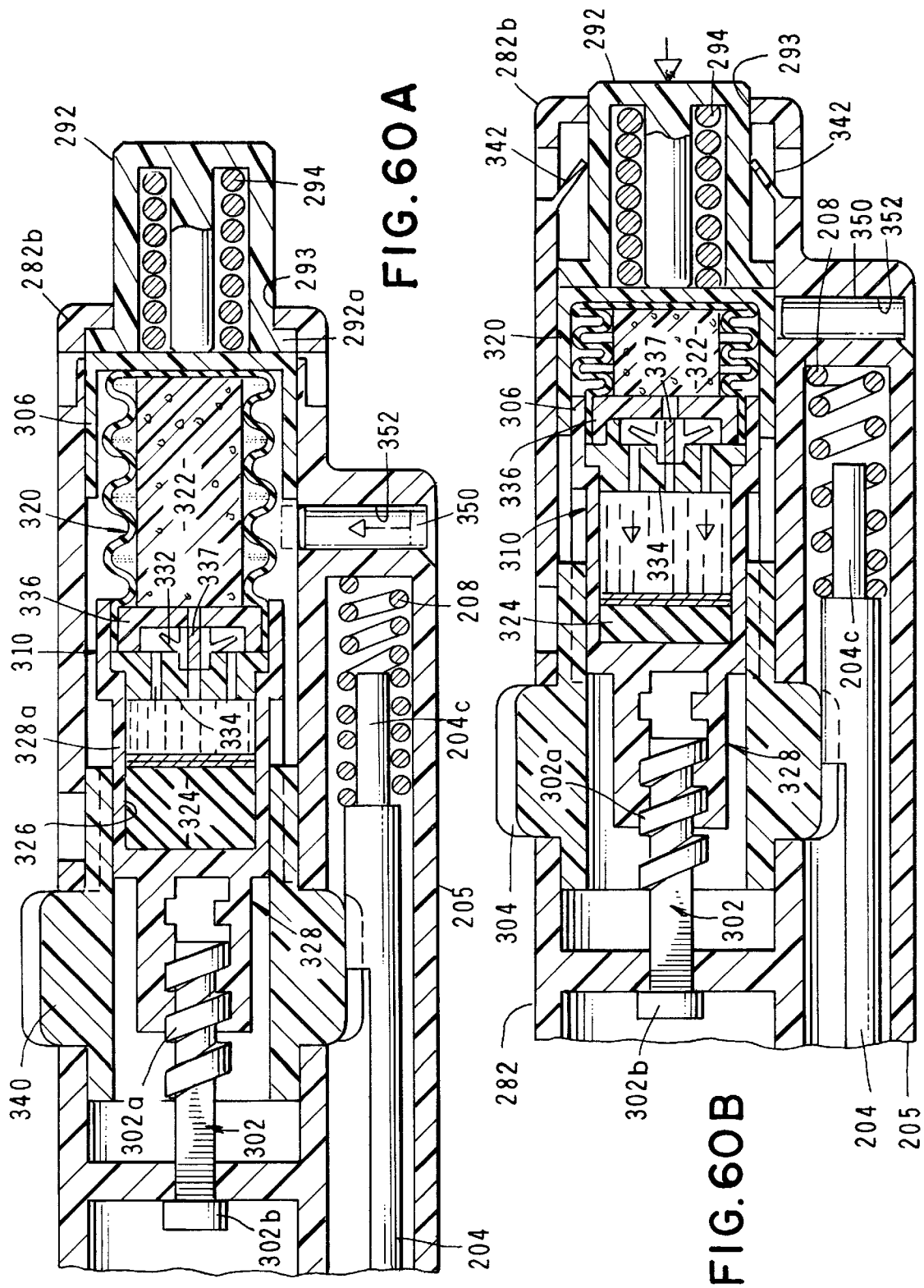

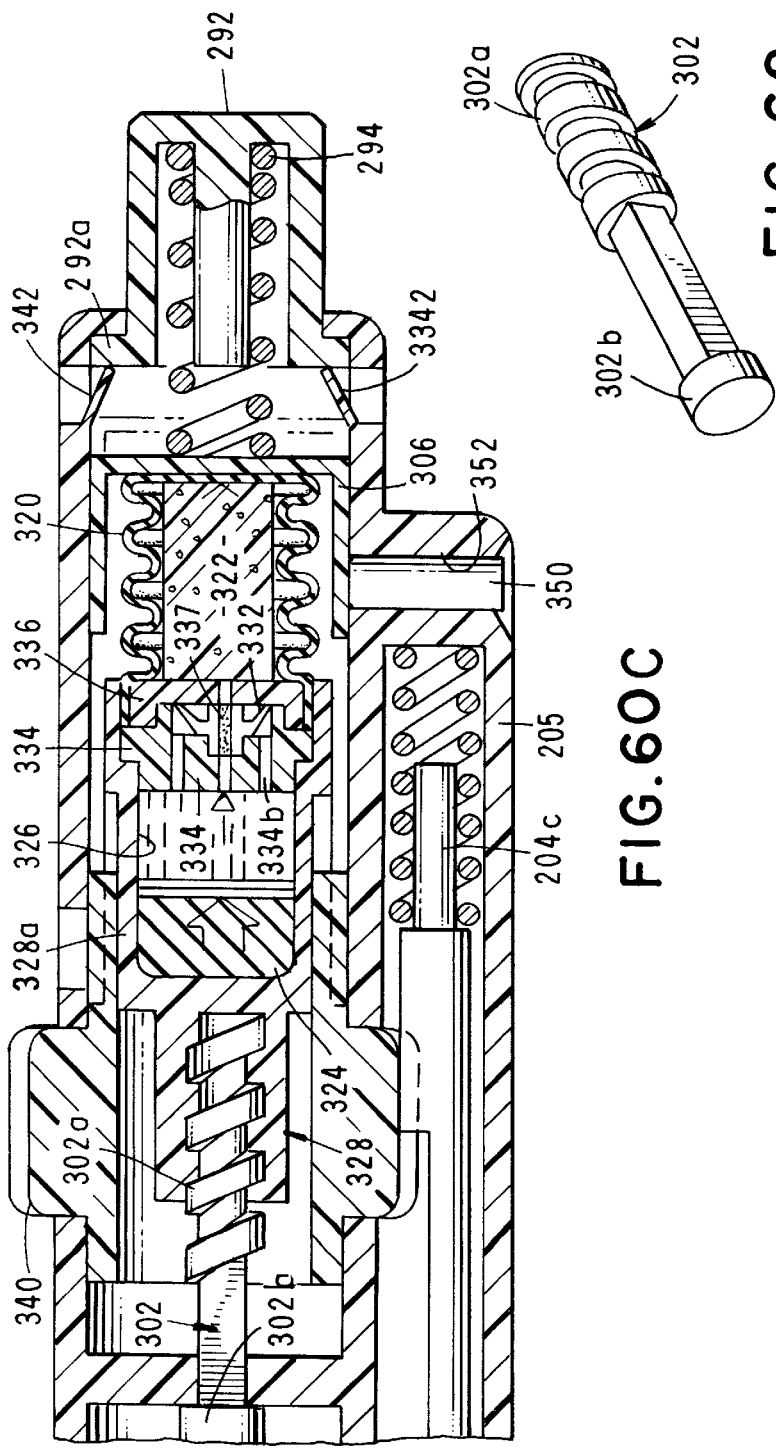
FIG. 60C
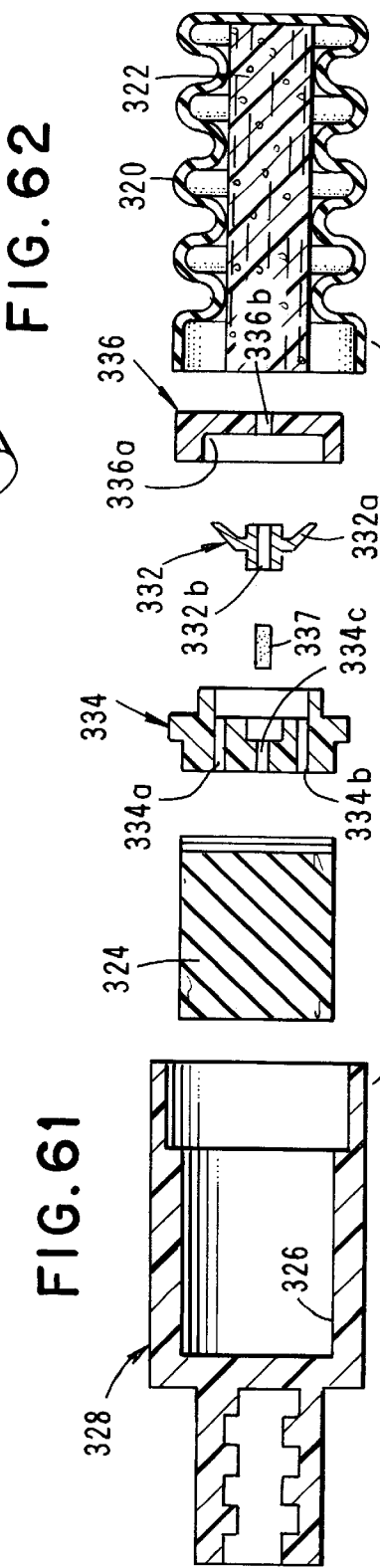
FIG. 62
FIG. 61

PATIENT CONTROLLED FLUID DELIVERY DEVICE

BACKGROUND OF THE INVENTION

1. Field of the Invention

The present invention relates generally to fluid medicament dispensers. More particularly, the invention concerns a novel patient controlled fluid dispenser for use in sequentially dispensing doses of a liquid medicament of predetermined volume at predetermined intervals.

2. Discussion of the Prior Art

In recent years considerable research has been directed toward the development of an apparatus that enables patients to safely administer doses of intravenous medication at will without the need for constant supervision by medical staff. In this connection, as early as the 1960s researchers began testing an apparatus that would allow patients to self-administer doses of opioid drugs when they felt the need for them. The early patient controlled analgesia (PCA) devices typically comprised electromechanical devices such as electronically controlled infusion pumps which were connected to a timing device. In using these devices, when the patients experienced pain, they triggered the device by depressing a button located at the end of a cord extending from the machine. The machine then delivered a preset amount of an analgesia drug into the patients in-dwelling IV catheter. A timer was programmed to preclude administration of additional doses until a specific interval of time had elapsed, a so-called lockout or delay interval. The purpose of the lockout interval was to prevent the patient from administering a second dose until after the first dose had time to exert its maximal effect.

In addition to the early electromechanical type prior art devices, a number of mechanical devices were also proposed. These mechanical devices usually prevented overdosing through the use of a flow restrictor of some kind so that, even if the patient were to actuate the apparatus repeatedly at short intervals, the restrictor would prevent the safe overall dose level from being exceeded. Accordingly, such devices permitted the patient to administer low doses of medication at frequent intervals and, therefore, was an almost continuous administration of drugs. With some medication, this can be an advantage, with other medications, it can create significant problems. With medications, such as analgesia, it is preferable that the doses be less frequent and in larger volumes.

Even using the somewhat primitive early prior art PCA devices, it was clearly established that the effectiveness of the administration of analgesia is significantly enhanced when the medicine used can be controlled by the patient, rather than being administered by a standard procedure involving a caregiver each time the medicament is needed. The enhancement is manifested in several ways, including improvements to the patient's comfort, minimization of any adverse side effects related to the amount of medication used and minimizing the time required by nurses and other care givers. Additionally, with patient controlled administration, experience has shown considerably less medicine is required to achieve the specific levels of pain relief desired.

In recent years PCA has been used widely to improve the quality of postoperative pain management. The PCA approach advantageously allows the patient to take as much analgesic as necessary to achieve satisfactory relief of pain, thus overcoming variation among individuals in analgesic requirements. It also avoids problems of administration of analgesia caused by staff shortages in hospital wards. Additionally, a rational use of a PCA-infusion device allows the individual patient to overcome variations in pharmacokinetic and pharmacodynamic factors by titrating the rate of narcotic administration to meet their analgesic needs. If recurrent nausea or vomiting develops after bolus injections, the patient can be switched to a different narcotic analgesic or the PCA therapy can be discontinued.

PCA therapy is ideally suited for certain types of treatment where pain is intermittent. For example, patients with chronic cancer pain often have periods in which there is minimal discomfort and, during that time, analgesia is not required. Therefore, a patient may use less total drug than if administered by continuous infusion. Second, continuous intravenous morphine infusion results in narcotic tolerance, necessitating dose escalations to provide consistent pain relief Because less narcotic may be given by patient-controlled analgesia, the development of tolerance may prove to be less than that produced by continuous intravenous morphine infusions.

Exemplary of the prior art electromechanical type devices for infusing analgesia and like medications to a patient on demand is the apparatus disclosed in U.S. Pat. No. 5,069,668 issued to Boyd. One form of mechanical type, patient controlled analgesia infusion apparatus is described in U.S. Pat. No. 5,135,491 issued to Baldwin. This latter patent discloses an apparatus in which the liquid to be self administered by the patient is controllably supplied from a positively pressurized supply reservoir to a lower pressure dose chamber of a patient operable syringe from which the patient may expel the liquid to be used into a suitable infusion site such as an in-dwelling cannula. The supply of liquid from the reservoir into the dose chamber is controlled by a flow control metering tube assembly which provides a selected flow rate for a reference of fluid and a reference of pressure differential.

Exemplary of another type of prior art mechanical PCA apparatus is the apparatus disclosed in U.S. Pat. No. 4,828,551 issued to Gertber et al. This apparatus, which is mechanical/hydraulic in nature, comprises a reservoir and a pump operable by the patient for dispensing medicine from the reservoir into the patient's IV system in incremental doses. The pump capacity per stroke may be adjustable, thereby adjusting the size of each dose dispensed. Timing apparatus assures that a specific interval of time must pass between sequential dosage dispensations.

The thrust of the present invention is to provide a vastly improved, compact, readily portable and easy-to-use, patient-controlled fluid dispenser for use in controllably dispensing fluid medication at a selected uniform rate. More particularly, a primary object of the invention is to provide a device of such a character which is of an all mechanical construction that is ideally suited for patient administration of pain killing drugs in a home environment. The devices of the invention are uniquely configured so that the treating physician can preset the volume of each of the multiple doses to be self-administered by the patient and can also preset, and precisely control the intervals at which the doses can be given.

SUMMARY OF THE INVENTION

It is an object of the present invention to provide a compact, readily portable, easy-to-use, patient-controlled fluid dispenser for use in controllably dispensing fluid medicament at a selected uniform rate. More particularly, it is an object of the invention to provide a device of the aforementioned character which is of an all mechanical construction and is ideally suited for patient administration of pain killing drugs in the home environment.

Another object of the invention is to provide a patient controlled analgesia device in which the intervals at which a selected drug can be administered, as well as the volume of the dose of drugs to be administered, can be preset by the treating physician and once set cannot be altered by the patient.

Another object of the invention is to provide a patient controlled analgesia device of the character described in the preceding paragraphs which includes a novel key-controlled mechanism that positively prevents unauthorized changes in the preset interval and preset volume control mechanisms of the apparatus. More particularly, in one form of the apparatus of the invention the device cannot be operated without a physician-controlled operating key which functions to enable and disable the volume and interval setting mechanisms of the device.

Another object of the invention is to provide a device of the character described which includes a disabling mechanism that totally disables the device and renders it inoperable.

Another object of the invention is to provide a self-contained, patient controlled analgesia device which is of a very simple construction and yet is extremely reliable in use.

Another object of the invention is to provide a patient controlled analgesia device as described in the preceding paragraphs which is easy to use with a minimum of training and is inexpensive to manufacture in large quantities.

In summary, the present invention concerns a novel patient controlled device for the sequential delivery of selectable doses of fluid to a delivery site which includes a housing having an internal stop and a fluid outlet in communication with the delivery site. Disposed internally of the housing is a fluid reservoir for containing the fluid to be delivered, the fluid reservoir having an outlet in communication with said fluid outlet of the housing. Mounted on the housing is dispensing means for sequentially dispensing first and second doses of fluid from the outlet of the fluid reservoir. Operating means, which are operably associated with the dispensing means for controlling the dispensing of fluid therefrom, include two novel cooperating control means, namely, dose interval control means for controlling of the interval of time between the dispensing of said first and second doses; and dose volume control means for controlling of the volume of said first and second doses.

BRIEF DESCRIPTION OF THE DRAWINGS

FIGS. 4A and 4B, when considered together, comprise a generally perspective, exploded view of the device of the invention showing the arrangement of the various component parts thereof.

FIG. 5 is a greatly enlarged exploded perspective view of the adjustable dose interval timing means of the device for controlling the intervals of administration of the medicament apparatus shown in FIG. 1.

FIGS. 6A and 6B, when considered together, comprise an enlarged cross-sectional view taken along lines 6—6 of FIG. 3.

FIG. 9 is a cross-sectional view taken along lines 9—9 of FIG. 8.

FIG. 11 is an enlarged, fragmentary cross-sectional view of the adjustable dose interval timing means of the apparatus of the invention.

FIG. 12 is a view taken along lines 12—12 of FIG. 11.

FIG. 13 is a cross-sectional view taken along lines 13—13 of FIG. 6B.

FIG. 14 is a cross-sectional view taken along lines 14—14 of FIGS. 6A and 6B.

FIG. 15 is an enlarged, cross-sectional view taken along lines 15—15 of FIG. 14.

FIG. 15A is a fragmentary, generally perspective view of a portion of the dispensing and operating means of the invention.

FIG. 16 is a fragmentary, cross-sectional view of an alternate form of the infusion means of the apparatus of the invention.

FIG. 17 is a generally diagrammatic view illustrating the first step in the operation of the apparatus of the invention, namely, removing the protective tear-away strip which surrounds the forward portion of the hand-held apparatus of the invention and functions to protect the infusion means thereof.

FIG. 17A is a fragmentary view similar to FIG. 17 showing the tear-away strip having been removed.

FIG. 18 is an enlarged, side-elevational view of one form of the physician's operating key of the apparatus.

FIG. 19 is a view taken along lines 19—19 of FIG. 16.

FIGS. 25A and 25B, when considered together, comprise an enlarged, cross-sectional view similar to FIGS. 24A and 24B, but showing the position of the various components of the device after the dispensing member has been pushed inwardly by the patient.

FIG. 25C is a greatly enlarged, fragmentary, cross-sectional view of the dose interval control means illustrating compression of the fluid containing cellular mass of the means and showing the fluid flow therefrom in a direction toward the yieldably compressible cellular mass.

FIGS. 26A and 26B, when considered together, comprise a cross-sectional view similar to FIGS. 25A and 25B, but showing the position of the various components of the device after the dispensing member has been pushed inwardly by the patient and then released permitting it, along with the operating rod assembly, to return to its starting position.

FIG. 26C is a greatly enlarged, fragmentary, cross-sectional view of the dose interval control means of the apparatus of the invention similar to FIG. 25C, but showing fluid flow in an opposite direction toward the fluid containing cellular mass via the rate control frit of the device.

FIG. 29 is a side-elevational view of an alternate form of apparatus of the invention.

FIG. 30 is a rear view of the device.

FIG. 31 is a cross-sectional view taken along lines 31—31 of FIG. 29.

FIG. 32 is a cross-sectional view taken along lines 32—32 of FIG. 29.

FIG. 33 is a cross-sectional view taken along lines 33—33 of FIG. 29.

FIGS. 34A and 34B, when considered together comprise a side-elevational, cross-sectional view of the embodiment shown in FIG. 34.

FIG. 35 is a cross-sectional view taken along lines 35—35 of FIG. 34A.

FIG. 36 is a cross-sectional view taken along lines 36—36 of FIG. 34A.

FIG. 41 is a front view of the physician key engaging cap of the locking means of the invention.

FIG. 42 is a side-elevational view of the cap shown in FIG. 41.

FIG. 43 is a rear view of the cap shown in FIG. 41.

FIGS. 47A and 47B, when considered together, comprise a side-elevational, cross-sectional view similar to FIGS. 34A and 34B but showing the appearance of the device following setting of the dose volume control means and the dose internal control means.

FIGS. 47C and 47D, when considered together, comprise a side-elevational, cross-sectional view similar to FIGS. 47A and 47B, but illustrating the fluid dispensing step and showing the delivery member telescopically inserted into the housing.

FIG. 47E is a fragmentary, side-elevational, cross-sectional view showing the return movement of the operating rod assembly following release of the dispensing member.

FIG. 48 is a fragmentary, side-elevational, cross-sectional view similar to FIG. 47D, but showing the delivery member returned to an extended, locked position relative to the housing.

FIGS. 50A and 50B, when considered together, comprise a side-elevational, cross-sectional view of an alternate form of patient controlled administration device of the invention.

FIGS. 51A and 51B, when considered together, comprise is a cross-sectional exploded view of the dose volume and dose interval control means of the apparatus shown in FIGS. 50A and 50B.

FIG. 52 is a view taken along lines 52—52 of FIG. 51 A.

FIG. 53 is a view taken along lines 53—53 of FIG. 51 A.

FIGS. 55A and 55B, when considered together, comprise a side-elevational, cross-sectional view of still another embodiment of the patient controlled administration apparatus of the present invention.

FIG. 57 is a cross-sectional view taken along lines 57—57 of FIG. 55B.

FIG. 58 is a cross-sectional views taken along lines 58—58 of FIG. 55B.

FIG. 60A is a fragmentary, side-elevational view of the volume and interval control means of the invention illustrating the means in a starting configuration.

FIG. 60B is a fragmentary, side-elevation view similar to FIG. 60A but showing the dispensing member having been pushed inwardly of the housing.

FIG. 60C is a fragmentary, side-elevational view similar to FIG. 60B but showing the dispensing member returned to its starting, locked configuration and the does interval control means moving toward its starting configuration.

FIG. 61 is an exploded, side-elevational, cross-sectional view of the volume and dose interval control means of the invention as shown in FIG. 60.

FIG. 62 is a generally perspective view of the coupling shaft of the apparatus which couples the operating shaft with the dose volume and dose interval control means.

DISCUSSION OF THE INVENTION

Figures 1, 2, 3:
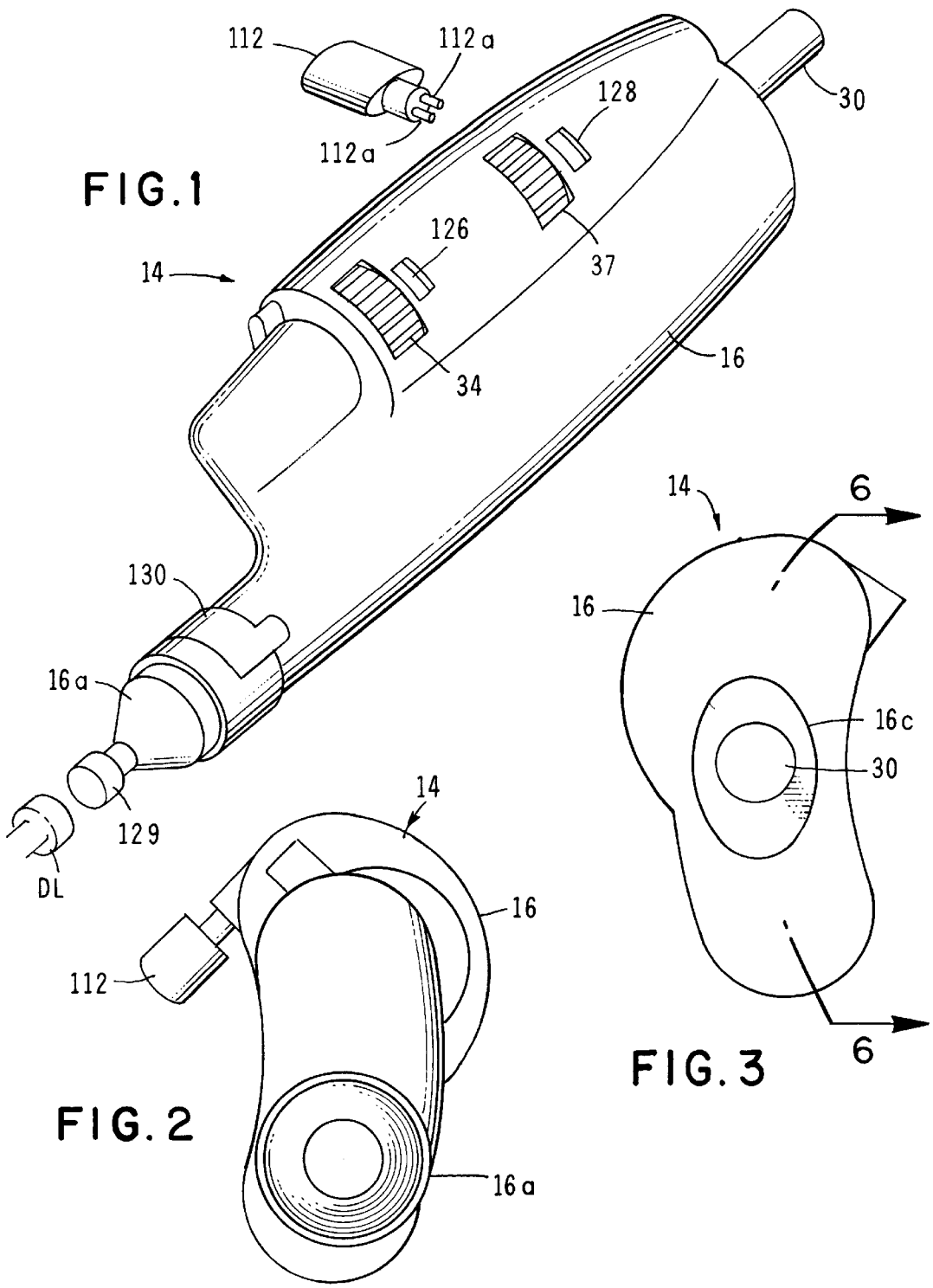
FIG. 1 is a generally perspective view of one form of the patient controlled analgesia device of the present invention.
FIG. 2 is a front view of the device shown in FIG. 1.
FIG. 3 is a rear view of the device.

Referring to the drawings and particularly to FIGS. 1 through 6, one form of the patient control infusion device of the present invention is there illustrated and generally designated by the numeral 14. In this form of the invention, the device comprises a hollow device housing 16 having a stop 18 and a fluid outlet 20 (FIG. 6A) which can be placed in fluid communication with a remote delivery site via a delivery line "DL" (FIG. 1). Disposed within housing 16 is a fluid container 21 having a fluid reservoir 22 for containing the fluid to be delivered (FIG. 6A). Fluid reservoir 22 has an outlet 24 which is in fluid communication with the fluid outlet 20 of device housing 16 via a closure means, here comprising a pierceable septum 26. Septum 26 is held in position on container 21 by a crimp ring 21c and is pierceable by a hollow cannula 28 which is mounted within a forward portion 16a of device housing 16. Forward portion 16a of the housing is threadably connected to a forward, neck-like portion 16b of the housing and is movable from a first starting position shown in FIG. 6A, wherein cannula 28 is spaced apart from septum 26, into a second operating position shown in FIG. 25A wherein cannula 28 has penetrated septum 26. With the forward portion of the housing in the operating position shown in FIG. 25A, reservoir 22 is placed in fluid communication with outlet 20 of the housing.

Manually operated dispensing means are connected to device housing 16 proximate the rearward portion 16c thereof. The dispensing means functions to sequentially dispense discrete doses of fluid from outlet 24 of fluid reservoir 22. As best seen in FIG. 6B, the dispensing means here comprises a generally cylindrically, shaped hollow dispensing member 30 which is telescopically receivable within an opening 32 provided in the rearward portion 16c of housing 16. Disposed within member 30 is a first biasing means, shown here as a coil spring 31, which yieldably resists inward movement of member 30.

Connected to the dispensing means is the important operating and control means of the invention, which functions to control the sequential dispensing of the discrete doses of fluid from reservoir 22. This important operating means comprises two major control means, namely a dose interval control means for controlling the interval of time between the dispensing of each discrete dose of medication and a dose volume control means for controlling the volume of each discrete dose of medication to be delivered.

The dose volume control means of the present form of the invention includes a manually adjustable dose volume control member 34 which is rotatably mounted within device housing 16 and is rotatable by the treating physician or health care worker to preset the volume of the discrete doses to be delivered to the patient.

Figure 4A:
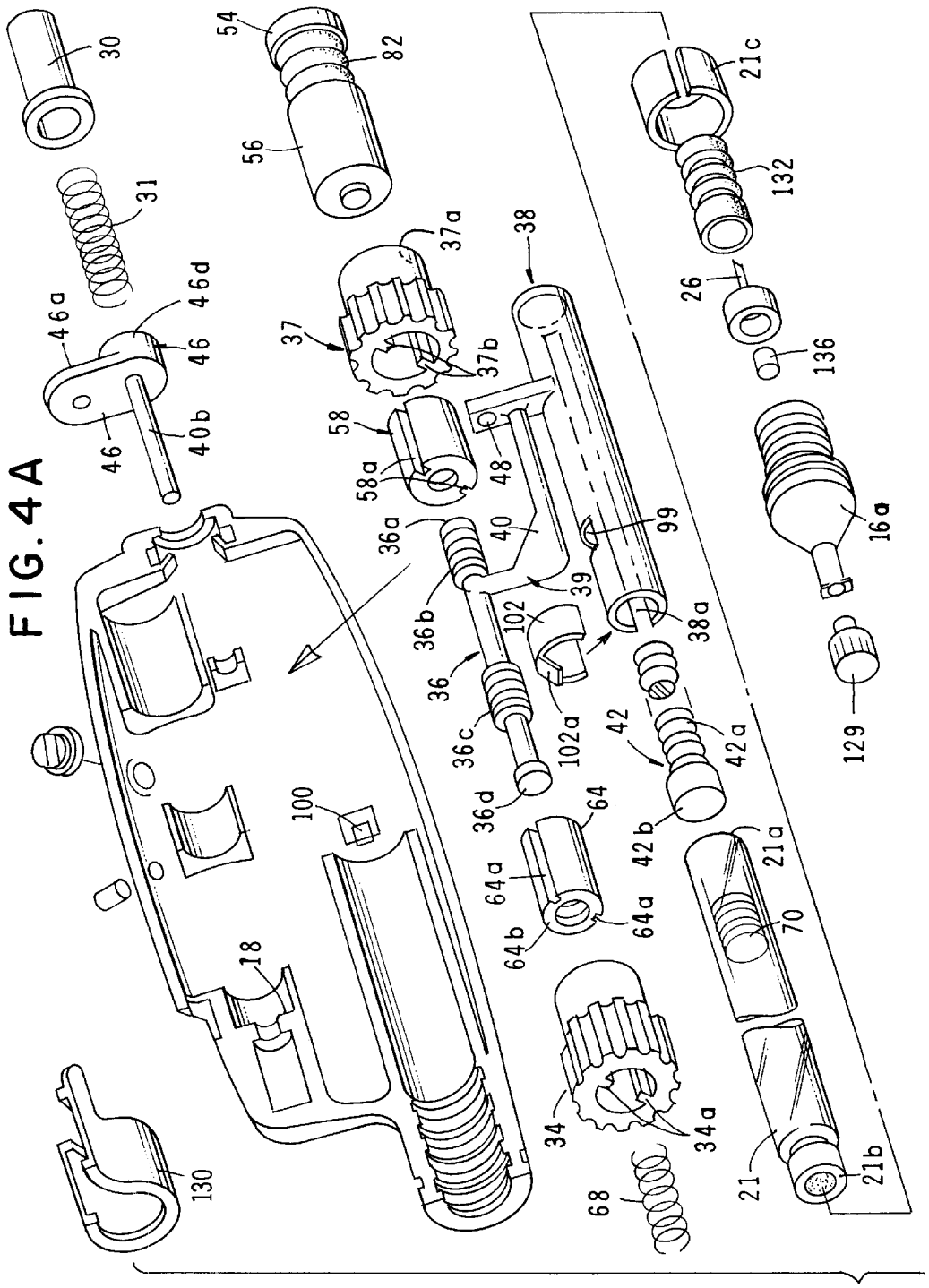
Figure 6A:
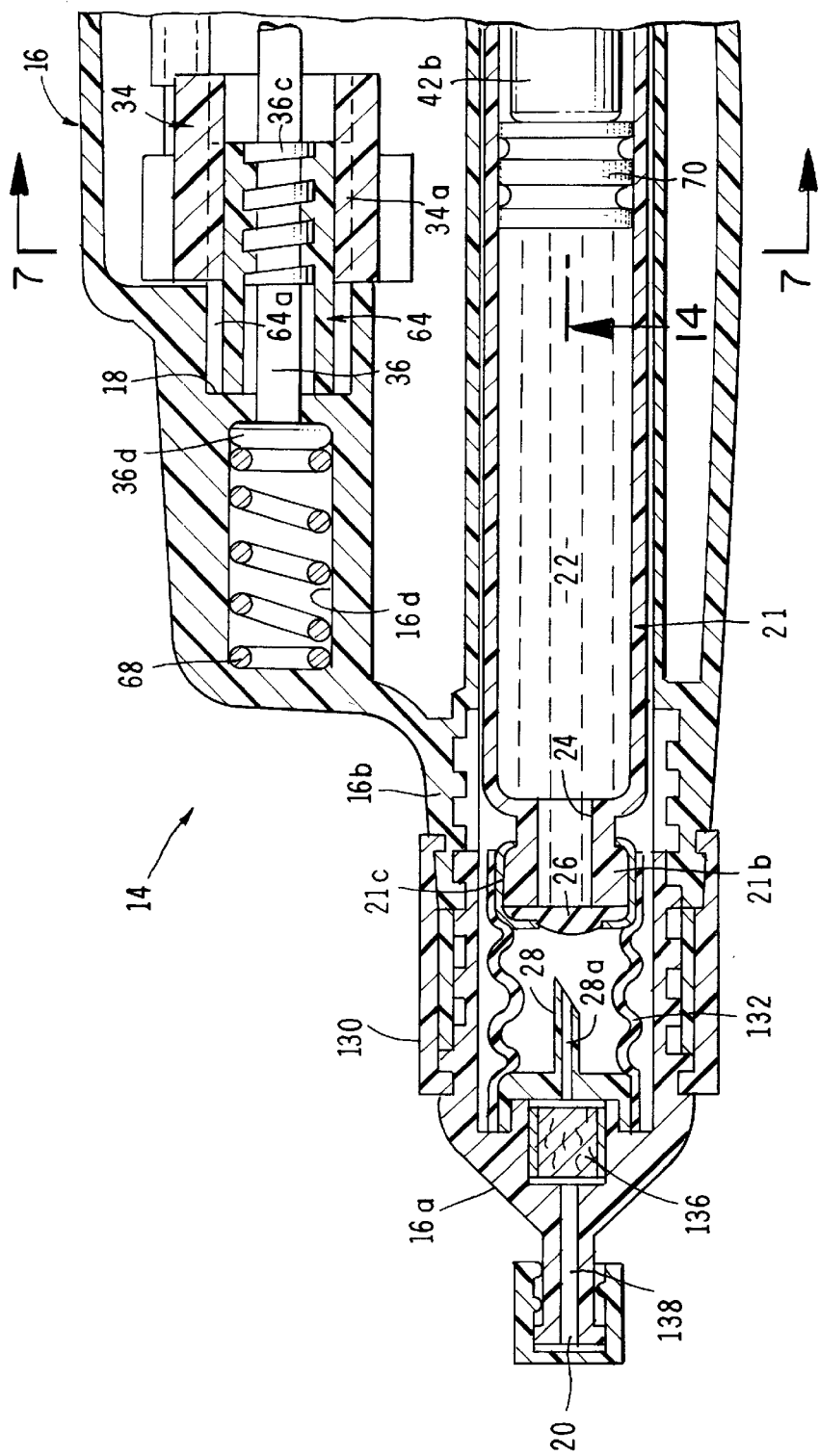
Figure 7:
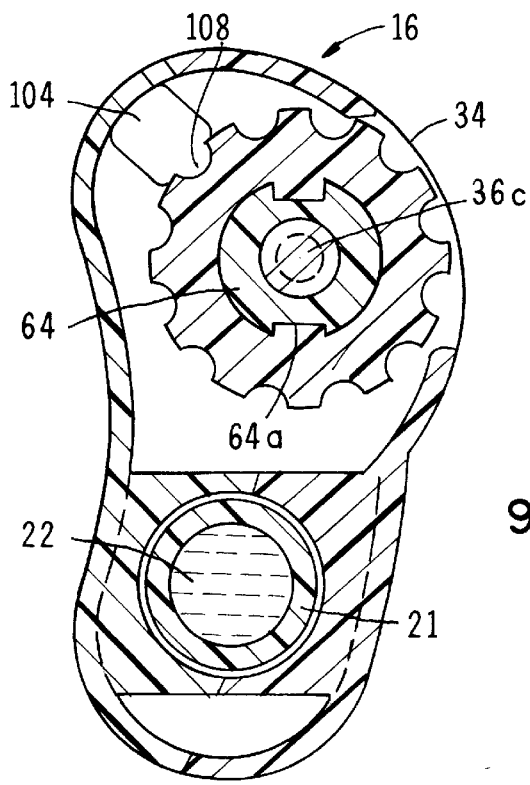
FIG. 7 is a cross-sectional view taken along lines 7—7 of FIG. 6A.

Member 34 is carried by an operating rod 36 which forms a part of an operating rod assembly generally designated in the drawings by the numeral 39. Operating rod assembly 39 also includes an elongated tube-like member 38, the purpose of which will presently be described (FIGS. 4A, 6A and 6B). Tube-like member 38 is interconnected with operating rod 36 by a generally "J" shaped connector segment 40. A dose interval control member 37, which forms a part of the dose interval control means of the invention, is also carried by operating rod 36 and, in a manner presently described, is rotatable by the treating physician or health care worker to preset the intervals at which doses of medicaments can be delivered by the patient.

As best seen by referring to FIGS. 4A and 6B, a dosing rod 42 having a stepped shank portion 42a and head portion 42b is telescopically movable within tube-like member 38. Dosing rod 42, which forms a part of the dispensing means of the invention is connected to dispensing member 30 by means of dispensing rod assembly 39 and causes fluid to flow outwardly from reservoir 22 of chamber 21 when the dispensing member of the dispensing means is pushed inwardly relative to housing 16 in the manner shown in FIG. 25B. Interconnecting dispensing member 30 with operating rod assembly 39, is a connector assembly 46 which comprises a head portion 46a and an elongated shaft portion 46b which extends therefrom. As best seen in FIG. 6B, in the starting position of the device, dispensing member 30 is disposed in engagement with head portion 46a of the connector assembly while shaft portion 46b extends through a drilled bore 48 provided in J-shaped connector 40 and is adapted to move telescopically through the drilled bore 48 during operation of the device. Shaft portion 46b also extends through a shaft support and guide member 50 which forms a part of device housing 16 and functions to support portion 46b and guide its travel as it moves telescopically through bore 48 between a first position shown in FIG. 6B to the second, inward position shown in FIG. 25B.

Considering next the important dose interval control means of the invention, it is to be observed that an upwardly extending finger-like portion 46c of connector assembly 46 engages a hollow housing 54 which is disposed within an internal chamber 16c of housing 16 and comprises a part of the dose interval control means. A second hollow housing 56, which also forms a part of the dose interval control means is spaced apart from housing 54 and is interconnected with rearward extremity 36a of operating rod 36. Housing 56 is disposed within an internal chamber 37a formed in control member 37 in the manner best seen in FIG. 9. As will be described in greater detail hereinafter, an inward force exerted by the patient on dispensing member 30 will cause a forward, or inward movement, of the entire operating rod assembly 39 from the initial starting position shown in FIG. 6B to the first operating position shown in FIG. 25B. This inward movement of operating rod assembly 39 causes concomitant forward movement of dosing rod 42 as well as forward movement of certain portions of the dose interval control means.

Referring particularly to FIGS. 4A, 6A and 6B, it can be seen that operating rod 36 includes first and second threaded segments 36b and 36c respectively. Threadably interconnected with threaded segment 36b is a dose interval adjustment swivel 58 to which dose interval control member 37 is interconnected by means of oppositely disposed splines 37b which are formed on member 37 and which are slidably receivable within oppositely disposed grooves 58a provided in swivel 58 (FIG. 4A).

Considering next the dose volume control means of the invention, a stop member 64 is threadably receivable over threaded segment 36c of rod 36. Stop member 64 is, in turn, interconnected with previously identified dose volume control member 34 by means of a pair of oppositely disposed splines 34a which are closely received within a pair of oppositely disposed slots 64a provided in stop member 64

Figure 24A:
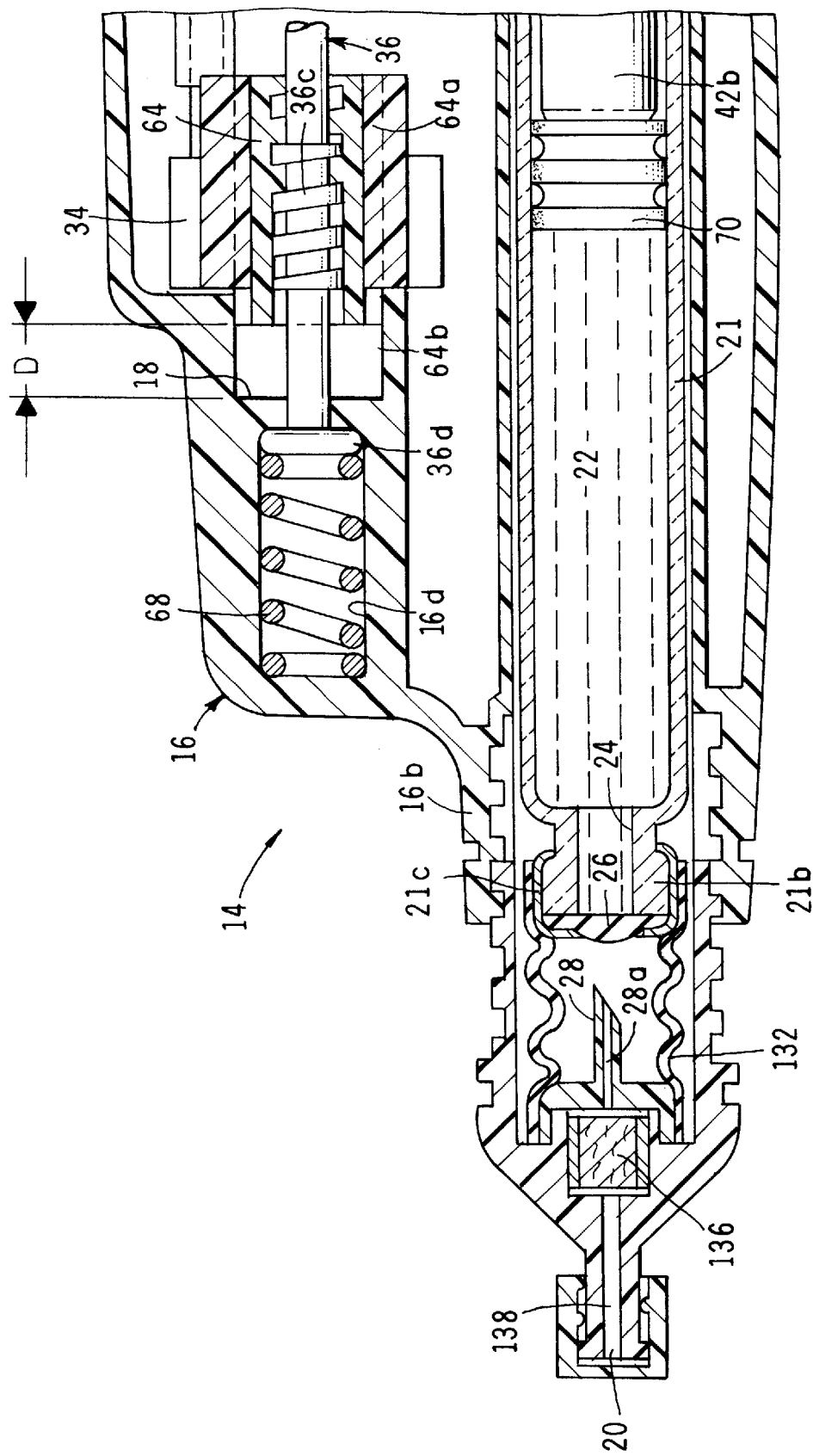
FIGS. 24A and 24B, when considered together, comprise an enlarged cross-sectional view similar to FIGS. 6A and 6B, but showing the position of the various components of the dose interval control means after the dose volume and the delivery intervals have been set by the physician or care giver.

(FIG. 4A). With this construction, rotation of member 34 will cause stop member 64 to move to the right from the first starting position shown in FIG. 6A to the second operating position shown in FIG. 24A wherein the leading edge 64b of the stop member is spaced from stop shoulder 18 of device housing 16 by a distance identified in FIG. 24A by the letter D.

With the novel arrangement described in the preceding paragraphs, after the device is placed in the delivery mode in a manner presently to be described, inward movement of the dispensing member 30 will cause the operating rod assembly to move inwardly or forwardly of device housing 16. This forward travel of the operating rod assembly will be stopped when the leading edge 64b of stop member 64 engages stop shoulder 18 provided on device housing 16 (see FIG. 25A). It is also to be observed that, as the operating rod assembly moves forwardly within housing 16, a forward, spring-engaging head portion 36d provided on operating rod 36 will engage a coil spring 68 which is housed within a counterbore 16d provided in the forward portion of housing 16. Spring 68 forms a part of the second biasing means of the invention and functions to urge rearward movement of the operating means, or operating rod assembly 39, toward its starting position 16.

Considering once again the novel dispensing means of the apparatus of the present form of the invention, this dispensing means, in addition to the previously identified patient operated dispensing member 30 and the dosing rod assembly 42, further includes an elastomeric plunger 70 which is sealably received within reservoir 22 for longitudinal movement therewithin. As earlier discussed, reservoir 22 is formed within a vial-like container assembly 21, having an open end 21a which receives plunger 70 and a forward end 21b which is closed by the earlier-identified septum assembly 26. With this construction, it is apparent that when dispensing member 30 is pushed inwardly of the housing causing the operating rod assembly to also move inwardly, dosing rod assembly 42, which is interconnected therewith, will engage plunger 70 and move the plunger telescopically inwardly of reservoir 22 from the initial starting position shown in FIG. 6A to a second position shown in FIG. 25A. It is apparent that the distance that the plunger 70 can move within reservoir 22 of container 21 depends upon the preset distance "D" between the stop shoulder 18 of device housing 16 and the leading edge 64b of stop member 64 (See FIG. 24A). Clearly, the greater the distance "D" the greater will be the distance plunger 70 will be permitted to move into reservoir 22. Conversely, the smaller the distance "D" the shorter will be the distance the plunger 70 will be permitted to move within reservoir 22. Therefore, by adjusting the distance "D" using the physician-controlled volume setting member, the volume of fluid which will be dispensed from reservoir 22 as a result of the inward travel of plunger 70 within reservoir 22 can be precisely controlled.

Considering once again the dose interval control means of the invention, this means includes, in addition to the previously identified hollow housings 54 and 56, which define first and second chambers 54a and 56a respectively, a pair of sponge-like cellular masses 77 and 79 (FIGS. 6B and 11). Sponge-like mass 77 which is disposed within chamber 56a of member 56 comprises a yieldably deformable member which functions as an energy source when compressed. Sponge-like mass 79, on the other hand, is contained within a collapsible bellows 82, the outboard closed end 82a of which is closely received within chamber 54a of member 54. Mass 79 comprises a fluid containing sponge-like structure which can be saturated with any suitable operating fluid such as glycerin. Other acceptable fluids include flourinated oil such as that available from duPont and sold under the name and style KRYTOX. Flourinated oils are also available in a range of viscosities. Therefore, use of such oils enables extrapolated periods of time delays. More particularly, the greater the viscosity, the greater will be the time required for the oil to flow from the first chamber toward the second chamber via the second rate control means. Disposed intermediate masses 77 and 79 are first and second flow control means. In the present form of the invention, the first flow control means comprises a check valve which functions to permit fluid flow only in a direction toward yieldably deformable mass 77 and functions to block fluid flow in an opposite direction. The second flow control means here functions to precisely control the rate of fluid flow in an opposite direction toward the fluid containing sponge-like mass 79.

In operation of the apparatus of the invention, an inward movement by the patient of dispensing member 30 relative to housing 16 will result in the concomitant inward movement of finger 46c of connector assembly 46. As finger 46c moves inwardly, it will act on member 54 causing bellows 82 to collapse and, at the same time, causing controlled compression of liquid containing, sponge-like mass 79. As mass 79 is compressed, the liquid contained therewithin will be forced therefrom through the first flow control means and thence into chamber 56a of member 56. As the fluid flows under pressure into chamber 56a via the first flow control means, it will compressively deform yieldably deformable mass 77 in the manner shown in FIG. 25B.

As previously mentioned, the first flow control means of the invention comprises a check valve which is here provided in the form of a conventional umbrella type check valve 84 which is captured between first and second flow control members 86 and 88 which are disposed within hollow member 56 in the manner best seen in FIG. 6B. Turning also to FIGS. 9 and 11, it can be seen that flow control member 88 is provided with a plurality of circumferentially spaced-apart fluid flow passageways 88a while member 86 is provided with a plurality of circumferentially spaced fluid flow passageways 86a. As illustrated in the drawings, umbrella check valve 84 is strategically positioned between members 86 and 88 so that the flexible, skirt-like portion 84a of the valve will deflect outwardly in response to fluid flowing through passageways 86a thereby permitting the fluid to flow into fluid passageways 88a and thence into chamber 56a. However, the construction of the umbrella-type check valve is such that the resilient skirt-like portions 84a of the valve will effectively function to prevent fluid flow in the opposite direction, that is, from passageways 88a toward passageways 86a.

To permit fluid flow in a direction from chamber 56a toward chamber 54a and toward cellular mass 79, each of the members 86 and 88 is provided with a central fluid passageway 88b and 86b respectively (see also FIG. 11). Passageway 86b and 88b communicate with each other via a central passageway 84b formed in umbrella check valve 84 so that fluid can flow from chamber 56a toward bellows 82 and chamber 54a via the second flow control means. In the present form of the invention this second flow control means, which functions to control fluid flow in a direction from chamber 56a toward sponge-like member 79, comprises a porous rate control frit 93 that is disposed within central passageway 84b of umbrella check valve 84. Frit 93 can be constricted from a variety of porous materials such as sintered metal or porous ceramic.

Figure 24C:
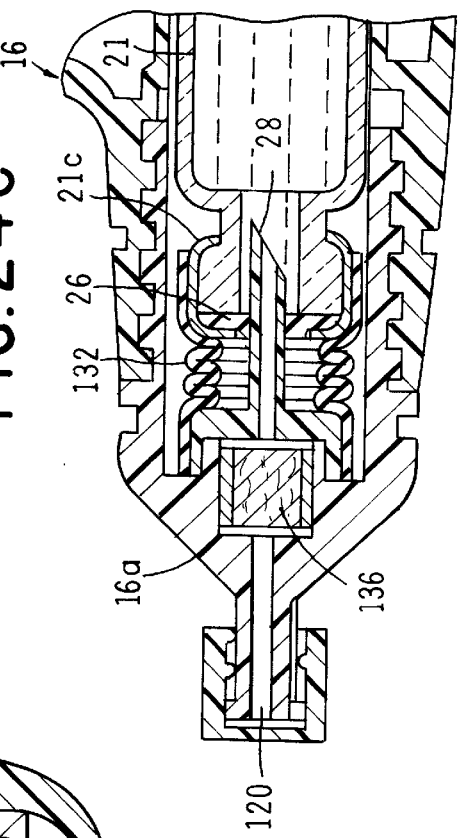
FIG. 24C is a fragmentary, cross-sectional view of the forward portion of the device showing the cannula carrying forward extremity thereof having been rotated in a manner to cause the cannula to penetrate the septum and ready the device for fluid delivery.
Figure 24B:
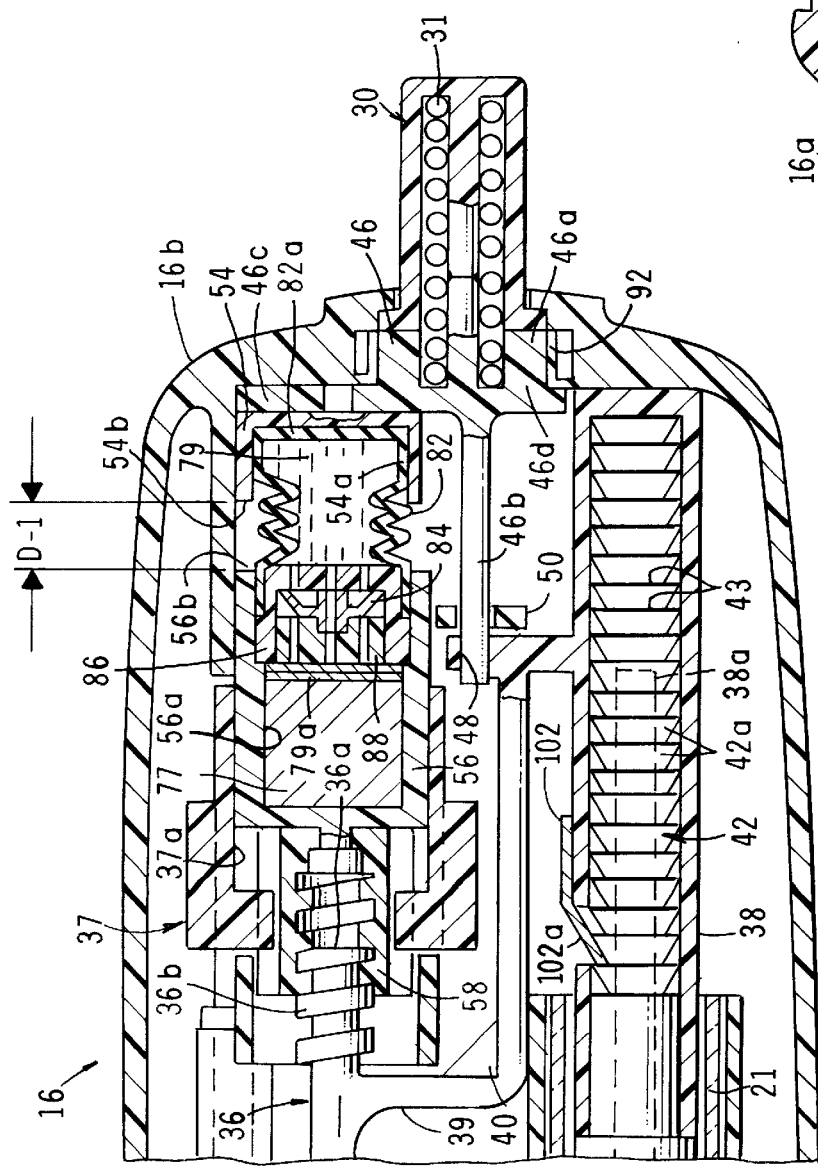

By comparing FIGS. 24B and 25B, it can be seen that the extent of forward travel of finger 46c of connector 46 and the concomitant extent of forward travel of member 54 is governed by the spacing D-1 between the leading edges 54*b* and 56*b* of members 54 and 56 respectively (see also FIG. 26B). This spacing is, in turn, controlled by the position of dose interval control swivel 58. More particularly, as control member 37 is rotated relative to operating rod 36, swivel 58 will move forwardly or rearwardly along operating rod 36 thereby increasing or decreasing the distance D-1, which is the distance of travel permitted by member 54 until it abuts against members 56. It is apparent that, the greater the distance D-1, the greater will be the longitudinal travel permitted by hollow housing 54. Conversely, the smaller the distance D-1, the shorter will be the distance of longitudinal travel permitted by member 54. With this construction, the greater the longitudinal travel permitted by member 54, the greater will be the compression of liquid containing mass 79 and the greater will be the volume of fluid contained therewithin which is transferred to chamber 56*a* via the first flow control means of the invention in the manner shown in FIG. 25*c*. Conversely, the shorter the travel permitted by member 54, the less will be the compression of liquid containing member 79 and the less will be the volume of fluid transferred to chamber 56*a*. Obviously, the greater the volume of fluid that is forced under pressure into chamber 56*a*, the greater will be the degree of compression of yieldably deformable cellular mass 77 due to forces exerted thereon by buffer discs 77*a* affixed to its inboard surface. In a manner presently to be described, the amount of transfer of fluid from fluid containing member 79 toward chamber 56*a* and the concomitant extent of the compression of yieldably compressible cellular mass 77, will control the time interval at which subsequent doses of liquid medicament can be dispensed from reservoir 22.

Figure 25A:
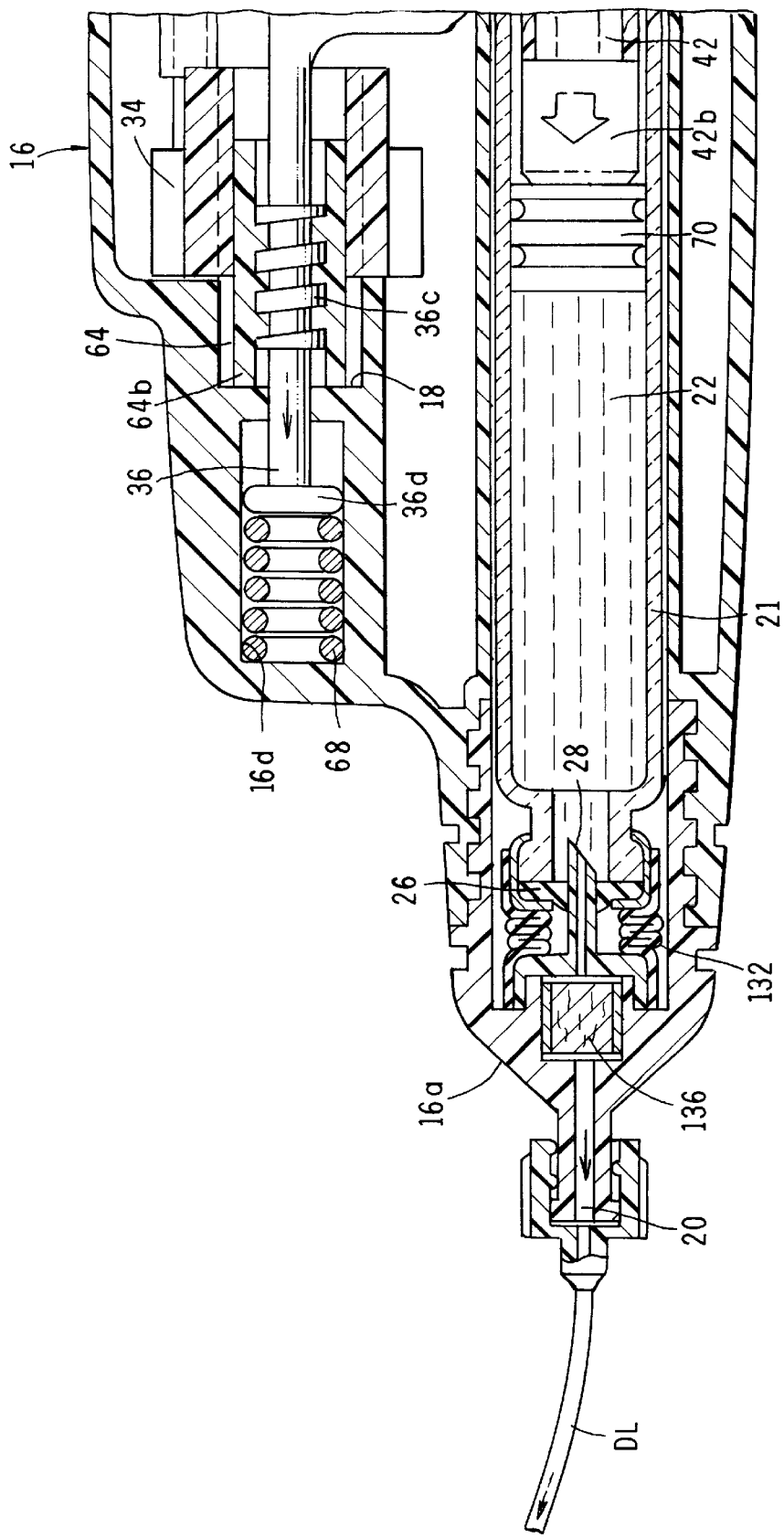
Figure 26A:
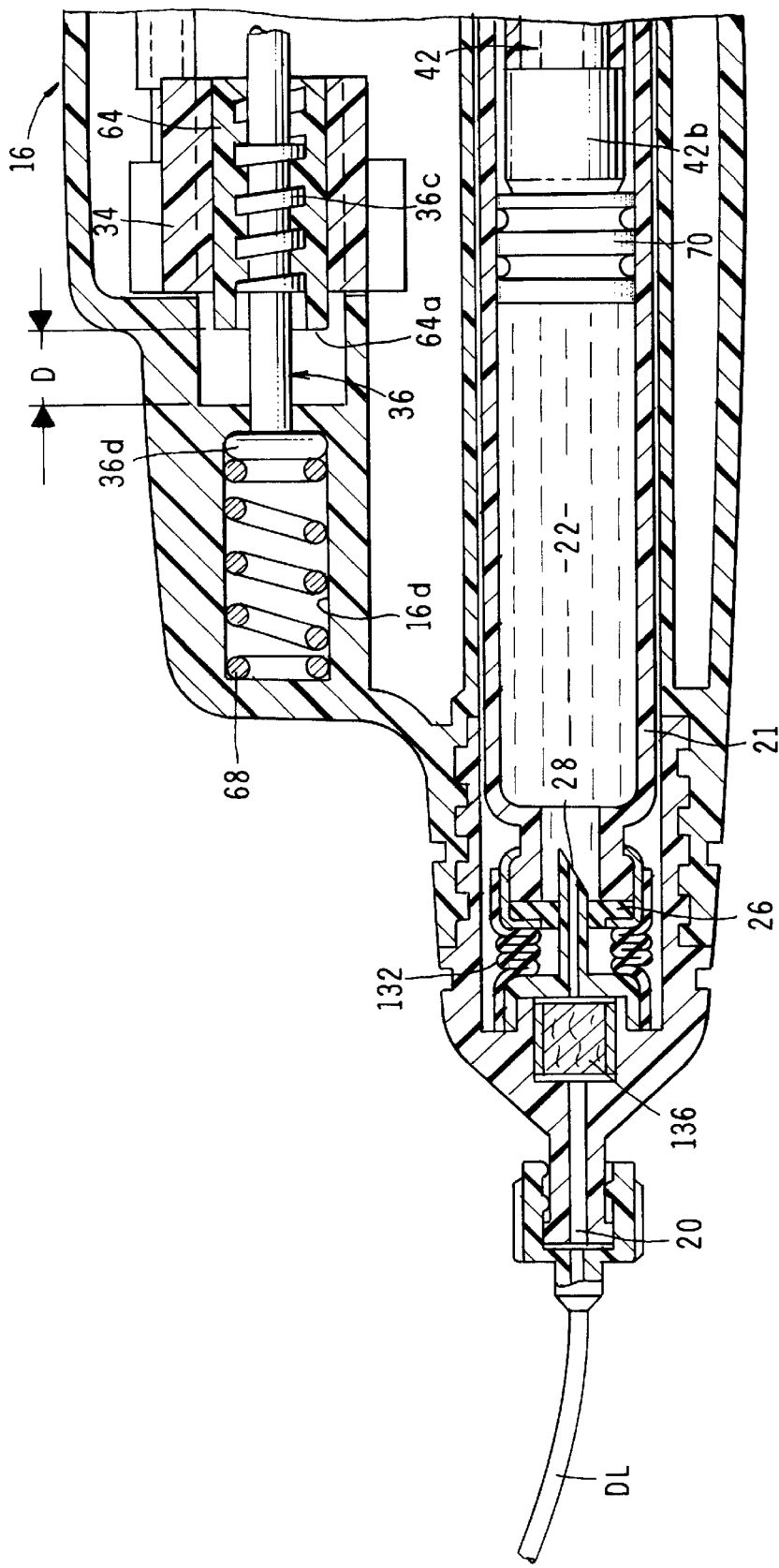
Figure 27:
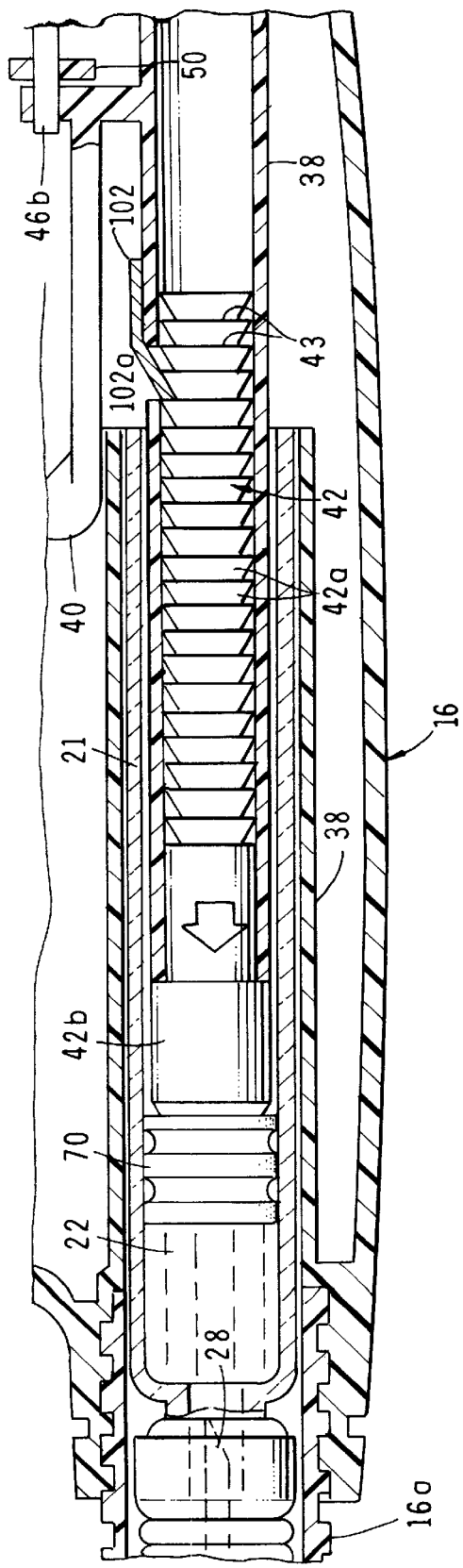
FIG. 27 is a fragmentary, cross-sectional view of a portion of the dispensing means of the invention, showing the position of the component parts of the device following the next advancement of the dispensing member relative to the device housing.
Figure 28:
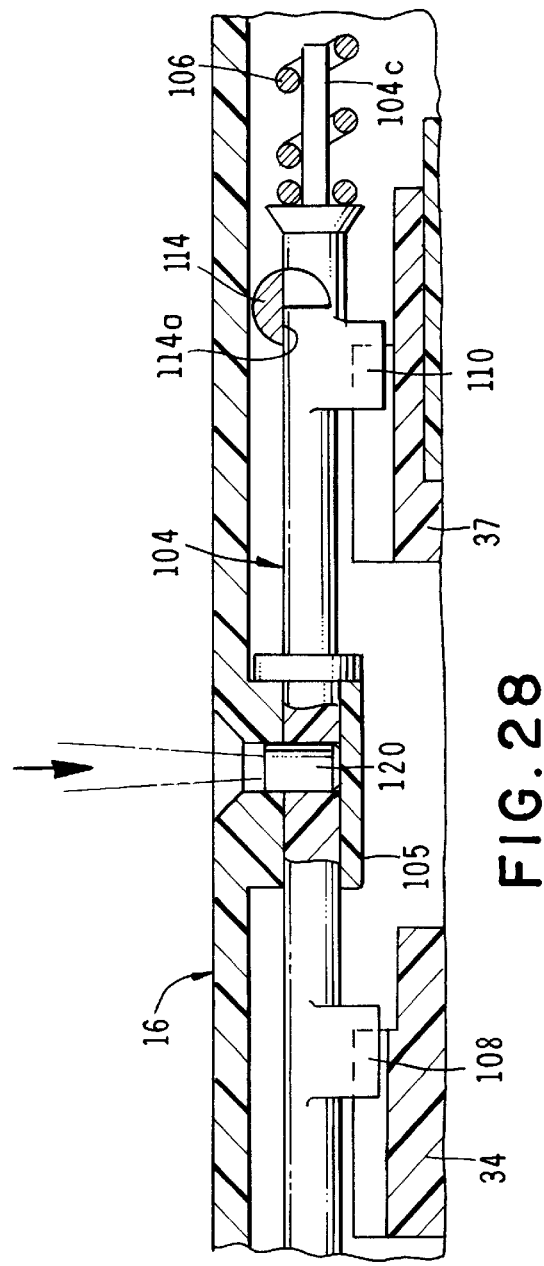
FIG. 28 is a fragmentary, cross-sectional view illustrating the disabling means of the invention in a device disabling configuration.

In order to dispense medication from the apparatus of the invention, the delivery member 30 must be pushed inwardly of housing 16 in the manner shown in FIG. 25*b*. As member 30 is pushed inwardly by the patient, the operating rod assembly 39 will also move forwardly of the housing, and spring 68 will be compressed in the manner shown in FIG. 25A. With this arrangement, when the delivery member is released, spring 68 will function to urge the operating rod assembly to return to its starting position (see FIGS. 26A and 26B). Similarly, as dispensing member 30 is depressed, spring 31 which is housed therein will be compressed so that, upon release of member 30, spring 31 will tend to return it to its starting position. However, as can be seen by referring to FIGS. 26A and 26B, while the operating rod will immediately return to its starting position upon release of member 30, the dose interval control means does not do so. Rather, the return of the interval control means, including housing 54 thereof is uniquely a function of the rate of flow of the fluid from chamber 56*a* of housing 56 toward bellows 82 and toward liquid containing mass 79 via rate control frit 93 (see FIG. 26C). As yieldably compressible member 77 tends to return to its initial starting position in the manner shown in FIG. 26C, buffer members 77*a* will force the fluid contained within chamber 56*a* of member 56 through rate control frit 93 and toward sponge-like member 79. As the fluid impinges upon member 79, it will be absorbed thereby causing the member to gradually expand into its starting configuration. As member 79 expands, it will, in turn, expand bellows 82 and finally both member 54 and finger 46*c* will return to their starting positions as shown in FIG. 6B. As will become apparent from the discussion that follows, the time required for member 54 to return to its starting position equates to the delay time between the delivery of doses of medicament.

The important feature of the apparatus of the invention which positively prevents a second dose to be self-administered by the patient, comprises the delay means of the invention. The novel delay means cooperates with the dose interval control means to prevent a second inward telescopic movement of delivery member 30 until the dose interval control means, including member 54 has returned to its original starting position. This unique delay means feature of the invention is here provided in the form of a plurality of spring tabs 92 which are formed proximate the rear portion 16*c* of housing 16. As shown in FIG. 26B, upon the delivery member 30 being returned to its starting position due to the urging of spring 31, spring tabs 92 will snap outwardly from the position shown in FIG. 25B into the position shown in FIG. 26B where they abut the inboard edge 30*a* of delivery member 30. In this position, tabs 92 positively block further telescopic advancement of the delivery member into housing 16. The locking tabs 92 will remain in the blocking position until member 54 of the dose interval control means of the invention returns to its initial starting configuration as shown in FIG. 6B. More particularly, as indicated in FIG. 26B, as member 54 moves rearwardly it engages finger portion 46C of assemblage 46 causing a collar 46*d* formed on the rearward portion thereof (figure 4A), to move toward the locking tabs 92 and, upon seating, will cam them into their retracted starting position as shown in FIG. 6B. With the spring tabs in this retracted position, delivery member 30 can once again be pushed inwardly of the housing to move the operating rod assembly inwardly and commence the delivery of the next dose of medicament. This unique arrangement positively regulates the intervals at which doses of medicament can be delivered to the patient. More specifically, unless and until the dose interval control means returns to its starting configuration, delivery member 30 cannot be operated and, therefore, the apparatus of the invention remains in a disabled configuration. As previously discussed, the time required for dose interval control means to return to its starting configuration is precisely controlled by the dose interval control means and is a function of the positioning of swivel member 58 along threaded portion 36*b* of operating rod 36 as a result of rotation by the treating physician of control member 37.

Another important feature of the apparatus of the present invention is the dosing rod restraining means which functions to position the dosing rod 42 of the dispensing means at a desired location within tubular member 38. As best seen by referring to FIGS. 4A, 15, and 15A, this novel restraining means comprises a spring tab 100 which is connected to device housing 16 and extends inwardly of tube-like member 38 through an elongated, longitudinally extending slot 38*a*. As dosing rod assembly 42 moves forwardly, spring tab 100 will ratchet over tooth-like members 42*a* provided on rod assembly 42, but as shown in FIG. 15, will engage the shoulders 43 of tooth-like member 42*a* in a manner to restrain rearward movement of dosing rod assembly 42 within member 38. With this arrangement, after rod assembly 42 has been advanced by the operating rod assembly, it will be locked in this advanced position even when tube-like member 38 returns to its starting position upon release of dispensing member 30.

Still another important feature of the invention is the rod assembly advancing means which functions to further advance rod assembly 42 upon dispensing member 30 being once again pushed inwardly of device housing 16. This novel rod assembly advancing means here comprises a first locking tab assembly 102, which is connected to tubular member 38. Locking tab assembly 102 includes an angularly, downwardly depending pushing tab or finger 102a which extends through a slot 103 formed in the upper wall portion of tubular member 38. With this construction, as the operating rod assembly 39, including tube-like member 38, returns to its starting position, upon release of dispensing member 30, finger 102a will slide over the rearward tapered surfaces of the plurality of tooth-like members 42a formed on dosing rod assembly 42 until member 38 returns to its stating position. However, since finger 102a is continuously biased inwardly of tubular member 38, upon the second depression of dispensing member 30, finger 102a will engage an adjacent shoulder 43 of member 42a and in so doing will function to urge forward travel of the dosing rod inwardly of container 21. It is apparent that, each time the operating assembly 39 is urged to return to its starting position by spring 68, dosing rod assembly 42 will be restrained in its advanced position by finger 100 of the restraining means. Then, when dispensing member 30 is once again depressed, pushing finger 102a will engage a shoulder 43 of member 42 causing the member to move further into container 21 thus enabling the delivery of a further dose of medicament.

Figure 20:
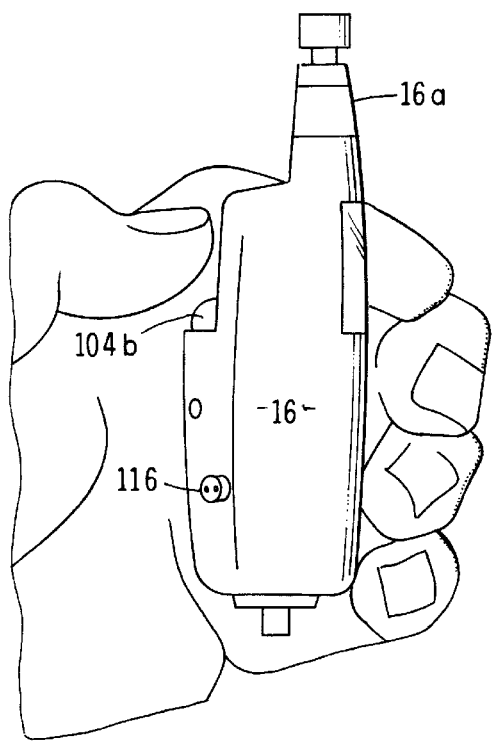
FIG. 20 is a generally diagrammatic view of one side of the device illustrating the commencement of the first step in the operation of the device by the physician or care giver to set the dose volume and dose intervals.
Figure 21:
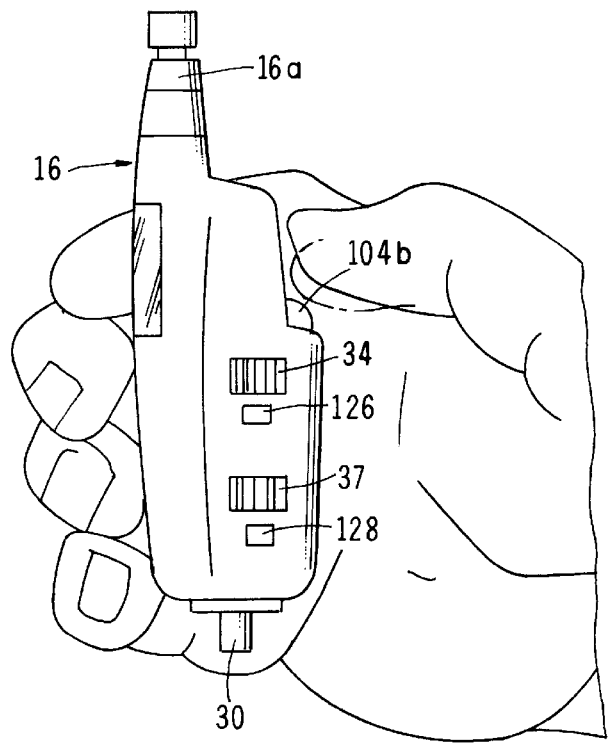
FIG. 21 is a generally diagrammatic view of the other side of the device preparatory to setting the dose volume and dose intervals.
Figure 22:
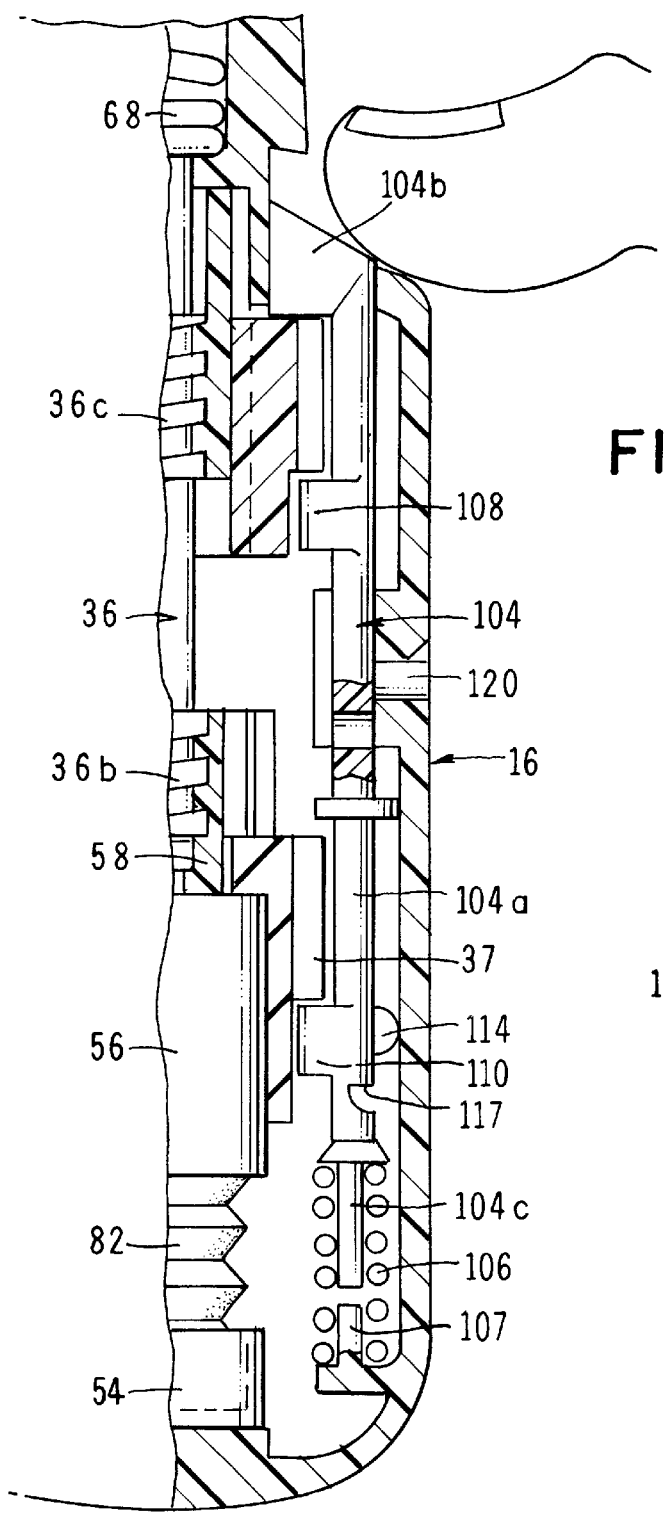
FIG. 22 is a fragmentary, cross-sectional view of the device illustrating movement of the locking rod inwardly of the housing to permit rotation of the control members to accomplish the actual setting of the dose volume and dose delivery intervals.

As previously mentioned the apparatus of the present invention is specially designed so that the dose interval control means and the dose volume control means can be preset only by an authorized person such as the treating physician. For this purpose, locking means are provided for preventing rotation of control knobs 34 and 37 unless and until a locking rod, which comprises a part of the locking means, is moved from the first starting position shown in FIG. 9 to a second operating position shown in FIG. 22. As best seen in FIG. 4B, the locking rod 104 here comprises an elongated member that is mounted within housing 16 for sliding movement within a sleeve-like support 105 formed in device housing 16 (FIG. 9) against the urging of a biasing means which is here provided in the form of a coil spring 106. As indicated in FIGS. 4B and 9, locking rod 104 includes an elongated shank portion 104a, a forward finger-engaging portion 104b, and an end portion 104c which includes a reduced diameter shaft-like portion about which spring 106 is coiled in the manner best seen in FIG. 9. Spring 106 is retained in position by a stub shaft 107 formed on device housing 16. First and second space-apart protuberances 108 and 110 are formed on the central portion of rod 104 and are adapted to engage rotatable control members 34 and 37 in the manner to prevent their rotation when the locking rod is in the starting position shown in FIG. 9 (see also FIG. 13). However, when a pushing force is exerted in a rearwardly direction on portion 104b of the locking rod in the manner shown in FIG. 22, the locking rod will slide within supporting sleeve 105 from its first locking position into the second unlocked position shown in FIG. 22 wherein control knobs 34 and 37 can be rotated by the treating physician to precisely preset the volume of each dose of medicament to be delivered also to preset the permitted interval between doses (see also FIGS. 20 and 21). Upon a release of finger pressure of end portion 104b, spring 106 will automatically urge member 104 to return to the locking position.

Figure 8:
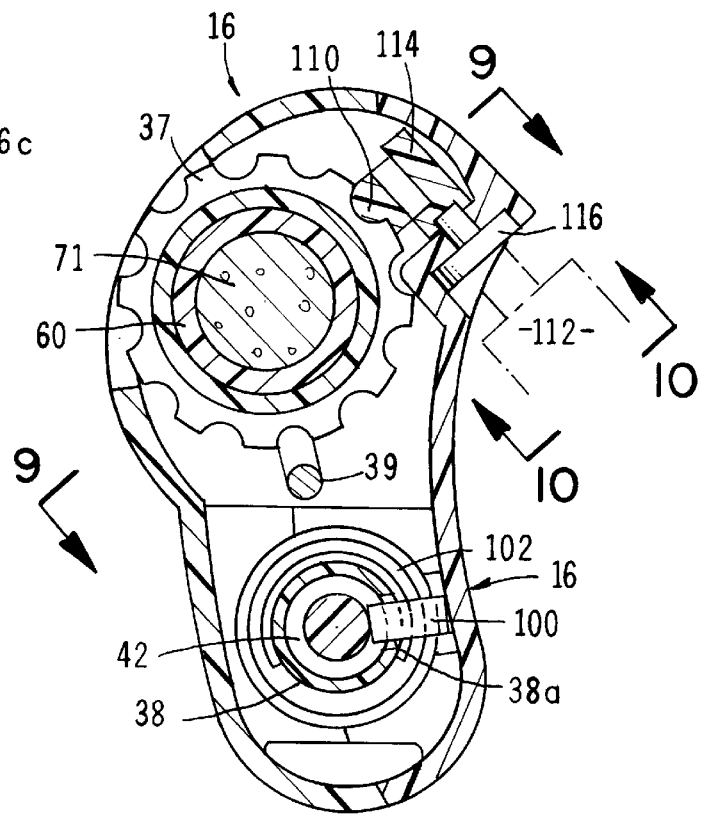
FIG. 8 is a cross-sectional view taken along lines 8—8 of FIG. 6B.
Figure 10:
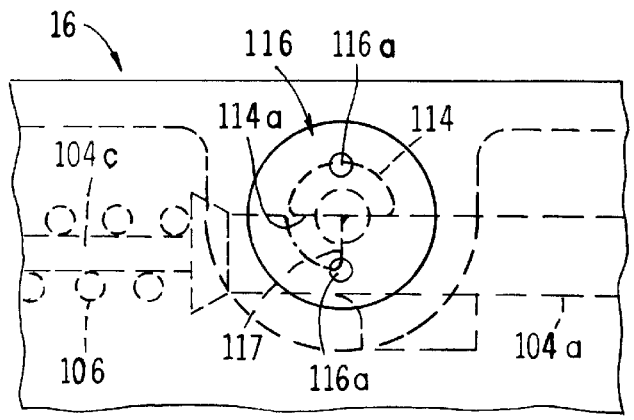
FIG. 10 is an enlarged cross-sectional view taken along lines 10—10 of FIG. 8.
Figure 10A:
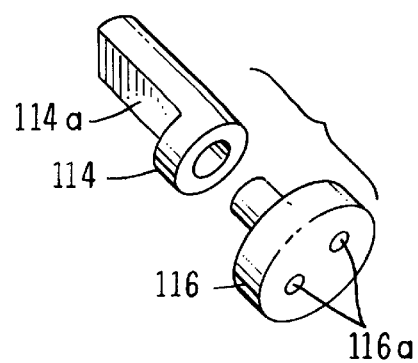
FIG. 10A is an enlarged, generally perspective, exploded view of one of the -lock-out mechanisms of the device.
Figure 23:
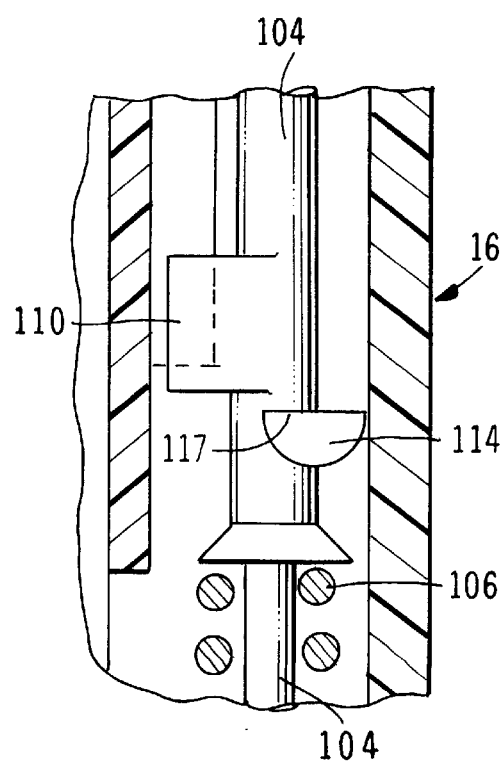
FIG. 23 is an enlarged, fragmentary cross-sectional view showing the physician's key locking mechanism moved into a locked position following setting of the dose volume and dose intervals and predetermining further inward movement of the locking rod.

Another very important feature of the present invention is the provision of key control means which function to control movement of the locking rod in a manner to enable the setting of the dose volumes and time intervals between doses. Referring particularly to FIGS. 8 and 10A, this important key control means comprises a locking mechanism which can be operated only by a physician key 112 (FIGS. 1, 18 and 19). The locking mechanism, which is mounted in the device housing 16, comprises an elongated body portion 114 and a head portion 116 which is connected thereto. Body portion 114 includes a flat 114a which is adapted to engage a shoulder 117 formed on locking rod 104 (FIGS. 4B and 10). When flat 114a is in engagement with locking shoulder 117 in the manner shown in FIG. 23, rearward movement of the locking rod 104 is positively prevented. However when member 114 is rotated by the physician's key 112 to a position shown in FIG. 22 where flat 114a will clear shoulder 117, the locking rod 104 can be moved rearwardly of the housing against the urging of spring 106 by pushing on the forward finger engaging portion 104b. In order to rotate member 114 within housing 16, it is necessary to insert the two spanner elements 112a formed on the physician's key (FIGS. 1, 18, and 19) into spaced-apart spanner element receiving openings 116a provided in portion 116 of the locking assembly. When pins 112a are inserted into openings 116a and the assembly rotated, flat 114a can be moved into and out of engagement with shoulder 117 thereby either blocking or permitting inward movement of the locking assembly 104 relative to housing 16. After control member 34 and 37 have been set and the locking rod released, spring 106 will return the locking rod to its initial position and the physician or other care giver can lock the locking rod in this locked position by rotating physician's key 112 into the locked position shown in FIG. 23 and then removing the key from the locking assembly. The setting made by the treating physician will then remain unchanged unless and until the physician unlocks the locking mechanism using the locking key 112.

In addition to the physician key locking means, the apparatus of the present invention includes novel disabling means for completely disabling the apparatus of the invention and preventing further use thereof Referring to FIG. 9, this disabling means here comprises a generally cylindrically shaped locking pin 120 which is carried by device housing 16 and is irremovably received within a bore 122 formed centrally of locking rod 104. When pin 120 is inserted into bore 122, all further longitudinal sliding movement of the locking shaft 104 is positively prevented and neither the dose volume control means of the invention, nor the dose interval control means can be reset.

In using the apparatus of the invention, the treating physician, or other appropriate health care worker, first adjust control members 34 and 37 to preset the dose interval control means and the dose volume control means of the invention. After the setting have been made, the patient is free to self-administer doses of a predetermined volume of a prescribed medicament at predetermined intervals of time. Adjustment of the control members 34 and 37 is accomplished by first inserting the physician's key 112 into the physician key locking mechanism portion 116. By then, turning the key to the unlocked position locking rod 104 can be moved longitudinally of housing 16 in the manner shown in FIGS. 20, 21 and 22 against the urging of spring 106 to a position wherein the dose interval control member 34 and the dose volume control member 37 can be freely rotated. While holding the locking rod inwardly, the treating physician can first rotate to dosing volume control member 34 in a manner to set the volume of the dose to be delivered and then rotate the dose interval control member 37 to set the interval of time at which the doses can be self-administered by the patient. In this regard, it is to be noted that small windows 126 and 128 are provided in housing 16 (FIG. 1) so that the treating physician can view indicia associated with both the dose volume and the dose intervals which correspond to the position of the control members 34 and 37 respectively. Once the settings have appropriately been made, locking rod 104 is released and the physician's key is rotated into the locking position and removed.

Next, closure cap 129 is removed and the delivery line "DL" (FIG. 1) is attached to the forward portion of the housing and a safety ring and tear away safety strip 130 (FIGS. 1, 4A and 6A) is removed. Removal of the safety strip 130 in the manner illustrated in FIGS. 17 and 17a permits the forward end 16a of housing 16 4? to be rotated relative to the housing body in the manner shown in FIG. 24C so as to collapse a bellows 132 which surrounds and encapsulates cannula 28. As the front end 16a is rotated relative to the body of the housing, cannula 28 will engage and pierce septum 26 thereby opening communication between reservoir 22 and outlet 20 of housing 16 (see FIG. 24C). This done, the device is ready for the delivery step of the first dose of medicament.

When the patient desires to self-administer the first dose of medicament, the delivery line is connected to an in-dwelling catheter and dispensing member 30 is pushed inwardly of housing 16 in the manner shown in FIG. 25B. This causes the operating rod assembly, portions of the dose volume means, and the dose interval control means to all move forwardly until stop member 64 of the dose volume control means engages stop 18 provided in housing 16. As the operating assembly moves forwardly, dosing rod 42 will urge plunger 70 forwardly of reservoir 22 causing a portion of the fluid contained within the reservoir to flow into passageway 28a of cannula 28. From passageway 28a the fluid will flow through filter means shown here as a porous filter 136 of conventional construction which is housed in forward portion 16a of the housing and thence into passageway 138 which leads to outlet port 20 of the device and into the delivery line "DL".

When the dispensing member 30 is released, spring 31 will cause member 30 to immediately return to its starting position and locking tabs 92 will move from their starting position shown in FIG. 6B into the locking position shown in FIG. 26B. As earlier discussed, the locking tabs will retain the dispensing member 30 in its starting position until the predetermined lock-out interval has expired and member 54 returns to its starting position due to the urging of cellular mass 79. More particularly, as the bellows 82 of the dose interval control means expands toward its starting position, member 54 will engage finger 46c urging assembly 46 rearwardly. As assembly 46 moves rearwardly, collar portion 46d of assembly 46 will cam the locking tabs back into their starting position thus releasing the dispensing member 30 for the delivery of the next dose.

As earlier discussed, the dose interval control means will expand at a rate proportional to the rate of fluid flow from chamber 56a into bellows 82 via control frit 93. Meanwhile, the operating rod assembly is returned to its starting position due to the urging of biasing spring 68. However, as the operating rod assembly returns to its starting position, the dosing rod 42 will be retained in its forward most position by locking finger 100 of retaining means. As each subsequent dose is delivered by depressing member 30, pusher finger 102a which is connected to tube-like member 38 of the operating rod assembly will push the dosing rod incrementally forwardly thereby advancing plunger 70 further into reservoir 22 of container 21.

Wien the contents of the vial have been exhausted, or when the use of the device is no longer desired, the treating physician, or health care worker can disable the device by depressing the disable means or button 120 thereby positively preventing any further longitudinal movement of locking rod 104 and thereby preventing any further dose and interval settings.

Referring to FIG. 16, an alternate form of the apparatus is there illustrated. This apparatus is identical in all respects to the earlier described embodiments save that cannula 28 has been replaced by a blunt end cannula 131 which is adapted to pierce a slit septum 133 which closed the forward opening of container 21.

Turning next to FIGS. 29 through 33, still another form of the patient control and infusion device of the present invention is there illustrated and generally designated by the numeral 130. This form of the invention is similar in most respects to the embodiment illustrated in FIGS. 1 through 28 and like numerals have been used in FIGS. 29 through 33 to identify like components. The major differences between this latest form of the invention and the earlier-described embodiment resides in certain structural changes made in the housing 132 and a differently constructed disabling means which function to completely disable the apparatus.

Referring particularly to FIG. 29, it is to be noted that the general constriction of the housing of the apparatus there shown is quite similar to that previously described save for the fact that internal support members 136 and 138 have been provided to provide additional structural support to fluid container 21 (FIGS. 29, 32 and 33). These structural support members are preferably molded into the housing during its fabrication and function to more securely maintain the fluid containing vial in position within the housing during the delivery step.

With regard to the disabling mechanism of this latest form of the invention, this important mechanism has been moved from the top of the housing to the side of the housing and as best seen in FIGS. 29 and 31 resides in close proximity with connector assembly of the dispensing means. More particularly, as best seen in figure 31 (see also FIG. 6B), an inwardly telescoping disabling button 134 is disposed proximate portion 46a head portion of the connector assembly so that when depressed inwardly in the direction of the arrow of FIG. 31, it will positively block forward advancement of assemblage 46 as a result of an inward force being exerted on member 30. Obviously, when disabling button 134 is fully inserted, the device will therefore be totally disabled.

Figure 34:
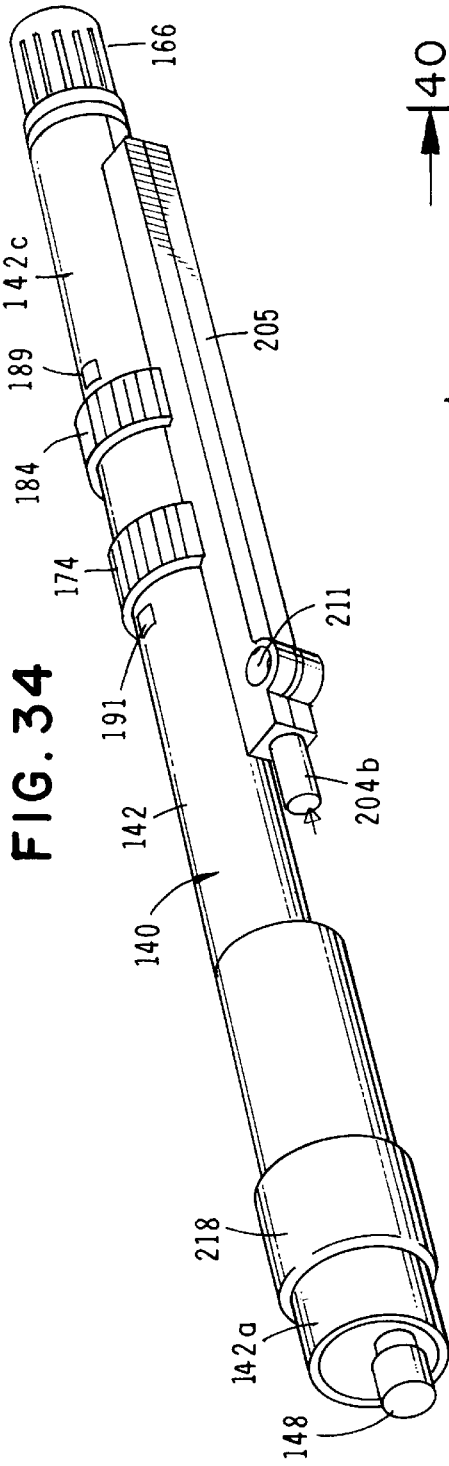
FIG. 34 is a generally perspective view of still another embodiment of the patient control infusion device of the invention.

Referring next to FIGS. 34 through 48, yet another form of the patient control infusion device of the present invention is there illustrated and generally designated by the numeral 140. This form of the invention is also somewhat similar to the earlier described embodiments, but is in a generally in-line configuration (see FIG. 34). In this latest embodiment of the invention, the device comprises an elongated device housing 142 having an internal stop 144 (FIG. 34A) and a fluid outlet 146 which can be coupled with a conventional delivery set upon removal of closure cap 148 (FIG. 34).

Disposed within housing 142 is a fluid container 150 having a fluid reservoir 152 for containing the fluid to be delivered. Fluid reservoir 152 has an outlet 154 which can be placed in fluid communication with the fluid outlet 146 of device housing 142 via a closure means, here comprising a pierceable septum 156. Septum 156 is held in position on container 150 by a crimp ring 150c and is pierceable by a hollow cannula 158 which is mounted within a forward portion 142a of device housing 142. Forward portion 142a of the device housing is connected to a forward, dispensing unit 146b within which an outlet passageway 160 is formed. The assemblage 149 thus formed is threadably connected to the main body portion of housing 142 in the manner shown in FIG. 34A. When cannula 158 has penetrated septum 156 as a result of relative rotation between body portion 142 and assemblage 149 in a manner presently to be described, passageway 160 is placed in fluid communication with vial reservoir 152 via a filter means shown here as porous filter 164.

Figure 47B:
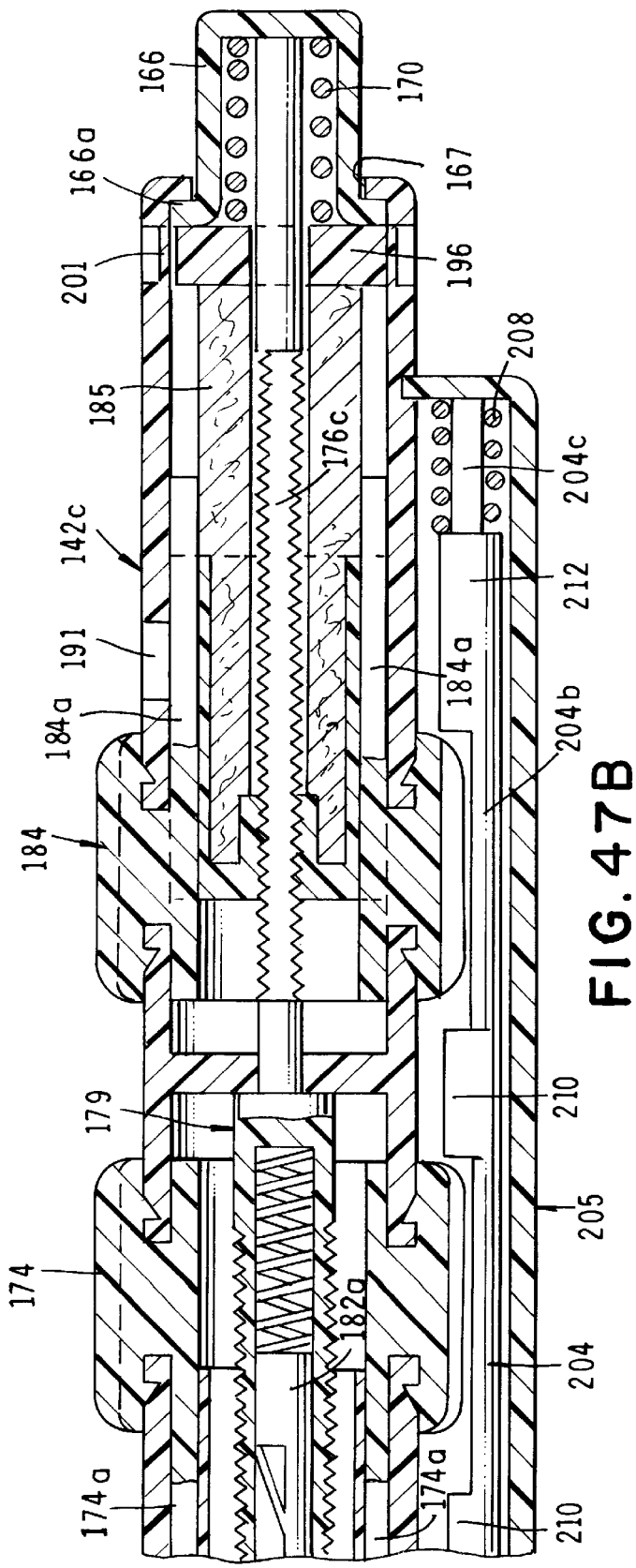

Manually operated dispensing means are connected to device housing 142 proximate the rearward portion 142c thereof. As before, the dispensing means functions to sequentially dispense multiple doses of fluid of a predetermined volume from outlet 146. As best seen in FIGS. 34B, 47B, and 48, the dispensing means here comprises a generally cylindrically, shaped hollow dispensing member 166 which is telescopically receivable within an opening 167 provided in the rearward portion 142c of housing 142. Disposed within member 166 is a first biasing means, shown here as a coil spring 170, which yieldably resists inward movement of member 166.

Connected to the dispensing means is the important operating means of the invention, which functions to control the sequential dispensing of multiple doses of fluid from reservoir 152 of vial 150. This important operating means again comprises two major control means, namely a dose interval control means for controlling the interval of time between the dispensing of each dose of medication and a dose volume control means for controlling the volume of each dose of medication to be delivered.

The dose volume control means of the present form of the invention includes a manually adjustable dose volume control member 174 which is rotatably carried by device housing 142 and is rotatable by the treating physician or health care worker to preset the volume of the doses of medication to be delivered to the patient. Member 174 is operably associated with an operating rod 176 which forms a part of an operating rod assembly generally designated in the drawings by the numeral 179. Operating rod assembly 179 also includes a dosing rod 182 (FIG. 34B), the purpose of which will presently be described.

A dose interval control member 184, which forms a part of the dose interval control means of the invention, is also operably associated with operating rod 176 and, as will presently be described, is rotatable by the treating physician or health care worker to preset the intervals at which doses of medicaments can be delivered by the patient.

Figure 34A:
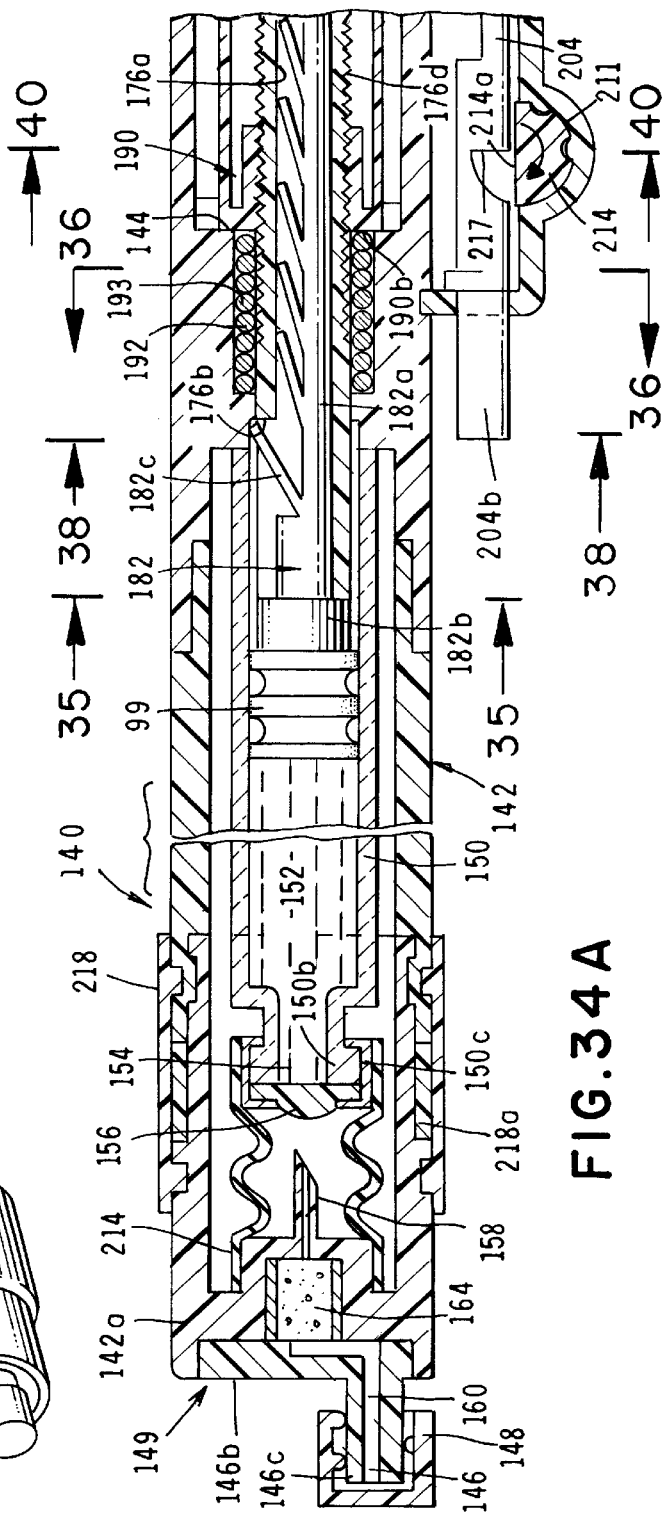
Figure 37:
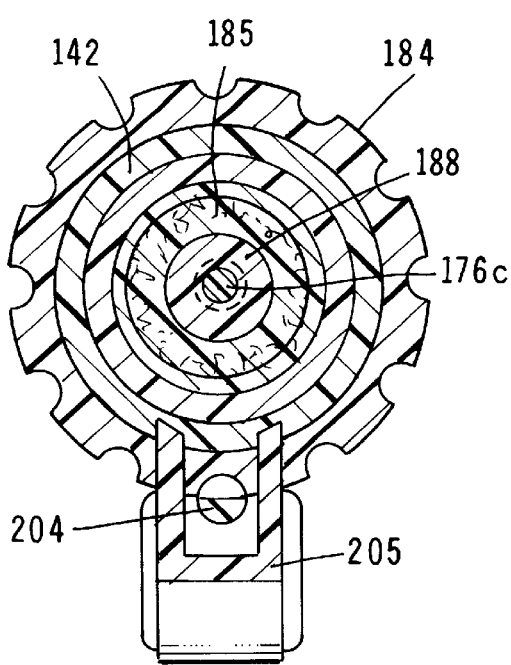
FIG. 37 is a cross-sectional view taken along lines 37—37 of FIG. 34B.
Figure 38:
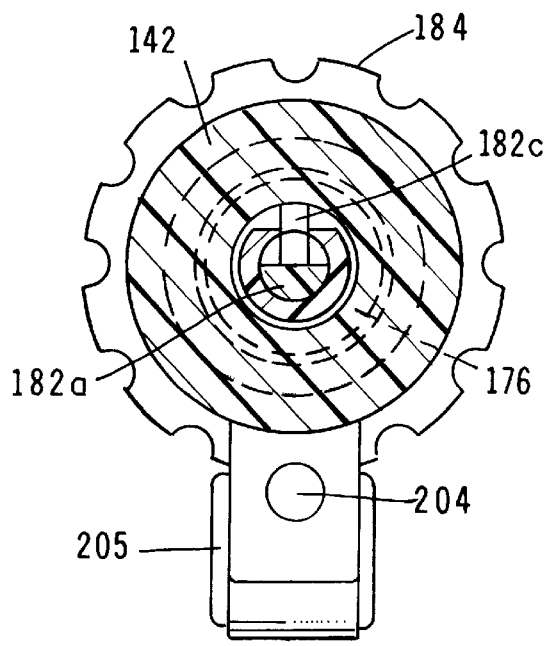
FIG. 38 is a cross-sectional view taken along lines 38—38 of FIG. 34A.
Figure 39:
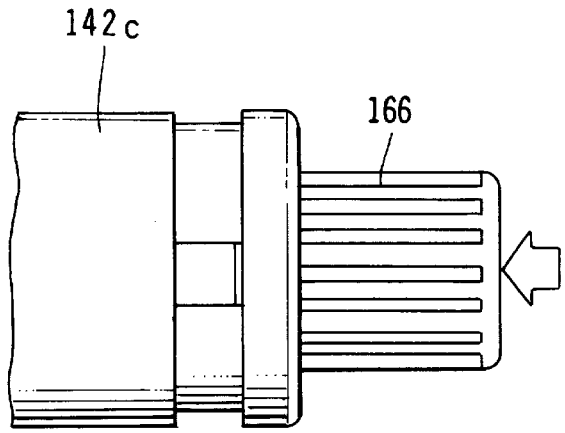
FIG. 39 is an enlarged, side-elevational, fragmentary view of one form of the dispensing mechanisms of the device shown in FIG. 35.
Figure 40:
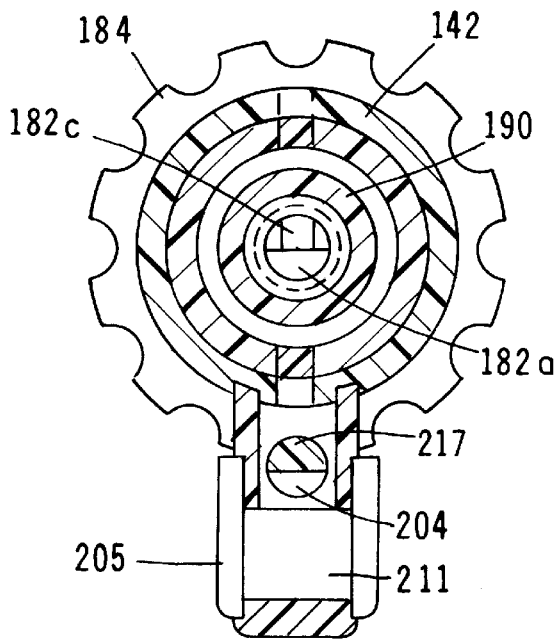
FIG. 40 is a cross-sectional view taken along lines 40—40 of FIG. 34A.
Figure 49A:
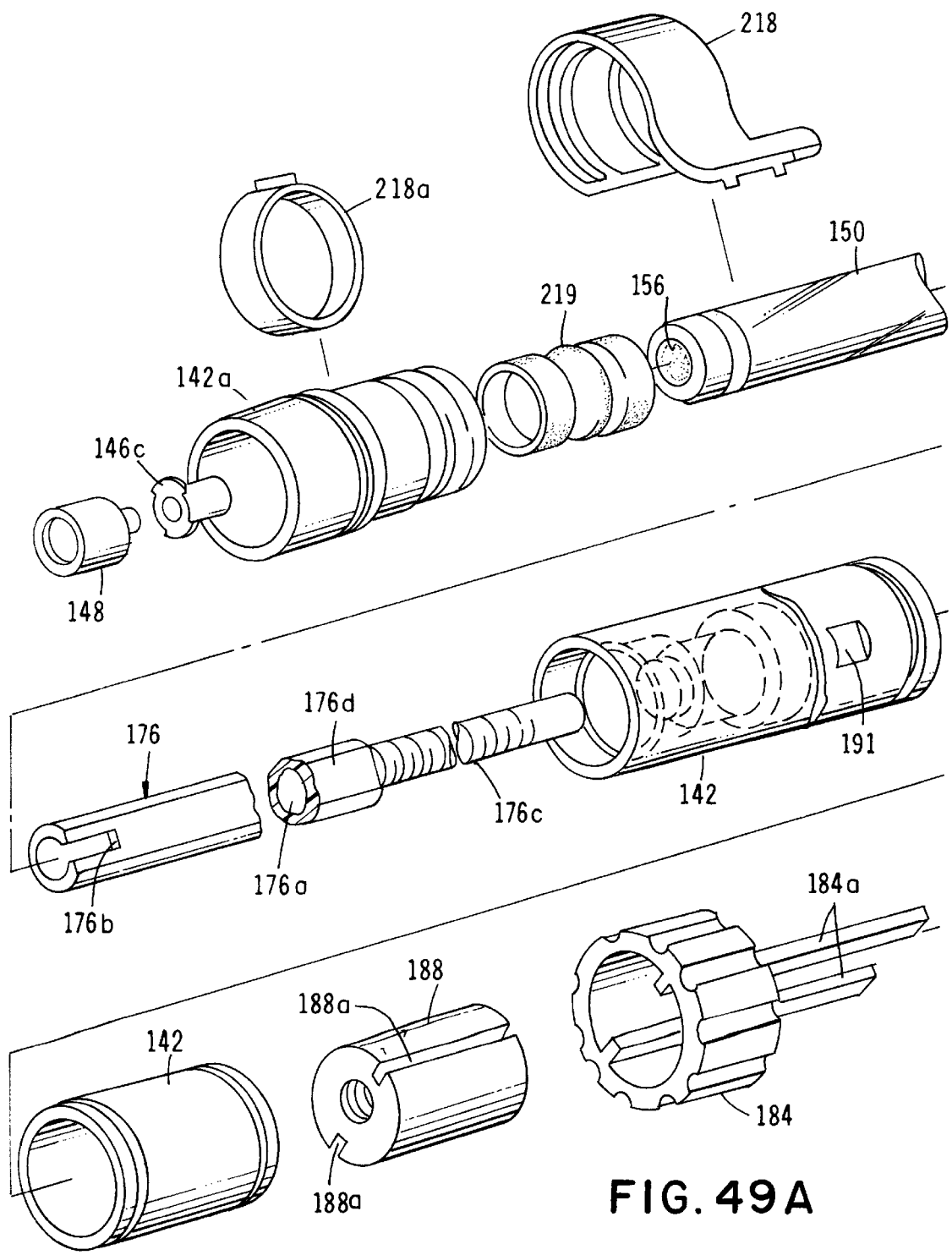
FIGS. 49A and 49B, when considered together, comprise a generally perspective, exploded view of the apparatus shown in FIG. 34.
Figure 49B:
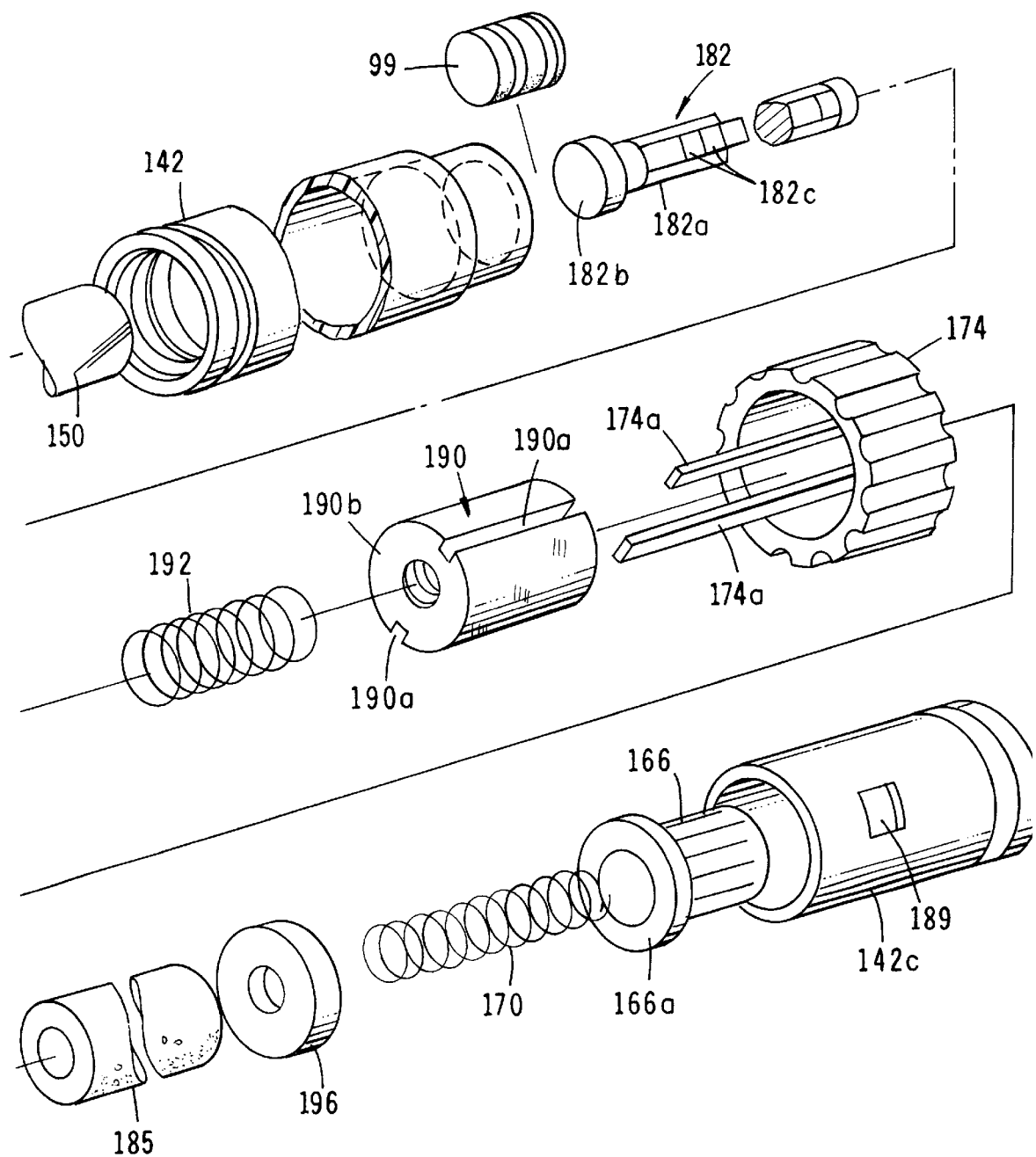

As best seen by referring to FIGS. 34A and 49B, dosing rod 182, which includes shank portion 182a that is telescopically movable within an interior, generally cylindrical chamber 176a of operating rod 176. Dosing rod 182 also has a head portion 182b and, as will presently be described, functions to cause fluid to flow outwardly from reservoir 152 of vial 150 when dispensing member 166 of the dispensing means is pushed inwardly of housing 142 in the manner shown in FIG. 47D.

Considering particularly the important dose interval control means of the invention, it is to be observed that an inward force exerted by the patient on dispensing member 166 will cause a forward, or inward movement of the entire operating rod assembly 179 relative to a novel, readily compressible elastomeric member 185 and relative to housing 142. This inward movement of operating rod assembly will also cause a forward movement of dosing rod 182 as a result of one of a series of resiliently deformable tabs or fins 182c formed on shank portion 182a of the dosing rod being engaged by the forward shoulder 176b formed on operating rod 176 (see FIG. 34A).

Referring particularly to FIGS. 34B and 49A, it can be seen that operating rod 176 includes a threaded shank portion 176c to which a dose interval, drum-like member 188 is connected. Dose interval member 188 is, in turn, interconnected with knob-like control member 184 by means of oppositely disposed splines 184a which extend therefrom and which are slidably receivable within oppositely disposed grooves 188a provided in member 188. Indicia provided on member 188, which is viewable through a window 189 in the housing, indicates to the physician the interval selected.

Considering next the dose volume control means of the invention, a dose volume control, drum-like member 190 is threadably receivable over threaded portion 176d of rod 176. Member 190 is, in turn, interconnected with previously identified dose volume control member 174 by means of a pair of oppositely disposed splines 174a which are closely received within a pair of oppositely disposed slots 190a provided in member 190 (FIG. 49B). With this construction, rotation of member 190 will cause member 174 to move to the right from a first starting position shown in FIG. 34A to a second operating position shown in FIG. 47A wherein the leading edge 190b of the member is spaced from stop shoulder 144 of device housing 142 by a selected distance "D" (FIG. 47A). Indicia provided on member 190 are viewable through a window 191 provided in the housing and serve to indicate to the physician the dose volume selected.

With the novel arrangement described in the preceding paragraphs, and with the apparatus in the position shown in FIGS. 47A and 47B, an inward movement of dispensing member 166 will cause the operating rod assembly 179 to move inwardly or forwardly of device housing 142. This forward travel of the operating rod assembly will continue until the leading edge 190b of member 190 engages internal stop shoulder 144 provided on device housing 142 where the forward movement will be stopped. It is also to be observed that member 190 is in engagement with coil spring 192 which is housed within a counterbore 193 provided in the forward portion of housing 142. Spring 192 forms a part of the second biasing means of the invention and functions to continuously urge rearward movement of the operating means, or operating rod assembly 179, internally of housing 142. It is also to be observed that, when the dispensing member 166 is pushed inwardly of housing 142 a flange 166a formed on member 166 will engage a disk-like member 196 which is disposed within housing 142e in engagement with the previously identified elastomeric yieldably compressible member 185. Inward movement of member 166 and disk 196 in the manner shown in FIG. 47D will compress member 185 in a manner to cause a buildup of internal stresses within the member which stresses tend to cause member 185 to return to its starting position. In addition to the elastomeric member 185 yieldably resisting inward movement of dispensing member 166, coil spring 170 also resists inward movement of member 166.

As earlier discussed, a reservoir 152 is formed within a vial-like container 150 is disposed within the forward portion 142a of housing 142. Container 150 has an open end 150a which receives a plunger 99 and an end 150b which is closed by the earlier-identified septum 156. With this construction, it is apparent that when dispensing member 166 is pushed inwardly of the housing causing the operating rod assembly to also move inwardly, dosing rod assembly 182, which is interconnected therewith by means of fins 182c, will engage plunger 99 and move the plunger telescopically inwardly of reservoir 152. The distance that the plunger 99 can move within reservoir 152 of container 150 depends upon the preset distance "D" between the stop shoulder 144 of device housing 142 and the leading edge 190b. Clearly, the greater the distance "D" the greater will be the distance plunger 99 will be permitted to move into reservoir 152 and the greater will be the volume of fluid disposed. Conversely, the smaller the distance "D", the shorter will be the distance the plunger 99 will be permitted to move within reservoir 152 and the lesser will be the volume of fluid dispensed. Therefore, by adjusting this critical distance "D" using the physician-controlled volume setting member 174, the volume of fluid which will be dispensed from reservoir 152 as a result of the inward travel of plunger 99 within reservoir 152 can be precisely controlled.

In operation of this latest form of the invention, an inward movement by the patient of dispensing member 166 relative to housing 142 will result in the concomitant inward movement of disk 196. As disk 196 moves inwardly, it will act on elastomeric member 185 causing it to compressively deform. It is apparent that the degree of compression of elastomeric member 185 is controlled by the location of member 188 along threaded shank portion 176c of rod 176. This location of member 188 is, in turn, determined by the treating physician controllably rotating control member 184 relative to housing 142 in the manner depicted in FIG. 47B. With this construction, the greater the compression of elastomeric member 185, the greater will be the time required for member 185 to return to its starting position. Conversely, the lessor the degree of compression of member 185, the shorter will be the time required for the member to return to its starting position. In a manner presently to be described, the degree of compression of member 185 can be used to precisely control the time interval between dispensing of doses of liquid medicament from reservoir 152.

In order to dispense medication from the apparatus of the invention, the delivery member 166 must be pushed inwardly of housing 142 in the manner shown in FIG. 47D. As member 166 is pushed inwardly by the patient, the operating rod assembly 179 will also move forwardly of the housing, and spring 170 will be compressed in the manner shown in FIG. 47D. With this arrangement, when the delivery member is released, spring 170 which is housed therein will be compressed so that, upon release of member 166, spring 170 will tend to rapidly return it to the position shown in FIG. 48 wherein it will be locked against further inward movement by resilient locking tabs 201 which are provided proximate the rearward extremity of housing 142, tabs 201 here comprise a part of the delay means of this latest form of the invention. However, it is to be noted that while the dispensing member 166 will immediately return to its starting position upon its release (FIG. 48), the dose interval control means will not do so. Rather, the return of the interval control means, including disk 196, is uniquely a function of the rate of expansion of elastomeric member 185 from its compressed configuration to its starting position, which, in turn, is a function of the degree of compression of member 185.

As elastomeric member 185 expands toward its starting position in the manner indicated by the arrow 187 of FIG. 48, it will urge disk 196 rearwardly into camming engagement with locking tabs 201 and then into its starting system operating position shown in FIG. 34B. The time required for elastomeric member 185 and disk 196 to return to their starting positions equates to the delay time between the sequential dispensing of doses of medication.

An important feature of the apparatus of this latest form of the invention is the previously mentioned dosing rod restraining and advancing means which function to position and advance the dosing rod 182 of the dispensing means relative to housing 142. These novel means include the previously identified resiliently deformable fins 182c which extend outwardly from the shank portion 182a of dosing rod 182. As the operating rod assembly 179 moves forwardly as a result of depressing member 166, its leading edge 176b will engage a fin 182c urging rod 182 forwardly. However, fins 182c are uniquely constructed and arranged to permit the operating rod assembly 179 to return toward its starting position due to the urging of a spring 192 without interference from the resilient fins. On the other hand, once the dosing rod is advanced by the operating rod, it will be restrained in its advance position as a result of one of the fins, such as fin "F" (FIG. 47E), engaging a locking shoulder 203 provided interiorly of housing 142. With this arrangement, after dosing rod 182 has been advanced by the operating rod assembly, it will be locked in this advanced position even when the operating rod assembly returns to its starting position due to the urging of spring 192 upon release of dispensing member 166.

As previously mentioned, upon release of dispensing member 166 and, as operating rod 176 is urged rearwardly by spring 192, it will freely slide over fins 182c provided on the dosing rod 182. However, since fins 182c are continuously biased outwardly as the operating rod moves rearwardly, one of the fins, such as fin "F", will engage shoulder 203 so that upon the second depression of dispensing member 166, the leading edge of operating rod 176 will engage the outwardly extending fin and in so doing will urge further forward travel of the dosing rod and plunger 99 inwardly of the container 150 to dispense the next dose of medicament.

As in the earlier described embodiment of the invention, this second embodiment is specially designed so that the dose interval control means and the dose volume control means can be preset only by an authorized person such as the treating physician. For this purpose, locking means are provided for preventing rotation of control knobs 174 and 184 unless and until a locking rod 204, which comprises a part of the locking means, is moved from its first starting position to a second operating position. As best seen in FIGS. 34A and 34B, the locking rod 204 here comprises an elongated member that is mounted within housing 142 for sliding movement within a sleeve-like support 205 formed on housing 142 against the urging of a biasing means which is here provided in the form of a coil spring 208. Locking rod 204 includes an elongated shank portion 204a, a forward finger-engaging portion 204b, and an end portion 204c which includes a reduced diameter shaft-like portion about which spring 208 is coiled. First and second longitudinally spaced-apart protuberances 210 and 212 are formed on the central portion of rod 204 and are adapted to engage rotatable control members 174 and 184 in the manner to prevent their rotation when the locking rod is in the starting position shown in FIG. 34. However, when a pushing force is exerted in a rearward direction on portion 204b of the locking rod in the manner shown in FIG. 47A, the locking rod will slide rearwardly within supporting sleeve 205 from its first locking position into the second unlocked position wherein protuberances 210 and 212 clear control knobs 174 and 184 so that they can be rotated by the treating physician to precisely preset the volume of each dose of medicament to be delivered and also to preset the required interval of time between doses. Upon a release of finger pressure on end portion 204b, spring 208 will automatically urge member 204 to return to the locking position.

Figure 44:
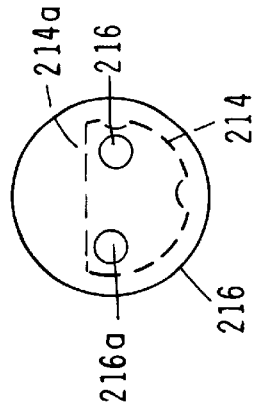
FIG. 44 is a rear view of the locking shaft of the locking means of the invention.
Figure 45:
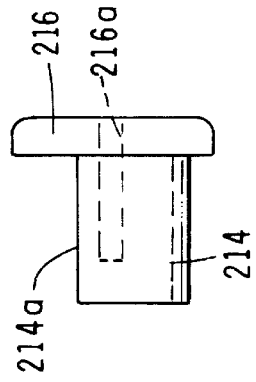
FIG. 45 is a side-elevational view of the locking shaft shown in FIG. 44.
Figure 46:
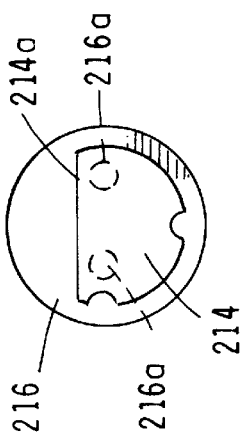
FIG. 46 is a front view of the locking shaft shown in FIG. 44.

Another very important feature of this latest form of the invention is the provision of key control means which function to control movement of the locking rod in the manner previously described to enable the setting of the dose volumes and time intervals between doses. Referring particularly to FIGS. 34A, 34B, 37, 40, and 41 through 46, this important key control means can be seen to comprise a locking assembly 211 which can be operated only by a physician key 112 of the character previously described. The locking assembly, which is rotatably mounted within sleeve 205 of the device housing 142, comprises an elongated body portion 214 and a head portion 216 which is connected thereto (FIGS. 44 through 46). Body portion 214 includes a flat 214a which is adapted to engage a shoulder 217 formed on locking rod 204. When flat 214a is in engagement with locking shoulder 217, rearward movement of the locking rod 204 is positively prevented. However when member 214 is rotated by a physician's key 112 (FIG. 1) to a position where flat 214a will clear shoulder 217 as shown in FIGS. 47A and 47E, the locking rod 204 can be moved rearwardly of the housing against the urging of spring 208 by pushing on the forward finger engaging portion 204b. In order to rotate member 214 within housing 205, it is necessary to insert the two spanner elements 112a formed on the physician's key (FIGS. 1, 18, and 19) into spaced-apart spanner element receiving openings 126a provided on a cap portion 216 of the locking assembly which is received over head portion 216 (see FIGS. 41, 42 and 43). When pins 112a are inserted into openings 216a and the assembly rotated, flat 214a can be moved into and out of engagement with shoulder 217 thereby either blocking or permitting inward movement of the locking assembly 204 relative to housing 142.

After control members 174 and 184 have been set and the locking rod released, spring 208 will return the locking rod to its initial position and the physician or other care giver can lock the locking rod in this locked position by rotating physician's key 112 into the locked position and then removing the key from the locking assembly. The setting made by the treating physician will then remain unchanged unless and until the physician unlocks the locking mechanism using the locking key 112.

After the dose volume control and the dose interval control means have been appropriately set by the physician or care giver, cap 148, which covers the outlet 146, is removed and a conventional delivery set is connected to the device by slipping a delivery tube over the forwardly extending, tubular connector 146c of dispensing portion 146b. This done, tear away sleeve 217 is removed from the forward portion 142a of the housing, as is a safety ring 217a, which prevents accidental rotation of forward portion 142a of the housing relative to the main body portion thereof With ring 217 removed, the body portion of the housing can be rotated relative to the forward portion 142a. This will cause hollow cannula 158 to pierce septum 156 thereby opening fluid communication between reservoir 152 and outlet port 146. As cannula 158 moves toward septum 156 a flexible bellows 219, which sealably encloses cannula 158, will collapse in the manner shown in FIG. 47A. An inward force on delivery member 166 will then cause the first dose of medicament to be dispensed in the manner previously discussed.

Turning next to FIGS. 50A through 54A, yet another form of the patient control infusion device of the present invention is there illustrated and generally designated by the numeral 220. This form of the invention is similar in many respects to the embodiments shown in FIGS. 34 through 49 and like numerals are used to identify like components.

More particularly, this latest embodiment of the invention comprises an elongated device housing 222 having an internal stop 224 and a fluid outlet which can be placed in fluid communication with a remote delivery site. The forward portion of the housing is of substantially an identical construction to housing 142 and, as before, houses a fluid container 150 having a fluid reservoir 152 for containing the fluid to be delivered. Fluid reservoir 152 has an outlet which is in fluid communication with the fluid outlet of device housing via a closure means, comprising a pierceable septum. As before, the septum is held in position on container 150 by a crimp ring and is pierceable by a hollow cannula which is mounted within a forward portion 222a of device housing 222. Wien the cannula has penetrated the septum the fluid outlet of the device is placed in fluid communication with vial reservoir 152 via a filter means or filter member identical to the previously identified member 164.

Figures 54, 54A:
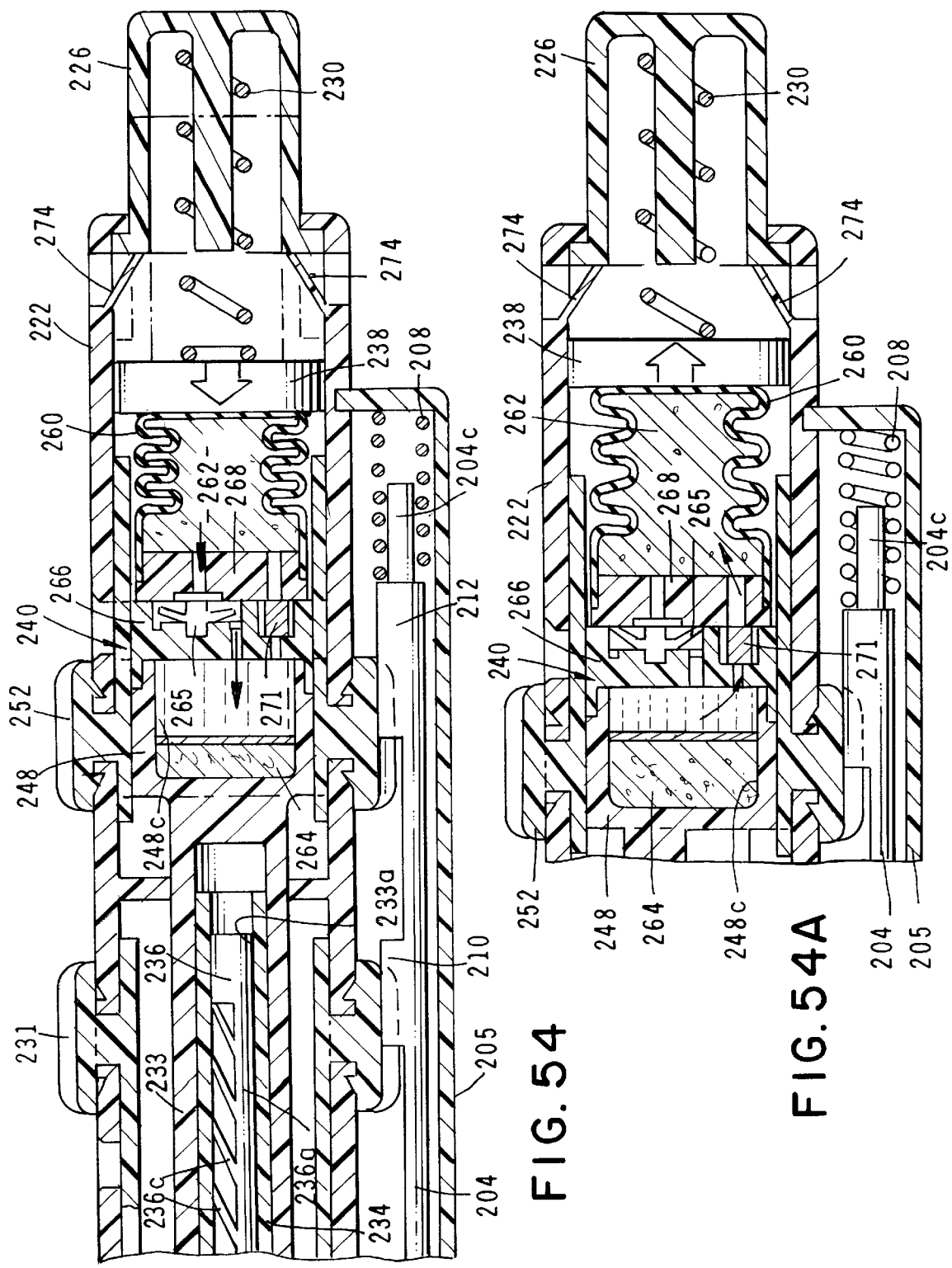
FIG. 54 is a fragmentary, side-elevational view similar to FIG. 50, but showing the position of the dose volume and dose interval control means after the device has been actuated by depressing the delivery member of the device.
FIG. 54A is a fragmentary cross-sectional view of the right-hand portion of FIG. 54 showing return of the dose interval control toward its starting position.

Manually operated dispensing means are connected to device housing 222 proximate the rearward portion 222c thereof. As before, the dispensing means functions to sequentially dispense multiple doses of fluid from the outlet of the device. As best seen in FIGS. 50B and 54, the dispensing means here comprises a generally cylindrically, shaped hollow dispensing member 226 which is telescopically receivable within an opening 227 provided in the rearward portion 222c of housing 222. Disposed within member 226 is a first biasing means, shown here as a coil spring 230, which yieldably resists inward movement of member 226.

Connected to the dispensing means is the important operating means of the invention, which functions to control the sequential dispensing of multiple doses of fluid from reservoir 152 of vial 150. This important operating means once again comprises two major control means, namely a dose interval control means for controlling the interval of time between the dispensing of each dose of medication and a dose volume control means for controlling the volume of each dose of medication to be delivered.

The dose volume control means of the present form of the invention is substantially identical to that shown in FIGS. 34 through 49 and includes a manually adjustable dose volume control member 231 which is rotatably mounted within device housing 222 and is rotatable by the treating physician or health care worker to preset the volume of the doses to be delivered to the patient. Member 231 is operably associated with an operating rod 232 which forms a part of an operating rod assembly generally designated in the drawings by the numeral 234. Operating rod assembly 234 also includes a dosing rod 236 which is similar in construction and operation to dosing rod 182 (FIG. 50A).

Figures 50A, 51A:
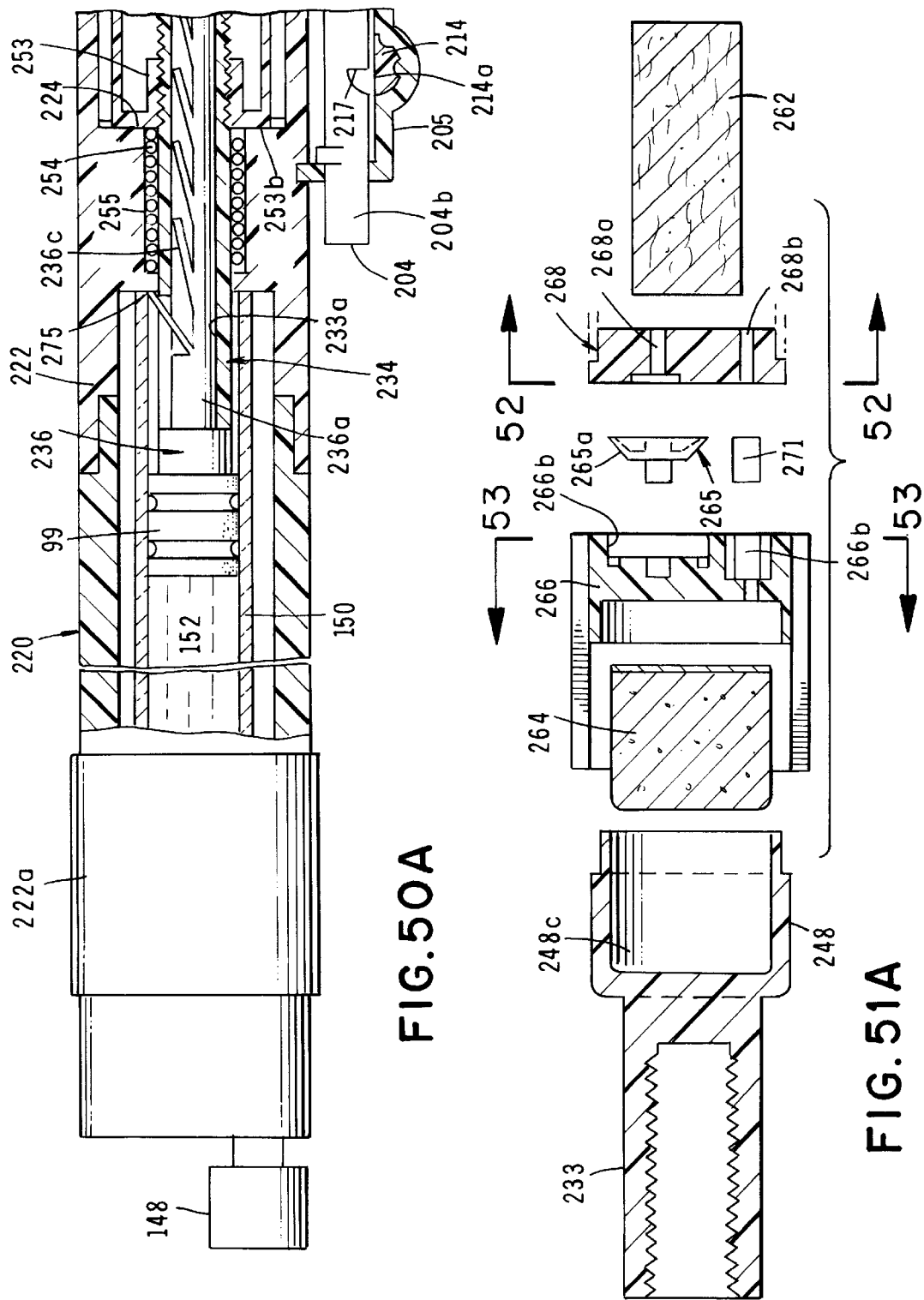

As best seen in FIGS. 50A and 54, dosing rod 236, has a shank portion 236a which is telescopically movable within an interior, generally cylindrical chamber 234b of an extension 234a the character of which will presently be described. As before, dosing rod 236 functions to cause fluid to flow outwardly from reservoir 152 of vial 150 when the dispensing member 226 of the dispensing means is pushed inwardly relative to housing 222. It is to be noted that biasing means, shown here as spring 235 continuously urges dosing rod 236 toward plunger 99.

Considering next the important dose interval control means of the invention, it is to be observed that an inward force exerted by the patient on dispensing member 226 will cause a forward, or inward movement, of a disk-like member 238 which is in operable engagement with dose interval control assembly 240. An inward movement of assembly 240 will, in turn, cause an inward movement of the operating rod assembly 234 and also will also cause a forward movement of dosing rod 236 as a result of one of a series of fins 236c formed on shank portion 236a of the dosing rod engaging operation rod assembly 234.

Referring particularly to FIGS. 50B and 54, it can be seen that a dose interval, drum-like member 248 is threadably connected via extension 234a to operating rod 232. Dose interval member 248 is, in turn, interconnected with a knob-like control member 252 by means of oppositely disposed splines 252a which extend therefrom and which are slidably receivable within oppositely disposed grooves provided in member 248 (see, for example, FIG. 49B of the earlier described embodiment).

With respect to the dose volume control means of the invention, a dose volume, drum-like member 253 is threadably receivable over threaded portion 232a of rod 232. Member 253 is, in turn, interconnected with previously identified dose volume control member 231 by means of a pair of oppositely disposed splines 231 a which are closely received within a pair of oppositely disposed slots 253a provided in member 253 (see, for example, FIG. 49 for a similar construction). With this arrangement, rotation of member 231 will cause member 253 to move to the right from a first starting position to a second operating position wherein the leading edge 253b of the member is spaced from stop shoulder 224 of device housing 222 by a selected distance.

With the novel arrangement described in the preceding paragraphs, when the dispensing member 226 is pushed inwardly of housing 222, which also causes the operating rod assembly to move inwardly or forwardly of device housing 222, forward travel of the operating rod assembly will be stopped when the leading edge 253b of member 253 engages stop shoulder 224 provided on device housing 222 (see FIG. 50A). It is also to be observed that member 253 is in constant engagement with a coil spring 254 which is housed within a counterbore 255 provided in the forward portion of housing 222. Spring 254 forms a part of the second biasing means of the invention and functions to continuously urge rearward movement of the operating means, or operating rod assembly, rearwardly of housing 222. It is also to be observed that, when the dispensing member 226 is pushed inwardly of housing 222 a flange 226a formed on member 226 will engage disk-like member 238 which is disposed within housing 222 in engagement with a bellows-like compressible member 260. Disposed within bellows 260 is a fluid containing, sponge-like cellular mass 262 which is similar to mass 79 of the first described embodiment of the invention. Inward movement of member 226 and disk 238 will compress both bellows 260 and mass 262.

A sponge-like mass 264, which is disposed within chamber 248c of member 248, comprises a yieldably deformable component which is somewhat similar to member 77 of the first described embodiment. Mass 264 functions as an energy source when compressed, while cellular mass 262 comprises a fluid containing sponge-like structure which can be saturated with any suitable operating fluid such as glycerin or flourinated oil. Disposed intermediate masses 262 and 264 are first and second flow control means. In this latest form of the invention, the first flow control means comprises a check valve 265 which functions to permit fluid flow only in a direction toward yieldably deformable mass 264 and functions to block fluid flow in an opposite direction (see FIG. 51A). The second flow control means here functions to precisely control the rate of fluid flow in an opposite direction from chamber 248c toward the fluid containing sponge-like mass 262.

In operation of the apparatus of this latest form of the invention, an inward movement by the patient of dispensing member 226 relative to housing 222 will result in the concomitant inward movement of disk 238. As disk 238 moves inwardly, it will act on bellows 260 causing it to collapse and, at the same time, causing controlled compression of liquid containing, sponge-like mass 262. As mass 262 is compressed, the fluid contained therewithin will be forced therefrom through the first flow control means or valve 265 and thence into chamber 248c of member 248. As the fluid flows under pressure into chamber 248c via the first flow control means, it will compressively deform yieldably deformable mass 264 into the configuration shown in FIG. 54.

As best seen in FIG. 51A, check valve 265 is here provided in the form of a conventional umbrella type check valve which is captured between first and second flow control members 266 and 268 which are disposed within housing 222 in the manner indicated in FIGS. 50B and 51A. As best seen in FIG. 51A, flow control member 268 is provided with spaced-apart fluid flow passageways 268a and 268b while member 266 is provided with spaced passageways 266a and 266b (see also FIG. 53). Umbrella check valve 265 is strategically positioned between members 266 and 268 so that the flexible, skirt-like portion 265a of the valve will seal against member 268 and will deflect outwardly within a chamber 266c formed in member 266 in response to fluid flowing through passageways 268a thereby permitting the fluid to flow into fluid collector ring 266d, into passageways 266a and thence into chamber 248c. However, the construction of the umbrella-type check valve is such that the resilient skirt-like portions 265a of the valve will effectively function to prevent fluid flow in the opposite direction, that is, toward passageway 268a.

To permit fluid flow in a direction from chamber 248c toward cellular mass 262, a rate control means, or porous frit 271 is disposed within passageway 266b. Passageway 266b communicates with passageway 268b so that fluid can flow from chamber 248c toward cellular mass 262 via the second flow control means or porous frit 271.

It is apparent that the degree of compression of cellular mass 262 is controlled by the position of member 248 on the threaded shank portion of rod 232. This position of member 248 is, in turn, controlled by the extent of rotation by the treating physician of control member 252 relative to housing 222. Obviously, the greater the compression of cellular mass 262 the greater will be the expulsion therefrom of the fluid contained therein and the greater will be the compression of elastomeric member 264. The greater the compression of member 264 and the greater the volume of fluid within chamber 248c the greater will be the time required for the fluid to flow through frit 271 due to the urging of member 264 and the longer will be the time for disk 238 to return to its starting position. Conversely, the lessor the degree of compression of mass 262, the shorter will be the time required for disk 238 to return to its starting position. In a manner presently to be described, the degree of compression of mass 262 will control the time interval at which subsequent doses of liquid medicament can be dispensed from reservoir 152.

In order to dispense medication from the apparatus of the invention, the delivery member 226 must be pushed inwardly of housing 222. As member 226 is pushed inwardly by the patient, the operating rod assembly 232 will also move forwardly of the housing. When the delivery member is released, spring 254 will function to urge the operating rod assembly to return to its starting position. Similarly, as dispensing member 226 is depressed, spring 230 which is housed therein will be compressed so that, upon release of member 226, spring 230 will tend to rapidly return member 226 to the position shown in FIG. 54A wherein it is locked against further inward movement by resilient locking tabs 274 which are provided on housing 222 and which here comprise the delay means of this latest form of the invention. However, while the dispensing member will immediately return to its starting position upon its release, the dose interval control means does not do so. Rather, the return of the dose interval control means, is uniquely a function of the rate of fluid flow through rate control frit 271 in the manner indicated in FIG. 54A.

As the fluid returns to mass 262, it will expand toward its starting position, (see FIG. 54A) and will urge disk 238 rearwardly into camming engagement with locking tabs 274 moving them once again into the unlocked position shown in figure 50B. The time required for disk 238 to return to its starting position equates to the delay time between possible sequential delivery of the doses of medication.

An important feature of the apparatus of this latest form of the invention is the previously described dosing rod restraining and advancing means which functions to position and advance the dosing rod 236 of the dispensing means relative to housing 222. These novel means, which comprise the previously identified resiliently deformable fins 236c, function in the same manner as described in the embodiment of the invention shown in FIGS. 34 through 48. More particularly, once the dosing rod is advanced by the operating rod, it will be restrained in its advanced position as a result of one of the fins engaging a locking shoulder 275 provided interiorly of housing 222 and will be locked in this advanced position even when the operating rod assembly returns to its starting position upon release of dispensing member 226. Upon the second depression of dispensing member 226, the leading edge of operating rod will engage a selected outwardly extending fin and in so doing will urge further forward travel of the dosing rod inwardly of the container 150.

As in the earlier described embodiment of the invention, this second embodiment is specially designed so that the dose interval control means and the dose volume control means can be preset only by an authorized person such as the treating physician. For this purpose, locking means and key control means, which are identical in construction and operation to those described in connection with the device shown in FIGS. 34 through 48, are provided for preventing rotation of control knobs 231 and 252 unless and until a locking rod 204, which comprises a part of the locking means, is moved from the first starting position to a second operating position through use of the key control means. As best seen in FIGS. 50A and 50B, the locking rod 204 here comprises an elongated member that is mounted within housing 222 for sliding movement within a sleeve-like support 205 formed on housing 222 against the urging of a biasing means which is here provided in the form of a coil spring 208. Locking rod 204 includes an elongated shank portion 204a, a forward finger-engaging portion 204b, and an end portion 204c which includes a reduced diameter shaft-like portion about which spring 208 is coiled. First and second spaced-apart protuberances 210 and 212 are formed on the central portion of rod 204 and are adapted to engage rotatable control members 231 and 252 in the manner to prevent their rotation when the locking rod is in the starting position shown in FIG. 50A. However, when a pushing force is exerted in a rearwardly direction on portion 204b of the locking rod, the locking rod will slide within supporting sleeve 205 from its first locking position into the second unlocked position wherein control knobs 231 and 252 can be rotated by the treating physician to precisely preset the volume of each dose of medicament to be delivered also to preset the permitted interval between doses. Upon a release of finger pressure of end portion 204b, spring 208 will automatically urge member 204 to return to the locking position. In this position, the key control means can be used to prevent further adjustment of knobs 231 and 252.

Turning next to FIGS. 55A through 62, another form of the patient control infusion device of the present invention is there illustrated and generally designated by the numeral 280. This form of the invention is similar in many respects to the embodiments shown in FIGS. 50 through 54A and, once again, like numerals are used to identify like components. This latest embodiment of the invention also comprises an elongated, in-line device housing 282 having an internal stop 284 and a fluid outlet 285 which can be placed in fluid communication with a remote delivery site after removal of a closure cap 287. The forward portion of the housing is of a similar construction to that of housing 222 and comprises a forward portion 282a, which carries a hollow cannula 288. As before, forward portion 282a is threadably interconnected with the main body portion of the housing. The device housing 282 houses a fluid container 150 having a fluid reservoir 152 for containing the fluid to be delivered. Fluid reservoir 152 has an outlet 154 which is in fluid communication with the fluid outlet of device housing via cannula 288 and a closure means, comprising a pierceable septum 156. Septum 156 is held in position on container 150 by a crimp ring 150c and is pierceable by a hollow cannula 288 when forward portion 282a is rotated relative to the main body in a manner to move to the right as viewed in FIG. 55A. When cannula 288 has penetrated septum 156 fluid outlet 285 is placed in fluid communication with vial reservoir 152 via a filter means or filter member 290.

Once again, manually operated dispensing means are connected to device housing 282 proximate the rearward portion 282b thereof. As before, the dispensing means functions to sequentially dispense multiple doses of fluid from the outlet of the device. As best seen in FIGS. 55B and 60A, the dispensing means here comprises a generally cylindrically, shaped hollow dispensing member 292 which is telescopically receivable within an opening 293 provided in the rearward portion 282b of housing 282. Disposed within member 292 is a first biasing means, shown here as a coil spring 294, which yieldably resists inward movement of member 292.

Connected to the dispensing means is the important operating means of the invention, which functions to control the sequential dispensing of multiple doses of fluid from reservoir 152 of vial 150. As before, this important operating means comprises two major control means, namely a dose interval control means for controlling the interval of time between the dispensing of each dose of medication and a dose volume control means for controlling the volume of each dose of medication to be delivered.

The dose volume control means of this latest form of the invention is similar to that shown in FIGS. 50 through 54 and includes a manually adjustable dose volume control member 296 which is rotatably carried by device housing 282 and is rotatable by the treating physician or health care worker to preset the volume of the doses to be delivered to the patient. Member 296 is operably associated with an operating rod 298 which forms a part of an operating rod assembly generally designated in the drawings by the numeral 300. Operating rod assembly 300 also includes a threaded coupler 302 and a dosing rod 304 (FIGS. 55A and 59) which is similar in construction and operation to dosing rod 236. Coupler 302 has a rectangular shaft portion 302b (FIGS. 57 and 62) which prevents its rotation relative to a web like partition 303 formed in device housing 282.

Figure 55A:
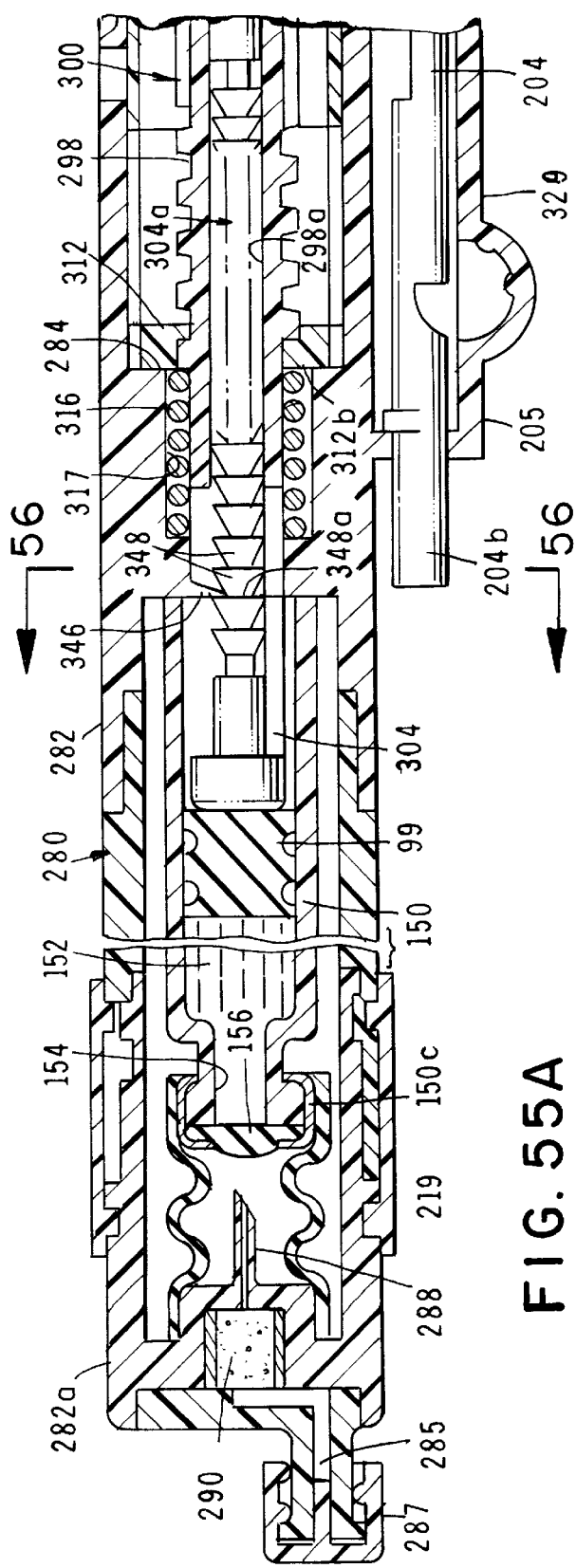
Figure 56:
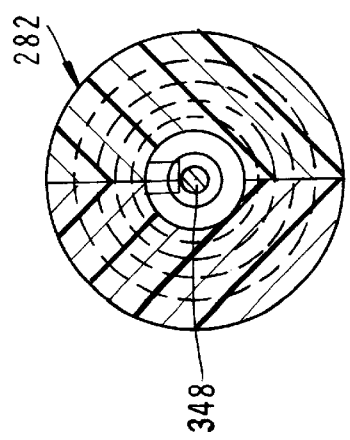
FIG. 56 is a cross-sectional view taken along lines 56—56 of FIG. 55A.

As best seen in FIG. 55A, dosing rod 304, has a shank portion 304a which is telescopically movable within an interior, generally cylindrical chamber 298a of operating rod 298. As before, dosing rod 304 acts on plunger 99 to cause fluid to flow outwardly from reservoir 152 of vial 150 when the dispensing member of the dispensing means is pushed inwardly relative to housing 282 (see FIG. 55A).

With respect to the dispensing means of the invention, this means is also quite similar to that described in connection with FIGS. 50 through 54 and an inward force exerted by the patient on dispensing member 292 will cause a forward, or inward movement, of a cup-like member 306 which is in operable engagement with dose interval control assembly 310. An inward movement of assembly 310 will cause an inward movement of operating rod assembly 300 and also will also cause a forward movement of dosing rod 304 as result of assembly 300 acting on the inboard extremity 304a of dosing rod 304.

Figure 59:
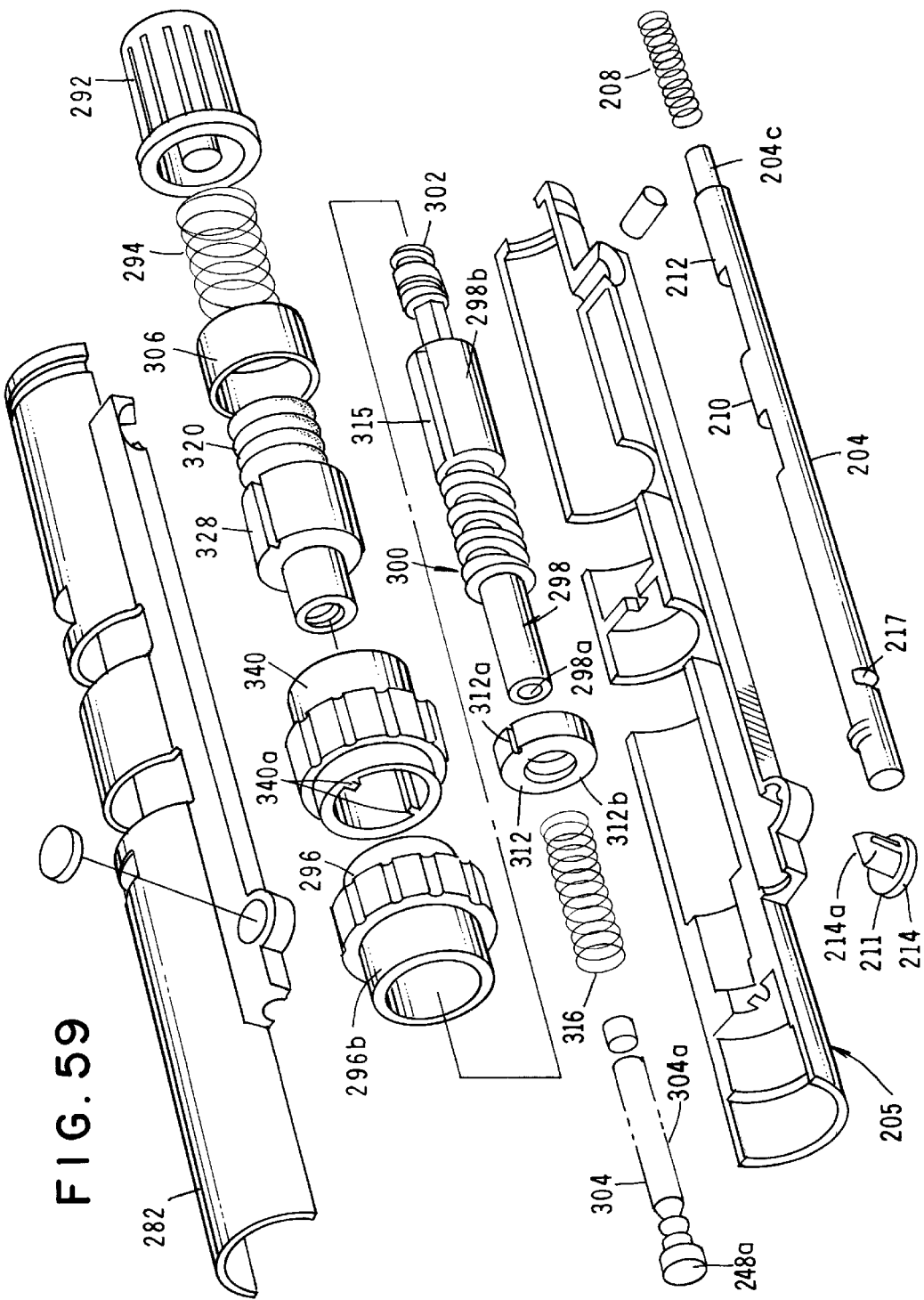
FIG. 59 is a generally perspective, exploded view of the form of the apparatus shown in FIGS. 55A and 55B.

Referring particularly to FIGS. 55A and 59, it can be seen that a dose volume control disk-like stop member 312 is threadably connected to operating rod 298. Spline grooves 312a formed in stop member 312 receive splines 296a formed on knob-like control member and ride therein as the stop member rides up the threads as the operating rod is rotated by control member 298. The splines 296a of the control member are also receivable within grooves 315 formed in an enlarged diameter portion 298b of operating rod 298 (see FIG. 59). With the construction thus described, rotation of member 296 will cause stop member 312 to move to the right from a first starting position to a second operating position wherein the leading face 312b of the stop member is spaced from stop shoulder 284 of device housing 282 by a selected distance.

With the novel arrangement described in the preceding paragraphs, when the dispensing member 292 is pushed inwardly of housing 282, which also causes the operating rod assembly to move inwardly or forwardly of device housing 282, forward travel of the operating rod assembly will be stopped when face 312b of stop member 312 engages the stop shoulder 284. Stop member 312 is in continuous engagement with a coil spring 316 which is housed within a counterbore 317 provided in the forward portion of housing 282. Spring 316 forms a part of the second biasing means of the invention and functions to continuously urge rearward movement of the operating means, or operating rod assembly, rearwardly of housing 282.

It is also to be observed that, when the dispensing member 292 is pushed inwardly of housing 282 a flange 292a formed on member 292 will engage cup-like member 306 which is disposed within housing 282 in engagement with a bellows-like compressible member 320. Disposed within bellows 320 is a fluid containing sponge-like cellular mass 322 which is similar to mass 262 of the previously described embodiment. Inward movement of member 292 and member 306 will compress both bellows 320 and mass 322. In addition, an elastomeric member 324, which is housed within a chamber 326 formed in the enlarged diameter portion 328a of a closed interval drum-like member 328 which is threadably connected to coupler shaft 302 (see FIGS. 61 and 62). Elastomeric member 324 as well as coil spring 294 resists inward movement of member 292.

Elastomeric, sponge-like member 324 comprises a yieldably deformable component which is similar to member 264 of the last described embodiment and functions as an energy source when compressed. On the other hand, cellular mass 322, like member 262, comprises a fluid containing sponge-like structure which can be saturated with any suitable operating fluid such as glycerin or flourinated oil. Disposed intermediate masses 322 and 324 are first and second flow control means of the general character previously described. More particularly, as best seen in figure 61, this latest form of the invention, the first flow control means comprises a check valve 332 which functions to permit fluid flow only in a direction toward yieldably deformable mass 324 and functions to block fluid flow in an opposite direction. The second flow control means shown here as a porous flit 337 here functions to precisely control the rate of fluid flow in an opposite direction toward the fluid containing sponge-like mass 322.

In operation of the apparatus of this latest form of the invention, an inward movement by the patient of dispensing member 292 relative to housing 282 as shown in FIG. 60B will result in the inward movement of cup-like member 306. As member moves inwardly, it will act on bellows 320 causing it to collapse and, at the same time, causing controlled compression of liquid containing, sponge-like mass 322. As mass 322 is compressed, the fluid contained therewithin will be forced therefrom through the first flow control means and thence into chamber 326 of member 328 in the direction of the arrows of FIG. 60B. As the fluid flows under pressure into chamber 326 via the first flow control means, it will compressively deform yieldably deformable mass 324 in the manner shown in FIG. 60B.

The first flow control means or check valve 332 is here provided in the form of an umbrella type check valve which is captured between first and second flow control members 334 and 336 which are disposed within housing 328 in the manner indicated in FIGS. 55B and 60A. As best seen in FIG. 61 flow control member 334 is provided with spaced-apart fluid flow passageways 334a, 334b, and 334c, while member 336 is provided with a central cavity 336a and a control passageway 336b. Umbrella check valve 332 is strategically positioned between members 334 and 336 so that the flexible, skirt-like portion 332a of the valve will deflect outwardly within chamber 334d in response to fluid flowing through passageway 336b thereby permitting the fluid to flow into fluid passageways 334a and 334b and thence into chamber 326. However, the construction of the umbrella-type check valve is such that the resilient skirt-like portions 332a of the valve will effectively function to prevent fluid flow in the opposite direction, that is, toward passageway 336b.

To permit fluid flow in a direction from chamber 326 toward cellular mass 322, the rate control means, or porous frit 337 is disposed within a central passageway 332b formed in the umbrella valve. Passageway 336b communicates with passageway 334c via frit 337 so that fluid can flow from chamber 326 toward cellular mass 322 via the second flow control means or porous frit 337.

It is apparent that the degree of compression of cellular mass 322 is controlled by the position of member 328 on the threaded shank portion 302a of coupling shank 302. This position of member 328 is, in turn, controlled by the extent of rotation by the treating physician of a control member 340 relative to housing 282. As shown in FIGS. 59 and 60B, as member 340 is rotated, member 328, which is operably coupled therewith by splines 340a, will move to the right partially compressing member 322 and causing the fluid contained therewithin to flow into chamber 326. This fluid flow will compress member 324 so that the components of the dose interval control means are in the configuration shown in FIG. 60A. Obviously, the greater the overall compression of member 322 upon pressing the dispensing member 292 inwardly, the greater will be the volume of fluid within chamber 326 and the greater will be the time required for the fluid to flow through frit 337 due to the urging of member 324 and the longer will be the time for cup-like member 306 to return to its starting position. Conversely, the lessor the degree of compression of mass 322 due to the rotation of control member 340, the lesser will be the overall compression of member 322 due to the inward pressing of member 292 and the lesser will be the amount of fluid forced into chamber 326 and the shorter will be the time required for member 306 to return to its starting position. As before, the degree of compression of mass 322 will control the time interval at which subsequent doses of liquid medicament can be dispensed from reservoir 152.

In order to dispense medication from the apparatus of the invention, the delivery member 292 must be pushed inwardly of housing 282 in the manner shown in FIG. 60B. As member 292 is pushed inwardly by the patient, the operating rod assembly 298 will also move forwardly of the housing. When the delivery member is released, spring 316 will urge the operating rod assembly to move toward its starting position. Similarly, as dispensing member 292 is depressed spring 294 which is housed therein will be compressed so that, upon release of member 292, spring 294 will tend to rapidly return member 292 to the position shown in FIG. 60C where it is locked against further inward movement by resilient locking tabs 342 which are provided on housing 282 and which here comprise a part of the delay means of this latest form of the invention. While the dispensing member will immediately return to its starting position upon its release, the dose interval control means does not do so. Rather, as before, the return of the dose interval control means, is uniquely a function of the rate of fluid flow through rate control frit 337.

As the fluid returns to mass 322, it will expand toward its starting position, and will urge cup-like member 306 rearwardly into camming engagement with locking tabs 342 moving them once again into the unlocked position shown in FIG. 60A. The time required for member 306 to return to its starting position, of course, equates to the delay time between possible sequential delivery of the doses of medication.

The apparatus of this latest form of the invention also includes dosing rod restraining means which function to position the dosing rod 304 of the dispensing means relative to housing 282. This restraining means here comprises a resiliently deformable finger 326 which is connected to housing 282 and extends inwardly thereof toward dosing rod 304 (FIG. 55A). With this construction, once the dosing rod is advanced by the operating rod, it will be restrained in its advanced position as a result of finger 346 engaging a shoulder 348a provided on a selected one of a plurality of teeth-like protuberances 348 formed on the shank portion of dosing rod 304 (see FIG. 55A). Upon the second depression of dispensing member 292, the enlarged diameter head portion 302a of coupling shaft 302 will engage the dosing rod to move it further inwardly of the container 150.

As in the earlier described embodiments of the invention, this latest embodiment is also specially designed so that the dose interval control means and the dose volume control means can be preset only by an authorized person such as the treating physician. For this purpose, locking means and key control means, which are identical in construction and operation to those described in connection with the device shown in FIGS. 34 through 48, are provided for preventing rotation of control knobs 296 and 340 unless and until a locking rod 204, which comprises a part of the locking means, is moved from the first starting position to a second operating position. As best seen in FIG. 59, the locking rod 204 here comprises an elongated member that is mounted within a sleeve-like support 205 formed on housing 282 against the urging of a biasing means which is here provided in the form of a coil spring 208. As before, locking rod 204 includes an elongated shank portion 204a, a forward finger-engaging portion 204b, and an end portion 204c which includes a reduced diameter shaft-like portion about which spring 208 is coiled. First and second space-apart protuberances 210 and 212 are formed on the central portion of rod 204 and are adapted to engage rotatable control members 296 and 340 in the manner to prevent their rotation when the locking rod is in its starting position. However, when a pushing force is exerted in a rearwardly direction on portion 204b of the locking rod, the locking rod will slide within supporting sleeve 205 from its first locking position into the second unlocked position wherein control knobs 296 and 340 can be rotated by the treating physician to precisely preset the volume of each does of medicament to be delivered also to preset the permitted interval between doses. Upon a release of finger pressure of end portion 204b, spring 208 will automatically urge member 204 to return to the locking position.

This latest form of the invention also includes disabling means for disabling the apparatus. This disabling means here comprises a disabling button 350 which is telescopically movable within a bore 352 formed in housing 205 (FIGS. 55B and 60A). When button 350 is pushed inwardly, the inboard end thereof will block forward movement of cup-like member 360 thereby preventing inward movement of dispensing member 292. (See phantom lines in FIG. 60A).

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

What is claimed is:

1. A patient controlled infusion device for the sequential delivery of discrete doses of fluid to a delivery site comprising:
   (a) a device housing having a fluid outlet adapted to be in communication with the delivery site;
   (b) a fluid reservoir disposed within said device housing for containing the fluid to be delivered, said fluid reservoir having an outlet in communication with said fluid outlet of said housing;
   (c) dispensing means for sequentially dispensing first and second doses of fluid from said outlet of said fluid reservoir; and
   (d) an operating and control means operably associated with said dispensing means for controlling the dispensing of fluid from said fluid reservoir, said operating and control means comprising:

(i) dose interval control means for controlling the interval of time between the dispensing of the discrete doses of fluid to the delivery site, said dose interval control means comprising an adjustable dose interval control member carried by said device housing, said dose interval control means further comprising a fluid containing cellular mass, a compressible member operably associated with said fluid containing cellular mass and a fluid flow control means operably associated with said fluid containing cellular mass for controlling fluid flow therefrom; and (ii) dose volume control means for controlling of the volume of said discrete doses of fluid, said dose volume control means comprising an adjustable dose volume control member carried by said device housing.

2. The device as defined in claim 1 further including first locking means for preventing adjustment of said dose interval control member and said dose volume control member.

3. A device as defined in claim 2 in which said dispensing means comprises:

(a) a patient operated delivery mechanism connected to said device housing for movement between first and second positions;

(b) an operating rod assembly connected to said delivery mechanism for movement within said device housing between first and second locations; and (c) a plunger disposed within said fluid reservoir for movement therewithin by movement of said operating rod assembly to cause delivery of fluid to the delivery site.

4. The device as defined in claim 3 in which said operating rod assembly includes an operating rod movable between first and second locations and in which said operating and control means further comprises first biasing means for urging said operating rod toward said first position.

5. A patient controlled infusion device for the sequential delivery of discrete doses of fluid to a delivery site comprising:

(a) a device housing having a fluid outlet adapted to be in communication with the delivery site;

(b) a fluid reservoir disposed within said device housing for containing the fluid to be delivered, said fluid reservoir having an outlet in communication with said fluid outlet of said housing;

(c) dispensing means for sequentially dispensing first and second doses of fluid from said outlet of said fluid reservoir, said dispensing means comprising:

(i) a patient operated delivery mechanism connected to said device housing for movement between first and second positions;

(ii) an operating rod assembly connected to said delivery mechanism for movement within said device housing between first and second locations, said operating rod assembly comprising an operating rod movable between first and second locations, said operating rod having first and second threaded segments; and (iii) a plunger disposed within said fluid reservoir for movement therewithin by movement of said operating rod assembly to cause delivery of fluid to the delivery side;

(d) an operating and control means operably associated with said dispensing means for controlling the dispensing of fluid from said fluid reservoir, said operating and control means comprising:

(i) dose interval control means for controlling the interval of time between the dispensing of the discrete doses of fluid to the delivery site, said dose interval control means comprising a manually adjustable dose interval control member carried by said device housing, dose interval control means comprising a member threadably connected to said first threaded segment for movement along said operating rod between first and second locations; and (ii) dose volume control means for controlling of the volume of said discrete doses of fluid, said dose volume control means comprising a manually adjustable dose volume control member carried by said device housing for moving said first threaded segment along said operating rod between first and second locations; and (iii) first biasing means for urging said operating rod toward said first position; and (e) first locking means for preventing adjustment of said dose interval control member and said dose volume control member.

6. The device as defined in claim 5 in which said volume dose interval control means further comprises a member threadably connected to said second threaded segment of said operating rod for movement along said operating rod between first and second locations by said adjustable volume control member.

7. A device as defined in claim 6 in which said dose interval control means further includes a compressible member compressible by movement of said patient operated delivery mechanism toward said second position.

8. The device as defined in claim 6 in which said dose interval control means further includes:

(a) a first hollow housing operably associated with said dispensing means, said first hollow housing having a first chamber; and (b) a cellular fluid containing mass disposed within said first chamber of said hollow housing, said fluid containing mass being compressible by movement of said patient operated delivery mechanism toward said second position.

9. A device as defined in claim 8 in which said dose interval control means further comprises:

(a) a second hollow housing operably associated with said operating rod assembly, said second hollow housing having a chamber; and (b) a yieldably deformable mass disposed within said second chamber of said second hollow housing.

10. The device as defined in claim 9 in which said dose interval control means further comprises:

(a) first flow control means mounted within said device housing intermediate said yieldably deformable mass and said fluid containing mass for controlling fluid flow toward said yieldably deformable mass; and (b) second flow control means mounted within said device housing intermediate said yieldably deformable mass and said fluid containing mass for controlling fluid flow in a direction toward said fluid containing mass.

11. The device as defined in claim 10 in which said dispensing means further includes second biasing means for yieldably resisting movement of said patient operated delivery mechanism toward said second position.

12. The device as defined in claim 11 in which said dispensing means further includes locking means for preventing movement of said patient operated delivery mechanism toward said second position.

13. The device as defined in claim 12 in which said dispensing means further includes release means operably associated with said locking means for releasing said locking means to permit movement of said patient operated delivery mechanism toward said second position.

14. A patient controlled infusion device for the sequential delivery of discrete doses of fluid to a delivery site comprising:
(a) a device housing having a stop and a fluid outlet adapted to be in communication with the delivery site;
(b) a fluid reservoir disposed within said device housing for containing the fluid to be delivered, said fluid reservoir having an outlet in communication with said fluid outlet of said housing;
(c) dispensing means for sequentially dispensing first and second doses of fluid from said fluid outlet of said fluid reservoir, said dispensing means comprising:
  (i) a patient operated delivery mechanism connected to said device housing for movement between first and second positions; and
  (ii) an operating rod connected to said delivery mechanism for movement within said device housing between first and second locations; and
(d) operating and control means operably associated with said dispensing means for controlling the dispensing of fluid from said fluid reservoir, said operating and control means comprising:
  (i) dose interval control means for controlling the interval of time between dispensing of the discrete doses of fluid to the delivery site, said dose interval control means comprising a manually adjustable, dose interval control member rotatably carried by said device housing, said dose interval control means further comprising a fluid containing cellular mass, a compressible member operably associated with said fluid containing cellular mass, and a fluid flow control means disposed between said fluid containing cellular mass and said compressible member for controlling fluid flow therebetween; and
  (ii) dose volume control means for controlling the volume of said discrete doses of fluid, said dose volume control means comprising a manually adjustable, dose volume control member rotatably carried by said device housing.

15. The device as defined in claim 14 in which said dispensing means further includes means for compressing said fluid containing cellular mass upon said patient operated delivery mechanism being moved toward said second position.

16. A patient controlled infusion device for the sequential delivery of discrete doses of fluid to a delivery site comprising:
(a) a device housing having a stop and a fluid outlet adapted to be in communication with the delivery site;
(b) a fluid reservoir disposed within said device housing for containing the fluid to be delivered, said fluid reservoir having an outlet in communication with said fluid outlet of said housing;
(c) dispensing means for sequentially dispensing first and second doses of fluid from said outlet of said fluid reservoir, said dispensing means comprising:
  (i) a patient operated delivery mechanism connected to said device housing for movement between first and second positions;
  (ii) an operating rod connected to said delivery mechanism for movement within said device housing between first and second locations; and
  (iii) locking means for preventing movement of said patient operated delivery mechanism toward said second position; and
(d) operating and control means operably associated with said dispensing means for controlling of the dispensing of fluid from said fluid reservoir, said operating and control means comprising:
  (i) dose interval control means for controlling the interval of time between dispensing of the discrete doses of fluid to the delivery site, said dose interval control means comprising a manually adjustable, dose interval control member rotatably carried by said device housing; and further comprising a fluid containing cellular mass, a compressible member operably associated with said fluid containing cellular mass and fluid flow control means disposed between said fluid containing cellular mass and said compressible member for controlling fluid flow therebetween
  (ii) dose volume control means for controlling of the volume of said discrete doses of fluid, said dose volume control means comprising a manually adjustable, dose volume control member rotatably carried by said device housing.

17. The device as defined in claim 16 in which said dispensing means further includes first biasing means for yieldably resisting movement of said operating and control means toward said second location.

18. The device as defined in claim 16 in which said dispensing means further includes second biasing means for yieldably resisting movement of said patient operated delivery mechanism toward said second position.

19. A patient controlled infusion device for the sequential delivery of discrete doses of fluid to a delivery site comprising:
(a) a device housing having a stop and a fluid outlet adapted to be in communication with the delivery site;
(b) a fluid reservoir disposed within said device housing for containing the fluid to be delivered, said fluid reservoir having an outlet in communication with said fluid outlet of said housing;
(c) dispensing means for sequentially dispensing first and second doses of fluid from said outlet of said fluid reservoir, said dispensing means comprising:
  (i) a patient operated delivery mechanism connected to said device housing for movement between first and second positions;
  (ii) an operating rod connected to said delivery mechanism for movement within said device housing between first and second locations;
  (iii) a plunger disposed within said fluid reservoir for movement between first and second positions; and
  (iv) a dosing rod operably associated with said operating rod for movement thereby between first and second locations to move said plunger toward said second position upon said operating rod being moved toward said second location; and
(d) operating and control means operably associated with said dispensing means for controlling of the dispensing of fluid from said fluid reservoir, said operating and control means comprising:
  (i) dose interval control means for controlling the interval of time between dispensing of the discrete doses of fluid to the delivery site, said dose interval control means comprising a manually adjustable, dose interval control member rotatably carried by said device housing, said dose interval control means further including a fluid containing cellular mass and a compressible member operably associated with said fluid containing cellular mass; and (ii) dose volume control means for controlling of the volume of said discrete doses of fluid, said dose volume control means comprising a manually adjustable, dose volume control member rotatably carried by said device housing.

20. A patient controlled infusion device for the sequential delivery of discrete doses of fluid to a delivery site comprising:

(a) a device housing having a stop and a fluid outlet adapted to be in communication with the delivery site;

(b) a fluid reservoir disposed within said device housing for containing the fluid to be delivered, said fluid reservoir having an outlet in communication with said fluid outlet of said housing;

(c) dispensing means for sequentially dispensing first and second doses of fluid from said outlet of said fluid reservoir, said dispensing means comprising:

(i) a patient operated delivery mechanism connected to said device housing for movement between first and second positions;

(ii) an operating rod connected to said delivery mechanism for movement within said device housing between first and second locations; and (iii) restraining means associated with said operating rod for restraining said operating rod in said second location;

(d) operating and control means operably associated with said dispensing means for controlling of the dispensing of fluid from said fluid reservoir, said operating and control means comprising:

(i) dose interval control means for controlling the interval of time between dispensing of the discrete doses of fluid to the delivery site, said dose interval control means comprising a manually adjustable, dose interval control member rotatably carried by said device housing, said dose interval control means further comprising a fluid containing cellular mass and a compressible member operably associated with said fluid containing cellular mass; and (ii) dose volume control means for controlling of the volume of said discrete doses of fluid, said dose volume control means comprising a manually adjustable, dose volume control member rotatably carried by said device housing; and (e) locking means carried by said device for preventing rotation of said manually adjustable dose interval control member and said dose volume control member.

21. A patient controlled infusion device for the sequential delivery of incremental doses of fluid to a delivery site comprising:

(a) a device housing having a body portion having a stop and a forward portion connected to said body portion, said forward portion having a fluid outlet in communication with a hollow cannula connected to said forward portion;

(b) a container having a fluid reservoir disposed within said device housing for containing the fluid to be delivered, said fluid reservoir being closed by a septum pierceable by said hollow cannula to place said reservoir in communication with said fluid outlet of said forward portion;

(c) dispensing means for sequentially dispensing first and second doses of fluid from said fluid reservoir, said dispensing means comprising:

(i) a patient operated delivery mechanism connected to said device housing for movement between first and second positions;

(ii) an operating rod assembly connected to said delivery mechanism for movement within said device housing between first and second locations;

(iii) a plunger telescopically movable within said fluid reservoir by said operating rod assembly; and (d) operating means operably associated with said dispensing means for controlling the dispensing of fluid from said fluid reservoir, said operating means comprising:

(i) dose interval control means for controlling the interval of time between dispensing of the sequential doses of fluid to the delivery site, said dose interval control means comprising a fluid containing cellular mass, a compressible member operably associated with said fluid containing cellular mass, a manually adjustable dose interval control member rotatably carried by said device housing and fluid flow control means disposed between said fluid containing cellular mass and said compressible member for controlling fluid flow therebetween; and (ii) dose volume control means for controlling the volume of said incremental doses of fluid, said dose volume control means comprising a manually adjustable dose volume control member rotatably carried by said device housing.

22. A device as defined in claim 21 in which said flow control means comprises:

(a) a check valve for permitting fluid flow in a direction toward said compressible member, but blocking fluid flow in an opposite direction; and (b) a porous frit for controlling the rate of fluid flow in a direction toward said fluid containing cellular mass.

23. A device as defined in claim 21 in which said operating rod assembly comprises an operating rod having first and second threaded segments and a dosing rod operably associated with said operating rod.

24. A device as defined in claim 23 in which said dose interval control means further comprises a member threadably connected to said first threaded segment for movement along said operating rod by said manually adjustable dose interval control member between first and second locations and in which said dose volume control means further comprises a member threadably connected to said first threaded segment for movement along said operating rod by said adjustable interval in control member between first and second locations.

25. The device as defined in claim 24 further including locking means carried by said device housing for preventing rotation of said manually adjustable dose interval control member and said dose volume control member.

26. A device as defined in claim 25 in which said locking means comprises a locking rod movable within said device housing relative to said manually adjustable dose interval control member and said dose volume control member, said locking rod having a first protuberance engagable with said dose volume control member and a second protuberance engagable with said dose interval control member.

27. A device as defined in claim 26 further including biasing means carried by said device housing for yieldably resisting movement of said locking rod.

28. A device as defined in claim 26 in which said member of said volume control means is engagable with said stop of said body portion upon said operating rod assembly being moved toward said second location.

29. A device as defined in claim 28 in which said dispensing means farther includes first biasing means for yieldably resisting movement of said operating rod assembly toward said second location.

30. The device as defined in claim 29 in which said dispensing means further includes second biasing means for yieldably resisting movement of said patient operating delivery mechanism toward said second position.

31. A patient controlled infusion device for the sequential delivery of discrete doses of fluid to a delivery site comprising:
   (a) a device housing having a fluid outlet adapted to be in communication with the delivery site;
   (b) a fluid reservoir disposed within said device housing for containing the fluid to be delivered, said fluid reservoir having an outlet in communication with said fluid outlet of said housing;
   (c) dispensing means for sequentially dispensing first and second doses of fluid from said outlet of said fluid reservoir; and
   (d) an operating and control means operably associated with said dispensing means for controlling the dispensing of fluid from said fluid reservoir, said operating and control means comprising:
      (i) dose interval control means for controlling the interval of time between the dispensing of the discrete doses of fluid to the delivery site, said dose interval control means comprising an adjustable dose interval control member carried by said device housing, said dose interval control means further comprising a fluid containing compressible cellular structure that can be substantially saturated with a liquid; and
      (ii) dose volume control means for controlling of the volume of said discrete doses of fluid, said dose volume control means comprising an adjustable dose volume control member carried by said device housing.

32. A device as defined in claim 31 in which said dose interval control means further includes a yieldably deformable cellular mass that functions as an energy source when compressed.

33. A device as defined in claim 31 in which said dose interval control means further comprises a first hollow housing operably associated with said dispensing means, said fluid containing, compressible cellular structure being disposed within said hollow housing.

34. A device as defined in claim 32 in which said dose interval control means further includes fluid flow control means disposed between said fluid containing compressible cellular structure and said yieldably deformable cellular mass for controlling fluid flow therebetween.

* * * * *